United States Patent
Sidhu et al.

(10) Patent No.: US 10,689,442 B2
(45) Date of Patent: Jun. 23, 2020

(54) ANTIBODIES AGAINST FRIZZLED RECEPTOR

(71) Applicants: Sachdev Sidhu, Toronto (CA); Jason Moffat, Toronto (CA); Melanie Robitaille, Indooroopilly (AU); Stephane Angers, Mississauga (CA)

(72) Inventors: Sachdev Sidhu, Toronto (CA); Amandeep Gakhal, San Jose, CA (US); Guohua Pan, Oakville (CA); Jason Moffat, Toronto (CA); Melanie Robitaille, Toronto (CA); Stephane Angers, Mississauga (CA)

(73) Assignees: Sachdev Sidhu, Toronto (CA); Jason Moffat, Toronto (CA); Melanie Robitaille, Indooroopilly (AU); Stephanie Angers, Mississauga (CA)

( * ) Notice: Subject to any disclaimer, the term of this patent is extended or adjusted under 35 U.S.C. 154(b) by 0 days.

(21) Appl. No.: 16/057,093

(22) Filed: Aug. 7, 2018

(65) Prior Publication Data
US 2019/0202909 A1     Jul. 4, 2019

Related U.S. Application Data

(63) Continuation of application No. 14/911,983, filed as application No. PCT/US2014/051070 on Aug. 14, 2014, now Pat. No. 10,077,304.

(60) Provisional application No. 61/865,668, filed on Aug. 14, 2013.

(51) Int. Cl.
*C07K 16/28*     (2006.01)
*A61K 39/00*     (2006.01)

(52) U.S. Cl.
CPC ........ *C07K 16/28* (2013.01); *A61K 2039/505* (2013.01); *C07K 2317/21* (2013.01); *C07K 2317/33* (2013.01); *C07K 2317/55* (2013.01); *C07K 2317/565* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,485,045 A | 11/1984 | Regen |
| 4,522,811 A | 6/1985 | Eppstein et al. |
| 4,544,545 A | 10/1985 | Ryan et al. |
| 4,676,980 A | 6/1987 | Segal et al. |
| 4,681,581 A | 7/1987 | Coates et al. |
| 4,683,195 A | 7/1987 | Mullis et al. |
| 4,683,202 A | 7/1987 | Mullis |
| 4,735,210 A | 4/1988 | Goldenberg |
| 4,816,567 A | 3/1989 | Cabilly et al. |
| 4,946,778 A | 8/1990 | Ladner et al. |
| 5,013,556 A | 5/1991 | Woodle et al. |
| 5,030,719 A | 7/1991 | Umemoto et al. |
| 5,101,827 A | 4/1992 | Goldenberg |
| 5,102,990 A | 4/1992 | Rhodes |
| 5,151,510 A | 9/1992 | Stec et al. |
| 5,194,594 A | 3/1993 | Khawli et al. |
| 5,223,409 A | 6/1993 | Ladner et al. |
| 5,530,101 A | 6/1996 | Queen et al. |
| 5,545,806 A | 8/1996 | Lonberg et al. |
| 5,545,807 A | 8/1996 | Surani et al. |
| 5,585,089 A | 12/1996 | Queen et al. |
| 5,591,669 A | 1/1997 | Krimpenfort et al. |
| 5,612,205 A | 3/1997 | Kay et al. |
| 5,625,126 A | 4/1997 | Lonberg et al. |
| 5,625,825 A | 4/1997 | Rostoker et al. |
| 5,633,425 A | 5/1997 | Lonberg et al. |
| 5,643,763 A | 7/1997 | Dunn et al. |
| 5,648,471 A | 7/1997 | Buttram et al. |
| 5,661,016 A | 8/1997 | Lonberg et al. |
| 5,693,761 A | 12/1997 | Queen et al. |
| 5,693,792 A | 12/1997 | Torii et al. |
| 5,697,902 A | 12/1997 | Goldenberg |
| 5,714,350 A | 2/1998 | Co et al. |
| 5,721,367 A | 2/1998 | Kay et al. |
| 5,733,743 A | 3/1998 | Johnson et al. |
| 5,770,429 A | 6/1998 | Lonberg et al. |
| 5,789,215 A | 8/1998 | Berns et al. |
| 5,789,650 A | 8/1998 | Lonberg et al. |
| 5,777,085 A | 9/1998 | Co et al. |
| 5,814,318 A | 9/1998 | Lonberg et al. |
| 5,874,299 A | 2/1999 | Lonberg et al. |
| 5,877,397 A | 3/1999 | Lonberg et al. |

(Continued)

FOREIGN PATENT DOCUMENTS

| | | |
|---|---|---|
| EP | 0 463 151 B1 | 1/1992 |
| EP | 0 546 073 B1 | 6/1993 |

(Continued)

OTHER PUBLICATIONS

Baldrick, P., "Pharmaceutical Excipient Development: The Need for Preclinical Guidance," Regul. Toxicol Pharmacol. 32(2):2 W-8 (2000).

(Continued)

*Primary Examiner* — Elly-Gerald Stoica

(74) *Attorney, Agent, or Firm* — Cooley LLP; Ivor R. Elrifi; Cynthia Kozakiewicz

(57) ABSTRACT

This invention provides monoclonal antibodies that recognize one or more Frizzled receptors. The invention further provides methods of using such monoclonal antibodies as a therapeutic, diagnostic, and prophylactic.

8 Claims, 38 Drawing Sheets
Specification includes a Sequence Listing.

(56) References Cited

U.S. PATENT DOCUMENTS

| | | | |
|---|---|---|---|
| 5,939,598 | A | 8/1999 | Kucherlapati et al. |
| 6,023,010 | A | 2/2000 | Krimpenfort et al. |
| 6,075,181 | A | 6/2000 | Kucherlapati et al. |
| 6,114,598 | A | 9/2000 | Kucherlapati et al. |
| 6,150,584 | A | 11/2000 | Kucherlapati et al. |
| 6,162,963 | A | 12/2000 | Kucherlapati et al. |
| 6,255,458 | B1 | 7/2001 | Lonberg et al. |
| 6,521,404 | B1 | 2/2003 | Griffiths et al. |
| 2016/0194394 | A1 | 7/2016 | Sidhu et al. |

FOREIGN PATENT DOCUMENTS

| | | |
|---|---|---|
| EP | 0 586505 | 3/1994 |
| EP | 773 288 | 5/1997 |
| EP | 843 961 | 5/1998 |
| JP | H04504365 A | 8/1992 |
| JP | H10146194 | 6/1998 |
| JP | H10155492 | 6/1998 |
| JP | 2013-530929 A | 8/2013 |
| WO | WO 91/00360 | 1/1991 |
| WO | WO 92/01047 | 1/1992 |
| WO | WO 92/200373 | 1/1992 |
| WO | WO 92/03918 | 3/1992 |
| WO | WO 1992/011018 | 7/1992 |
| WO | WO 92/22645 | 12/1992 |
| WO | WO 92/22647 | 12/1992 |
| WO | WO 92/22670 | 12/1992 |
| WO | WO 93/08829 | 5/1993 |
| WO | WO 93/12227 | 6/1993 |
| WO | WO 94/00569 | 1/1994 |
| WO | WO 94/02602 | 2/1994 |
| WO | WO 94/011026 | 5/1994 |
| WO | WO 94/25585 | 11/1994 |
| WO | WO 94/29444 | 12/1994 |
| WO | WO 95/22618 | 8/1995 |
| WO | WO 96/14436 | 5/1996 |
| WO | WO 96/27011 | 9/1996 |
| WO | WO 96/34096 | 10/1996 |
| WO | WO 97/13852 | 4/1997 |
| WO | WO 97/38137 | 10/1997 |
| WO | WO 98/24884 | 6/1998 |
| WO | WO 98/24893 | 6/1998 |
| WO | WO 00/76310 | 12/2000 |
| WO | WO 2010/037041 | 4/2010 |
| WO | WO 2011/123785 A2 | 10/2011 |
| WO | WO 2013/080055 A2 | 6/2013 |

OTHER PUBLICATIONS

Blake and Litzi-Davis, "Evaluation of Peptide Libraries: An Iterative Strategy to Analyze the Reactivity of Peptide Mixtures with Antibodies," BioConjugate Chem. 3:510-513 (1992).
Bobo et al., "Convection-enhanced delivery of macromolecules in the brain," Proc. Natl. Acad. Sci. USA 91:2076-2080 (1994).
Bowie et al., "A Method to Identify Protein Sequences That Fold into a Known Three-Dimensional Structure," Science 253:164-171 (1991).
Brennan et al., "Preparation of Bispecific Antibodies by Chemical Recombination of Monoclonal Immunoglobulin $G_1$ Fragments," Science 229:81 (1985).
Brodeur et al., "Monoclonal Antibody Production Techniques and Applications: Mouse-Human Myeloma Partners for the Production of Heterohybridomas", in "Monoclonal Antibody Production Techniques and Applications," pp. 51-63 (1987).
Carell et al., "A Novel Procedure for the Synthesis of Libraries Containing Small Organic Molecules," Angew. Chem. Int. Ed. Engl. 33:2059 (1994).
Carell et al., "A Solution-Phase Screening Procedure for the Isolation of Active Compounds from a Library of Molecules," Angew. Chem. Int. Ed. Engl. 33(20):2061-2064 (1994).
Caron et al., "Engineered Humanized Dimeric Forms of IgG Are More Effective Antibodies," J. Exp Med., 176:1191-1195 (1992).

Charman, W. N., "Lipids, Lipophilic Drugs, and Oral Drug Delivery—Some Emerging Concepts," J Pharm Sci. 89(8):967-78 (2000).
Chen et al., "Intracellular Antibodies as a New Class of Therapeutic Molecules for Gene Therapy," Human Gene Therapy 5:595-601 (1994).
Chiswell et al., "Phage antibodies: will new 'colicional' antibodies replace monoclonal antibodies?", TIBTECH, 10:80-84 (1992).
Cho et al., "An Unnatural Biopolymer," Science 261:1303 (1993).
Chothia and Lesk, "Canonical Structures for the Hypervariable Regions of Immunoglobulins," J. Mol. Biol. 196: 901-917 (1987).
Chothia et al., "Conformations of immunoglobulin hypervariable regions," Nature, vol. 342, pp. 878-883 (1989).
Cole et al., "The EBV-Hybridoma Technique and its Application to Human Lung Cancer," Monoclonal Antibodies and Cancer Therapy, pp. 77-96 (1985).
Cote et al., "Generation of human monoclonal antibodies reactive with cellular antigens," Proc Natl Acad Sci USA, vol. 80, pp. 2026-2030 (1983).
Cull et al., "Screening for receptor ligands using large libraries of peptides linked to the C terminus of the lac repressor," Proc. Natl. Acad. Sci. USA 89:1865-1869 (1992).
Cwirla et al., "Peptides on phage: A vast library of peptides for identifying ligands," Proc. Natl. Acad. Sci. U.S.A. 87:6378-6382 (1990).
Davidson et al., "A model system for in vivo gene transfer into the central nervous system using an adenoviral vector," Nat. Genet 3:219 (1993).
Davies and Padlan, "Antibody-Antigen Complexes," Annual Rev Biochem 59:439-473 (1990).
Dayhoff, M. O., "Detecting Distant Relationships: Computer Methods and Results," in "Atlas of Protein Sequence and Structure," pp. 101-110 (vol. 5, National Biomedical Research Foundation (1972).
Devlin et al., "Random Peptide Libraries: A Source of Specific Protein Binding Molecules," Science 249:404-406 (1990).
DeWitt et al., ""Diversomers": An approach to nonpeptide, nonoligomeric chemical diversity," Proc. Natl. Acad. Sci. U.S.A. 90:6909 (1993).
Epstein et al., "Biological activity of liposome-encapsulated murine interferon γ is mediated by a cell membrane receptor," Proc. Natl. Acad. Sci. USA, 82:3688 (1985).
Erb et al., "Recursive deconvolution of combinatorial chemical libraries," Proc. Natl. Acad. Sci. U.S.A. 91:11422 (1994).
Evans et al., "Design of Nonpeptidal Ligands for a Peptide Receptor: Cholecystokinin Antagonists," J. Med. Chem., vol. 30, pp. 1229-1239 (1987).
Fanger et al., "Production and Use of Anti-FcR Bispecific Antibodies," ImmunoMethods 4:72-81 (1994).
Fauchère, J.-L., "Elements for the Rational Design of Peptide Drugs," Advances in Drug Research, vol. 15, pp. 29-69 (1986).
Felici, F., "Selection of Antibody Ligands from a Large Library of Oligopeptides Expressed on a Multivalent Exposition Vector," J. Mol. Biol. 222: 301-310 (1991).
Fellouse and Pal, "Methods for the Construction of Phage-Displayed Libraries" Biotechnology and Drug Discovery, 32 pages (2005).
Fellouse et al., "High-Throughput generation of synthetic antibodies from highly functional minimalist phage-displayed libraries," J Mol Biol 373:924-940 (2007).
Fodor et al., "Multiplexed biochemical assays with biological chips," Nature 364:555-556 (1993).
Gallop et al., "Applications of Combinatorial Technologies to Drug Discovery. 1. Background and Peptide Combinatorial Libraries," J. Med. Chem 37:1233 (1994).
Geller et al., "An HSV-1 Vector Expressing Tyrosine Hydroxylase Causes Production and Release of L-DOPA from Cultured Rat Striatal Cells," J. Neurochem 64:487 (1995).
Geller et al., "Long-term increases in neurotransmitter release from neuronal cells expressing a constitutively active adenylate cyclase from a herpes simplex virus type 1 vector," Proc Natl. Acad. Sci.: U.S.A. 90:7603 (1993).

(56) References Cited

OTHER PUBLICATIONS

Geller and Freese, "Infection of cultured central nervous system neurons with a defective herpes simplex virus 1 vector results in stable expression of *Escherichia coli* β-galactosidase," Proc Natl. Acad. Sci USA 87:1149 (1990).
Gershoni et al., "Epitope mapping—The first step in developing epitope-based vaccines," Biodrugs 21(3): 145-156 (2007).
Goding, J. W., "Production of Monoclonal Antibodies", in "Monoclonal Antibodies: Principles and Practice," Academic Press, pp. 59-103 (1986).
Gorman et al., "The Rous sarcoma virus long terminal repeat is a strong promoter when introduced into a variety of eukaryotic cells by DNA-mediated transfection," Proc. Natl. Acad. Sci. (USA) 79:6777 (1982).
Green et al., "Antigen-specific human monoclonal antibodies from mice engineered with human Ig heavy and light chain YACs," Nature Genetics 7:13-21 (1994).
Grosschedl et al., "Cell-Type Specificity of Immunoglobulin Gene Expression is Regulated by at Least Three DNA Sequence Elements," Cell 41:885-897 (1985).
Gruber et al., "Efficient Tumor Cell Lysis Mediated by a Bispecific Single Chain Antibody Expressed in *Escherichia coli*," Journal of Immunology 152:5368-5374 (1994).
Hanes and Pluckthun "In vitro selection and evolution of functional proteins by using ribosome display," PNAS USA 94:4937-4942 (1997).
Holliger et al., "'Diabodies': Small bivalent and bispecific antibody fragments," Proc. Natl. Acad. Sci. USA 90:6444-6448 (1993).
Hoogenboom et al., "Building Antibodies from their Genes," Immunological Reviews 130:43-68 (1992).
Houghten et al., "The Use of Synthetic Peptide Combinatorial Libraries for the Identification of Bioactive Peptides," Biotechniques 13:412-421 (1992).
Houghten et al., "General method for the rapid solid-phase synthesis of large numbers of peptides: Specificity of antigen-antibody interaction at the level of individual amino acids," PNAS USA 82:5131-5135 (1985).
Huse et al., "Generation of a Large Combinatorial Library of the Immunoglobulin Repertoire in Phage Lambda," Science 246:1275-1281 (1989).
Hwang et al., "Hepatic uptake and degradation of unilamellar sphingomyelin/cholesterol liposomes: A kinetic study," Proc. Natl Acad. Sci. USA, 77:4030 (1980).
Jansen et al., "Immunotoxins: Hybrid Molecules Combining High Specificity and Potent Cytotoxicity," Immunological Reviews 62:185-216 (1982).
Junghans et al., "Antibody-Based Immunotherapies for Cancer," Cancer Chemotherapy and Biotherapy: Principles and Practice, pp. 655-686 (1996).
Kaplitt et al., "Long-term gene expression and phenotypic correction using adeno-associated virus vectors in the mammalian bran," Nat. Genet. 8:148 (1994).
Killen and Lindstrom, "Specific killing of lymphocytes that cause experimental autoimmune myasthenia gravis by ricin toxin-acetylcholine receptor conjugates," Jour. Immun. 133:1335-2549 (1984).
Kohler and Milstein, "Continuous cultures of fused cells secreting antibody of predefined specificity," Nature 256:495 (1975).
Kostelny et al., "Formation of a Bispecific Antibody by the Use of Leucine Zippers," Journal of Immunol. 148:1547-1553 (1992).
Kozbor and Roder, "The production of monoclonal antibodies from human lymphocytes," Immunology Today 4:72 (1983).
Kozbor et al., "A human hybrid myeloma for production of human monoclonal antibodies," J. Immunol. 133:3001 (1984).
Lam, K., "Application of combinatorial library methods in cancer research and drug discovery," Anticancer Drug Design 12:145 (1997).
Lam et al., "A new type of synthetic peptide library for identifying ligand-binding activity," Nature 354: 82-84 (1991).
LaPlanche et al., "Phosphorothioate-modified oligodeoxyribonucleotides. III. NMR and UV spectroscopic studies of the $R_p$-$R_p$, $S_p$-$S_p$, and $R_p$-$S_p$ duplexes, $[dCGG_sAATTCC)]_2$, derived from diastereomeric 0-ethyl phosphorothioates," Nucleic Acids Research, vol. 14, No. 22, pp. 9081-9093 (1986).
Le Gal La Salle et al., "An Adenovirus Vector for Gene Transfer into Neurons and Glia in the Brain," Science 259:988 (1993).
Liu et al., "Chimeric mouse-human IgGi antibody that can mediate lysis of cancer cells," PNAS 84:3439-3443 (1987).
Liu et al., "Production of a mouse-human chimeric monoclonal antibody to CD20 with potent Fc-dependent biologic activity," Journal of Immunology 139: 3521-3526 (1987).
Malmqvist, M., "Biosepcific interaction analysis using biosensor technology," Nature 361:186-187 (1993).
Marasco et al., "Design, intracellular expression, and activity of a human anti-human immunodeficiency virus type 1 gp120 single-chain antibody," Proc. Natl. Acad. Sci. USA, 90:7889-7893 (1993).
Marasco, W. A., "Intrabodies: turning the humoral immune system outside in for intracellular immunization," Gene Therapy 4:11-15 (1997).
Martin et al., "Irreversible Coupling of Immunoglobulin Fragments to Preformed Vesicles," J. Biol. Chem. 257:286-288 (1982).
Milstein and Cuello, "Hybrid hybridomas and their use in immunohistochemistry," Nature 305:537-539 (1983).
Morrison, S. L., "Success in specification," Nature 368:812-13 (1994).
Morrison et al., "High-flow microinfusion: tissue penetration and pharmacodynamics," Am. J. Physiol. 266:292-305 (1994).
Munson and Pollard, "Ligand: A Versatile Computerized Approach for Characterization of Ligand-Binding Systems," Anal. Biochem. 107:220 (1980).
Needleman and Wunsch, "A General Method Applicable to the Search for Similarities in the Amino Acid Sequence of Two Proteins," J. Mol. Biol., vol. 48, pp. 443-453 (1970).
Okayama et al., "A cDNA Cloning Vector That Permits Expression of cDNA Inserts in Mammalian Cells," Molecular and Cellular Biology 3(2):280-289 (1983).
Parmley and Smith, "Antibody-selectable filamentous fd phage vectors: affinity purification of target genes," Gene 73:305-318 (1988).
Pearson and Liplman, "Improved tools for biological sequence comparison," Proc. Natl. Acad. Sci. USA, vol. 85, pp. 2444-2448 (1988).
Pinilla et al., "Rapid Identification of High Affinity Peptide Ligands Using Positional Scanning Synthetic Peptide Combinatorial Libraries," Biotechniques 13(6): 901-905 (1992).
Powell et al., "Compendium of excipients for parenteral formulations," PDA J Pharm Sci Technol. 52:238-311 (1998).
Ramakrishnan et al., "Comparison of the Selective Cytotoxic Effects of Immunotoxins Containing Ricin A Chain or Pokeweed Antiviral Protein and Anti-Thy 1.1 Monoclonal Antibodies," Cancer Res. 44:201-208 (1984).
Rizo and Gierasch, "Constrained Peptides: Models of Bioactive Peptides and Protein Substructures," Ann. Rev. Biochem. 61:387 (1992).
Russel et al., "Retroviral vectors displaying functional antibody fragments," Nucl. Acids Research 21:1081-1085 (1993).
Scott, J. K., "Discovering peptide ligands using epitope libraries," TIBS, vol. 17:241-245 (1992).
Scott and Smith, "Searching for Peptide Ligands with an Epitope Library," Science 249: 386-390 (1990).
Shalaby et al., "Development of Humanized Bispecitic Antibodies Reactive with Cytotoxic Lymphocytes and Tumor Cells Overexpressing the HER2 Protooncogene," J. Exp. Med. 175:217-225 (1992).
Shopes, B., "A genetically engineered human IgG mutant with enhanced cytolytic activity," J. Immunol. 148:2918-2922 (1992).
Sidhu and Fellouse, "Synthetic therapeutic antibodies," Nat Chem Biol. 2(12):682-8 (2006).
Smith and Waterman, "Comparison of Biosequences," Advances in Applied Mathematics, vol. 2, pp. 482-489 (1981).

(56) References Cited

OTHER PUBLICATIONS

Stec et al., "Automated Solid-Phase Synthesis, Separation, and Stereochemistry of Phosphorothioate Analogues of Oligodeoxyribonucleotides," J. Am. Chem. Soc., vol. 106, No. 20, pp. 6077-6079 (1984).
Stein et al., "Physicochemical properties of phosphorothioate oligodeoxynucleotides," Nucl. Acids Res., vol. 16, No. 8, pp. 3209-3221 (1988).
Stevenson et al., "A chimeric antibody with dual Fe regions (bisFabFc) prepared by manipulations at the IgG hinge," Anti-Cancer Drug Design 3:219-230 (1989).
Suresh et al., "Bispecific Monoclonal Antibodies from Hybrid Hybridomas," Methods in Enzymology 121:210 (1986).
Thornton et al., "Prediction of progress at last," Nature 354:105-106 (1991).
Traunecker et al., "Bispecific single chain molecules (Janusins) target cytotoxic lymphocytes on HIV infected cells," EMBO Journal 10:3655-3659 (1991).
Traunecker et al., "Janusin: New Molecular Design for Bispecific Reagents," International Journal of Cancer (Suppl.) 7:51-52 (1992).
Tutt et al., "Trispecific F(ab')$_3$ Derivatives that use Cooperative Signaling via the TCR/CD3 Complex and CD2 to activate and redirect resting cytotoxic T cells," Journal of Immunology, 147:60-69 (1991).
Uhlmann and Peyman, "Antisense Oligonucleotides: A New Therapeutic Principle," Chemical Reviews, vol. 90, No. 4, pp. 544-584 (1990).
Veber and Freidinger, "The design of metabolically-stable peptide analogs," TINS, pp. 392-396 (1985).
Vitetta et al., "Redesigning Nature's Poisons to Create Anti-Tumor Reagents," Science 238:1098 (1987).
Vitetta et al., "Immunotoxins: magic bullets or misguided missiles?", Immunology Today 14(6):252-259 (1993).
Wang, W., "Lyophilization and development of solid protein pharmaceuticals," Int. J. Pharm. 203:1-60 (2000).
Wilkinson, D., "Ultimate Abs," The Scientist, vol. 14, No. 8, pp. 25-28 (2000).
Winter and Harris, "Humanized antibodies," Immunology Today 14:43-46 (1993).
Wright et al., "Genetically Engineered Antibodies: Progress and Prospects," Critical Reviews in Immunology 12(3,4):125-168 (1992).
Yang et al., "Cellular and Humoral Immune Responses to Viral Antigens Create Barriers to Lung-Directed Gene Therapy with Recombinant Adenoviruses," Journal of Virology 69:2004-2015 (1995).
Zon et al., "Phosphorothioate oligonucleotides: chemistry, purification, analysis, scale-up and future directions," Anti Cancer Drug Design 6:539-568 (1991).
Zon et al., "Phosphorothioate Oligonucleotides", in "Oligonucleotides and Analogues: A Practical Approach," F. Eckstein, Ed., Oxford University Press, Oxford England pp. 87-108 (1991).
Zuckermann et al., "Discovery of Nanomolar Ligands for 7-Transmembrane G-Protein-Coupled Receptors from a Diverse N-(Substituted) glycine Peptoid Library," J. Med. Chem. 37:2678 (1994).

FIGURE 1A

Light chain amino acid:

DIQMTQSPSSLSASVGDRVTITCRASQSVSSAVAWYQQKPGKAPKLLIYSASSLY
SGVPSRFSGSRSGTDFTLTISSLQPEDFATYYCQQAAYHWPPLFTFGQGTKVEIKR
TVAAPSVFIFPPSDSQLKSGTASVVCLLNNFYPREAKVQWKVDNALQSGNSQES
VTEQDSKDSTYSLSSTLTLSKADYEKHKVYACEVTHQGLSSPVTKSFNRGECGG
S (SEQ ID NO: 2)

Light chain nucleotide sequence:

GATATCCAGATGACCCAGTCCCCGAGCTCCCTGTCCGCCTCTGTGGGCGATA
GGGTCACCATCACCTGCCGTGCCAGTCAGTCCGTGTCCAGCGCTGTAGCCTG
GTATCAACAGAAACCAGGAAAAGCTCCGAAGCTTCTGATTTACTCGGCATCC
AGCCTCTACTCTGGAGTCCCTTCTCGCTTCTCTGGTAGCCGTTCCGGGACGGA
TTTCACTCTGACCATCAGCAGTCTGCAGCCGGAAGACTTCGCAACTTATTACT
GTCAGCAAGCTGCTTACCATTGGCCGCCGCTGTTCACGTTCGGACAGGGTAC
CAAGGTGGAGATCAAACGAACTGTGGCTGCACCATCTGTCTTCATCTTCCCGC
CATCTGATTCACAGTTGAAATCTGGAACTGCCTCTGTTGTGTGCCTGCTGAAT
AACTTCTATCCCAGAGAGGCCAAAGTACAGTGGAAGGTGGATAACGCCCTCC
AATCGGGTAACTCCCAGGAGAGTGTCACAGAGCAGGACAGCAAGGACAGCA
CCTACAGCCTCAGCAGCACCCTGACGCTGAGCAAAGCAGACTACGAAAAAC
ATAAAGTCTACGCCTGCGAAGTCACCCATCAGGGCCTGAGCTCGCCCGTCAC
AAAGAGCTTCAACAGGGGAGAGTGTGGTGGTTCT (SEQ ID NO: 1)

FIGURE 1B

Heavy Chain amino acid sequence:

EVQLVESGGGLVQPGGSLRLSCAASGFNLYYSSMHWVRQAPGKGLEWVAYISP
YSGYTSYADSVKGRFTISADTSKNTAYLQMNSLRAEDTAVYYCARYWAMDYW
GQGTLVTVSSASTKGPSVFPLAPSSKSTSGGTAALGCLVKDYFPEPVTVSWNSGA
LTSGVHTFPAVLQSSGLYSLSSVVTVPSSSLGTQTYICNVNHKPSNTKVDKKVEP
KSC (SEQ ID NO: 4)

Heavy Chain nucleotide sequence:

GAGGTTCAGCTGGTGGAGTCTGGCGGTGGCCTGGTGCAGCCAGGGGGCTCAC
TCCGTTTGTCCTGTGCAGCTTCTGGCTTCAACCTCTATTATTCTTCTATGCACT
GGGTGCGTCAGGCCCCGGGTAAGGGCCTGGAATGGGTTGCATATATTTCTCC
TTATTCTGGCTATACTTCTTATGCCGATAGCGTCAAGGGCCGTTTCACTATAA
GCGCAGACACATCCAAAAACACAGCCTACCTACAAATGAACAGCTTAAGAG
CTGAGGACACTGCCGTCTATTATTGTGCTCGCTACTGGGCTATGGACTACTGG
GGTCAAGGAACCCTGGTCACCGTCTCCTCGGCCTCCACCAAGGGTCCATCGG
TCTTCCCCCTGGCACCCTCCTCCAAGAGCACCTCTGGGGGCACAGCGGCCCTG
GGCTGCCTGGTCAAGGACTACTTCCCCGAACCGGTGACGGTGTCGTGGAACT
CAGGCGCCCTGACCAGCGGCGTGCACACCTTCCCGGCTGTCCTACAGTCCTC
AGGACTCTACTCCCTCAGCAGCGTGGTGACCGTGCCCTCCAGCAGCTTGGGC
ACCCAGACCTACATCTGCAACGTGAATCACAAGCCCAGCAACACCAAGGTCG
ACAAGAAAGTTGAGCCCAAATCTTGT (SEQ ID NO: 3)

FIGURE 1C

| Fab ID | CDR L3 | CDR H1 | CDR H2 | CDR H3 | Fab ID | CDR L3 | CDR H1 | CDR H2 | CDR H3 |
|---|---|---|---|---|---|---|---|---|---|
| Fzd7-R3-H5 | YGWFAYYPI (SEQ ID NO: 5) | LSSSSI (SEQ ID NO: 6) | YIYSSSGYTS (SEQ ID NO: 7) | TVRGSKKPYFSGWAM (SEQ ID NO: 8) | Fzd7-R2-E5 | ASWYPI (SEQ ID NO: 9) | IYSSSM (SEQ ID NO: 10) | SIYSSYGYTS (SEQ ID NO: 11) | PGYWGYYWGAYGM (SEQ ID NO: 12) |
| Fzd7-R3-B7 | AYYPLF (SEQ ID NO: 13) | ISYSSM (SEQ ID NO: 14) | SIYPSSYGYTS (SEQ ID NO: 15) | VYWSSSYWAGGYWVGSAF (SEQ ID NO: 16) | Fzd7-R2-F12 | AYAPF (SEQ ID NO: 17) | ISYSYM (SEQ ID NO: 18) | SIYSSYSYTS (SEQ ID NO: 19) | SSAWFGHAGFGGAM (SEQ ID NO: 20) |
| Fzd7-R3-D11 | YFPSGLI (SEQ ID NO: 21) | ISYSYM (SEQ ID NO: 18) | SISPSSYGYTS (SEQ ID NO: 22) | SVSWWYSWWSWGM (SEQ ID NO: 23) | Fzd7-R3-D10 | YWAPI (SEQ ID NO: 24) | IYYYYM (SEQ ID NO: 25) | SIYSYSGSTY (SEQ ID NO: 26) | YASYVGYYPWAL (SEQ ID NO: 27) |
| Fzd7-R3-F3 | GGHYWLI (SEQ ID NO: 28) | ISYSSM (SEQ ID NO: 14) | SISSSYGYTS (SEQ ID NO: 29) | SYYGYYVGYGYSSWSGSGM (SEQ ID NO: 30) | Fzd7-R2-B5 | GSASSALI (SEQ ID NO: 31) | ISYSSM (SEQ ID NO: 14) | SIYSSYGYTS (SEQ ID NO: 11) | FYSSFYFFWYPPAGL (SEQ ID NO: 32) |
| Fzd7-R3-E9 | AVYHALI (SEQ ID NO: 33) | IYYSSM (SEQ ID NO: 34) | SISSYSSTY (SEQ ID NO: 35) | SAVVHYPAGYWVYWGWYAF (SEQ ID NO: 36) | Fzd7-R2-A4 | AYWWVGPI (SEQ ID NO: 37) | LSYSSI (SEQ ID NO: 38) | YISSSYGYTS (SEQ ID NO: 39) | FSAYWAWHGL (SEQ ID NO: 40) |
| Fzd7-R3-B10 | YWASLI (SEQ ID NO: 41) | ISYYYI (SEQ ID NO: 42) | YISPYYGSTY (SEQ ID NO: 43) | SWSYSYYYSHPGWSPVWAM (SEQ ID NO: 44) | Fzd7-R2-E3 | VSGGGGLI (SEQ ID NO: 45) | IYSSYI (SEQ ID NO: 46) | YIYSYSGYTY (SEQ ID NO: 47) | WYHPYWYASAI (SEQ ID NO: 48) |
| Fzd7-R3-G7 | YGYWWVSLF (SEQ ID NO: 49) | LYYYSI (SEQ ID NO: 50) | STYSSYSYTY (SEQ ID NO: 51) | WWPGHYSGYGSGAL (SEQ ID NO: 52) | Fzd7-R3-B10 | WAYGPF (SEQ ID NO: 53) | IYYYSM (SEQ ID NO: 54) | SIYSSYSYTS (SEQ ID NO: 19) | SSPGADYGL (SEQ ID NO: 55) |
| Fzd7-R3-C3 | SSGPWYYPI (SEQ ID NO: 56) | FSSSSI (SEQ ID NO: 57) | SISSSYGYTY (SEQ ID NO: 58) | WWSGGWYYSYGM (SEQ ID NO: 59) | Fzd7-R2-D7 | SYVYYLI (SEQ ID NO: 60) | ISYSSM (SEQ ID NO: 61) | YIYPYSSYTY (SEQ ID NO: 62) | YHGFYGM (SEQ ID NO: 63) |
| Fzd7-R3-A10 | SYWPGWPI (SEQ ID NO: 64) | FSSSSI (SEQ ID NO: 57) | YIYPYYGYTY (SEQ ID NO: 65) | WVVAGHYGM (SEQ ID NO: 66) | Fzd7-R2-C10 | SAWWASLF (SEQ ID NO: 67) | ISSYSI (SEQ ID NO: 68) | SIYPYSSYTY (SEQ ID NO: 69) | YSGFAM (SEQ ID NO: 70) |
| Fzd7-R3-B2 | SSYSLI (SEQ ID NO: 71) | LSYSYM (SEQ ID NO: 72) | SIYSSYGYTS (SEQ ID NO: 11) | YYGWAYYYSYFPAWAGGGI (SEQ ID NO: 73) | Fzd7-R2-E11 | YSYGYALF (SEQ ID NO: 74) | LSSYYM (SEQ ID NO: 75) | SIYPYYSYTY (SEQ ID NO: 76) | YWSGF (SEQ ID NO: 77) |
| Fzd7-R3-B9 | WWASGVGPF (SEQ ID NO: 78) | LYSSSI (SEQ ID NO: 79) | YISSYYSSTY (SEQ ID NO: 80) | PAM (SEQ ID NO: 81) | Fzd7-R2-F9 | WYYGWHLI (SEQ ID NO: 82) | ISYSSI (SEQ ID NO: 83) | SIYPSYGYTY (SEQ ID NO: 84) | YGYFGM (SEQ ID NO: 85) |
| Fzd7-R3-D7 | YVYSSLI (SEQ ID NO: 86) | ISYYSM (SEQ ID NO: 61) | STYPSYGSTY (SEQ ID NO: 87) | PGVGGYYAM (SEQ ID NO: 88) | Fzd7-R2-E3 | SYSASLF (SEQ ID NO: 89) | LYYSYI (SEQ ID NO: 90) | SISPSYSSTY (SEQ ID NO: 91) | VSYWGAGM (SEQ ID NO: 92) |

FIGURE 1C, cont'd

| Fab ID | CDR L3 | CDR H1 | CDR H2 | CDR H3 | Fab ID | CDR L3 | CDR H1 | CDR H2 | CDR H3 |
|---|---|---|---|---|---|---|---|---|---|
| Fzd7-R3-E4 | SSYSLI (SEQ ID NO: 71) | LSYYSM (SEQ ID NO: 93) | SIYPSYGYTY (SEQ ID NO: 84) | PSPGSYHGM (SEQ ID NO: 94) | Fzd7-R2-A9 | WGSYVALF (SEQ ID NO: 95) | IYSYSI (SEQ ID NO: 96) | SIYPSYGSTY (SEQ ID NO: 97) | VGPGSYGGL (SEQ ID NO: 98) |
| Fzd7-R3-E7 | FWGLF (SEQ ID NO: 99) | ISYYSM (SEQ ID NO: 61) | SIYPSYSSTY (SEQ ID NO: 100) | PSPGGYSAL (SEQ ID NO: 101) | Fzd7-R2-E7 | YYYSVWLI (SEQ ID NO: 102) | ISYYYM (SEQ ID NO: 103) | YISPSSSYTS (SEQ ID NO: 104) | WYGWAL (SEQ ID NO: 105) |
| Fzd7-R3-C11 | PAYSAPI (SEQ ID NO: 106) | ISYYSM (SEQ ID NO: 61) | SIYSSYGSTY (SEQ ID NO: 107) | VGPGGFGAL (SEQ ID NO: 108) | Fzd7-R2-F1 | SYYPI (SEQ ID NO: 109) | LSYYI (SEQ ID NO: 110) | SIYPSYSSTY (SEQ ID NO: 100) | FSGWAL (SEQ ID NO: 111) |
| Fzd7-R3-G2 | GVYLF (SEQ ID NO: 112) | IYSSSI (SEQ ID NO: 113) | SIYSSYGSTS (SEQ ID NO: 114) | YHYPFGHAL (SEQ ID NO: 115) | Fzd7-R2-G1 | WGYGALI (SEQ ID NO: 116) | ISYSSI (SEQ ID NO: 83) | SIYPSPGYTS (SEQ ID NO: 117) | HGWYGL (SEQ ID NO: 118) |
| Fzd7-R3-D9 | SSYSLI (SEQ ID NO: 71) | LSYSSM (SEQ ID NO: 119) | SIYSSYSSTS (SEQ ID NO: 120) | GAGYYWHYYYVHGAM (SEQ ID NO: 121) | Fzd7-R2-G6 | YYSLF (SEQ ID NO: 122) | IYYYSM (SEQ ID NO: 54) | YISPSYGYTY (SEQ ID NO: 123) | GYFYSWGGM (SEQ ID NO: 124) |
| Fzd7-R3-G9 | YYYSSPI (SEQ ID NO: 125) | ISYYYI (SEQ ID NO: 42) | YISPSSGYTS (SEQ ID NO: 126) | GYPVYSWVWSFGAF (SEQ ID NO: 127) | Fzd7-R2-H1 | WGYGALI (SEQ ID NO: 116) | ISYSSI (SEQ ID NO: 83) | SIYPSPGYTS (SEQ ID NO: 117) | HGWYGL (SEQ ID NO: 118) |
| Fzd7-R3-H3 | AAYHWPFLF (SEQ ID NO: 128) | LYYSSM (SEQ ID NO: 129) | YISPSYGYTS (SEQ ID NO: 130) | YWAM (SEQ ID NO: 131) | Fzd7-R2-B11 | YWYGVAPI (SEQ ID NO: 132) | ISSSYI (SEQ ID NO: 133) | YIYSSYGSTY (SEQ ID NO: 134) | ASWYAL (SEQ ID NO: 135) |
| Fzd7-R2-H6 | AVYLI (SEQ ID NO: 136) | ISYYSI (SEQ ID NO: 137) | SIYPYSGSTY (SEQ ID NO: 138) | WAPHSSSWWSVYGWSAWAF (SEQ ID NO: 139) | Fzd7-R2-A7 | YFYSSYSPI (SEQ ID NO: 140) | ISYSYM (SEQ ID NO: 18) | YIYPSYSSTS (SEQ ID NO: 141) | ASYWAL (SEQ ID NO: 142) |
| Fzd7-R2-D5 | SVHWYPF (SEQ ID NO: 143) | ISYYSI (SEQ ID NO: 144) | YIYPYSGSTY (SEQ ID NO: 145) | WAHYGYYGFSYSVYSGGM (SEQ ID NO: 146) | Fzd7-R2-H8 | YHYGYYPF (SEQ ID NO: 147) | LSSSYI (SEQ ID NO: 148) | YIYSSYSSTS (SEQ ID NO: 134) | ASWWAI (SEQ ID NO: 149) |
| Fzd7-R2-B8 | SSYSLI (SEQ ID NO: 71) | ISSYYI (SEQ ID NO: 150) | SISSSGYTS (SEQ ID NO: 58) | PWSHYSSGAYWHPWSGHAL (SEQ ID NO: 151) | Fzd7-R2-A1 | SFYWGYPPF (SEQ ID NO: 152) | IYSSSI (SEQ ID NO: 113) | SIYSYGYTY (SEQ ID NO: 153) | WYAF (SEQ ID NO: 154) |
| Fzd7-R2-C8 | YSPSSFLI (SEQ ID NO: 155) | IYYSYI (SEQ ID NO: 156) | SISSSSGYTS (SEQ ID NO: 157) | SYGYYYFYYGGM (SEQ ID NO: 158) | Fzd7-R2-A2 | YYHPI (SEQ ID NO: 159) | ISSYYI (SEQ ID NO: 150) | SIYPYSSTY (SEQ ID NO: 160) | VWYGAM (SEQ ID NO: 161) |
| Fzd7-R2-C11 | GHYPYYLF (SEQ ID NO: 162) | IYYSM (SEQ ID NO: 163) | SIYSYSGYTY (SEQ ID NO: 164) | SVWGYPYGM (SEQ ID NO: 165) | Fzd7-R2-C11 | GSYSPF (SEQ ID NO: 165) | ISYYSM (SEQ ID NO: 61) | SIYPYSGYTY (SEQ ID NO: 166) | WHGYGI (SEQ ID NO: 167) |

FIGURE 1C, cont'd

| Fab ID | CDR L3 | CDR H1 | CDR H2 | CDR H3 | Fab ID | CDR L3 | CDR H1 | CDR H2 | CDR H3 |
|---|---|---|---|---|---|---|---|---|---|
| Fzd7-R2-D2 | SYSGWGPF (SEQ ID NO: 168) | ISSSYI (SEQ ID NO: 133) | SISSSSSYTY (SEQ ID NO: 169) | SAYPFSWSYPSYVGYYSGL (SEQ ID NO: 170) | Fzd7-R2-A12 | GFAYSYLF (SEQ ID NO: 171) | ISYSYM (SEQ ID NO: 18) | YIYPYYGYTY (SEQ ID NO: 65) | GYYGL (SEQ ID NO: 172) |
| Fzd7-R2-D6 | FYYSLI (SEQ ID NO: 173) | ISYSSM (SEQ ID NO: 14) | SIYSSYSYTS (SEQ ID NO: 19) | SYGPWAPGWAAYWGGYGM (SEQ ID NO: 174) | Fzd7-R2-B2 | AYAYLI (SEQ ID NO: 175) | ISYSSM (SEQ ID NO: 14) | SISSSYGYTY (SEQ ID NO: 58) | SGGHFYWYVAAAM (SEQ ID NO: 176) |
| Fzd7-R2-H11 | YSGPI (SEQ ID NO: 177) | ISSSYI (SEQ ID NO: 133) | YIYPYYSYTY (SEQ ID NO: 178) | SVTYHSSGWVPPWYWGYAF (SEQ ID NO: 179) | Fzd7-R2-C12 | SSYSLI (SEQ ID NO: 71) | LSYSYM (SEQ ID NO: 72) | SIYSSYGYTS (SEQ ID NO: 11) | YYGWAYYYSYFPAWAGGGI (SEQ ID NO: 73) |
| Fzd7-R2-H4 | YSSPI (SEQ ID NO: 180) | IYSSSI (SEQ ID NO: 113) | YISPYYSYTY (SEQ ID NO: 181) | SVWVYWGSWYSYSHASGL (SEQ ID NO: 182) | Fzd7-R2-A3 | AFGWPLI (SEQ ID NO: 183) | ISYYYI (SEQ ID NO: 42) | YIYPYSGSTS (SEQ ID NO: 184) | AGWVYGPYGF (SEQ ID NO: 185) |
| Fzd7-R2-B10 | GSVWLF (SEQ ID NO: 186) | ISSSSM (SEQ ID NO: 187) | SISSSSSYTY (SEQ ID NO: 169) | NGSHWSPSYSGWIYYSYAL (SEQ ID NO: 188) | Fzd7-R2-B12 | SSYSLI (SEQ ID NO: 71) | LSYSYM (SEQ ID NO: 72) | SISSSYGYTY (SEQ ID NO: 58) | AAGPYWYSYWYSAM (SEQ ID NO: 189) |
| Fzd7-R2-G4 | AYAYLI (SEQ ID NO: 175) | ISYSSM (SEQ ID NO: 14) | SISSSYGYTY (SEQ ID NO: 58) | SGGHFYWYVAAAM (SEQ ID NO: 176) | Fzd7-R2-C1 | YGHYLI (SEQ ID NO: 190) | LYSYSM (SEQ ID NO: 191) | SISSYYGSTY (SEQ ID NO: 192) | AHGSSPGWYYAPYAGGGI (SEQ ID NO: 193) |
| Fzd7-R2-E9 | SYVGGPF (SEQ ID NO: 194) | ISYSM (SEQ ID NO: 61) | SISSSYSSTY (SEQ ID NO: 195) | GYWVYVGWGAYYGPVGM (SEQ ID NO: 196) | | | | | |

FIGURE 1D

| Fab ID | CDR L3 | CDR H1 | CDR H2 | CDR H3 |
|---|---|---|---|---|
| Fzd7-R3-H5 | TACGGTTGGTTCGCTTACTACCCGATC (SEQ ID NO: 197) | CTCTCTTCTTCTTCTCTAT (SEQ ID NO: 198) | TATATTTATTCTTCTTCTTGGCTAT ACTTCT (SEQ ID NO: 199) | ACTGTTCGTGGATCCAAAAACCGTACTTCTCTGGTT GGGCTATG (SEQ ID NO: 200) |
| Fzd7-R3-B7 | GCTTACTACCCGCTGTTC (SEQ ID NO: 201) | ATCTCTTATTCTTCTTCTATG (SEQ ID NO: 202) | TCTATTTATCCTTCTTCTTATGGCTAT ACTTCT (SEQ ID NO: 203) | GTTTACTGGTCTTCTTCTTACTGGGCTGGTGGTTACT GGGTTGGTTCTGCTTT (SEQ ID NO: 204) |
| Fzd7-R3-D11 | TACTTCCCGTCTGGTCTGATC (SEQ ID NO: 205) | ATCTCTTATTCTTATATG (SEQ ID NO: 206) | TCTATTTCTCCTTCTTCTCTGGCTAT ACTTCT (SEQ ID NO: 207) | TCTGTTTCTTGGTGGTACTCTTGGTGGTCTTGGGTA TG (SEQ ID NO: 208) |
| Fzd7-R3-F3 | GGTGGTCATTACTGGCTGATC (SEQ ID NO: 209) | ATCTCTTATTCTTCTCTAT (SEQ ID NO: 210) | TCTATTTCTTCTTCTTCTTATGGCTAT ACTTCT (SEQ ID NO: 211) | TCTTACTACGGTTACTACGTTGGTTACGGTTACTCTT CTTGGTCTGGTTCTGGTATG (SEQ ID NO: 211) |
| Fzd7-R3-E9 | GCTGTTTACCATGCTCTGATC (SEQ ID NO: 212) | ATCTATTATTCTTCTCTAT (SEQ ID NO: 213) | TCTATTTCTTCTTATTCTAGCTCT ACTTAT (SEQ ID NO: 214) | TCTGCTGTTGTTCATTACCCGGCTGGTGGTTACTGGTTT ACTGGGGTTGGTACGCTTT (SEQ ID NO: 215) |
| Fzd7-R3-D11 | TACTGGGCTTCTCTGATC (SEQ ID NO: 216) | ATCTCTTATTATTATATC (SEQ ID NO: 217) | TATATTTCTCCTTATTATATGCTCT ACTTAT (SEQ ID NO: 218) | TCTTGGTCTTACTCTTACACTACTCTCATCCGGGTTG GTCTCCGGTTTGGGCTATG (SEQ ID NO: 219) |
| Fzd7-R3-G7 | TACGGTTACTGGTGGGTTTCTC TGTTC (SEQ ID NO: 220) | CTCTATTATTCTCTAT (SEQ ID NO: 221) | TCTATTTATTCTTATTCTAGCTAT ACTTAT (SEQ ID NO: 222) | TGGTGGCCTGGTCATTACTCTGGTTACGGTTCTGGTG CTTTG (SEQ ID NO: 223) |
| Fzd7-R3-C3 | TCTTTCTGGTCCGTGGTACTACC CGATC (SEQ ID NO: 224) | TTTCTCTTCTTCTCTATA (SEQ ID NO: 225) | TCTATTTCTTCTTCTCTTATGGCTAT ACTTAT (SEQ ID NO: 226) | TGGTGGTCTGGTTGGTACTACTCTTACGGTATG (SEQ ID NO: 227) |
| Fzd7-R3-A10 | TCTTACTGGCCGGGTTGGCCGA TC (SEQ ID NO: 228) | TTTTCTTCTTCTCTATA (SEQ ID NO: 225) | TATATTTATCCTTATTATTAGGCTAT ACTTCT (SEQ ID NO: 229) | TGGGTTGTTGCTGGTCATTACGGTATG (SEQ ID NO: 230) |
| Fzd7-R3-B2 | TCTTCTTATTCTCTGATC (SEQ ID NO: 231) | CTCTATTCTTCTCTATC (SEQ ID NO: 232) | TCTATTTCTTCTTCTTATGGCTAT ACTTCT (SEQ ID NO: 233) | TACTACGGTTGGCTTACTACTACTCTTACTTCCCGG CTTGGGCTGGTGGTGGTATT (SEQ ID NO: 234) |
| Fzd7-R3-B9 | TGGTGGGCTTCTGGTGTTGGTC CGTTC (SEQ ID NO: 235) | CTCTATTCTTCTCTATG (SEQ ID NO: 236) | TATATTTCTTCTTATTATAGCTCT ACTTCT (SEQ ID NO: 237) | CCGGGTGTTGGTGGTTACTACGGTATG (SEQ ID NO: 238) |
| Fzd7-R3-D7 | TACGGTTACTCTTCCTGATC (SEQ ID NO: 239) | ATCTCTTATTATTCTCTATG (SEQ ID NO: 240) | TCTATTTATCCTTCTTCTTATGGCTAT ACTTAT (SEQ ID NO: 241) | CCGGTCTCCGGGTTACTACCATGGTATG (SEQ ID NO: 242) |
| Fzd7-R3-E4 | TTCTGGGGTCTGTTC (SEQ ID NO: 246) | ATCTCTTATTACTCCTATG (SEQ ID NO: 243) | TCTATTTATCCTTCTTATAGCTCT ACTTAT (SEQ ID NO: 244) | CCGTCTCCGGGTGGTTACTCTGCTTTG (SEQ ID NO: 245) |
| Fzd7-R3-E7 | CCGGCTTACTCTGCTCCGATC (SEQ ID NO: 250) | ATCTCTTATTATTCTCTATG (SEQ ID NO: 247) | TCTATTTATCCTTCTTCTTATAGCTCT ACTTAT (SEQ ID NO: 248) | GTTGGTCCGGGTGGTTTCGGTGCTTTG (SEQ ID NO: 249) |
| Fzd7-R3-C11 | GGTGTTTACCTGTTC (SEQ ID NO: 253) | ATCTATTCTTCTTCTATC (SEQ ID NO: 254) | TCTATTTATTCTTCTCTTATGGCTCT ACTTCT (SEQ ID NO: 255) | TACCATTACCCGTTGCTGGTCATGCTTTG (SEQ ID NO: 252) |
| Fzd7-R3-G2 | TCTTCTTATTCTCTGATC (SEQ ID NO: 231) | CTCTCTTATTCTTCTCTATG (SEQ ID NO: 258) | TCTATTTATTCTTCTTCTTATAGCTCT ACTTCT (SEQ ID NO: 259) | GGTGCTGGTTACTACTGGTGGCATTACTACTACGTTC ATGGTGCTATG (SEQ ID NO: 260) |
| Fzd7-R3-D9 | TACTACTACTCTTCTCCGGTC (SEQ ID NO: 261) | ATCTATTATTATATATC (SEQ ID NO: 217) | TATATTTCTCCTTCTTCTCTGGCTAT ACTTCT (SEQ ID NO: 262) | GGTTACCCGGTTACTCTTGGGTTTGGTCTTTCGGTG CTTTT (SEQ ID NO: 263) |

FIGURE 1D, cont'd

| Fab ID | CDR L3 | CDR H1 | CDR H2 | CDR H3 |
|---|---|---|---|---|
| Fzd7-R3-H3 | GCTGCTTACCATTGGGCCGCGC TGTTC (SEQ ID NO: 264) | CTCTATTATTCTTCTATG (SEQ ID NO: 265) | TATATTTCTCCTTATTCTGGCTAT ACTTCT (SEQ ID NO: 266) | TACTGGGCTATG (SEQ ID NO: 267) |
| Fzd7-R2-D5 | GCTTACTACCTGATCA (SEQ ID NO: 268) | ATCCTATTATTCTTCTTCTATC (SEQ ID NO: 269) | TCTATTTATCCTTCTTCTCTGGCTAT ACTTAT (SEQ ID NO: 270) | TGGGCTCCGCATTCTTCTTCTTGGTGGTCTGTTACG GTTGGTCTGCTTGGGCTTT (SEQ ID NO: 271) |
| Fzd7-R2-H6 | TCTGTTCATTGGTACCCGTTCA (SEQ ID NO: 272) | ATCTCTTATTATTATTCTATC (SEQ ID NO: 273) | TATATTTATCCTTATTCTGGCTCT ACTTAT (SEQ ID NO: 274) | TGGGCTCATTACGGTTACTACGGTTTCTCTTACTCTG TTTACTCTGGTGGTATG (SEQ ID NO: 275) |
| Fzd7-R2-B8 | TCTTCCTATTCTCTGAT (SEQ ID NO: 276) | ATCTATTCTTCTATTATATC (SEQ ID NO: 277) | TCTATTTCTTCTTCTTCTCTGGCTAT ACTTAT (SEQ ID NO: 226) | CCGTGGTCTCATTACTCTTCTGGTGCTTACTGGCATC CGTGGTCTGGTCATGCTTTG (SEQ ID NO: 278) |
| Fzd7-R2-C8 | TACTCCGTCTCTTCTTCCTGA TCA (SEQ ID NO: 279) | ATCTATTATTCTTCTTCTATC (SEQ ID NO: 280) | TCTATTTCTTCTTCTTCTCTGGCTAT ACTTCT (SEQ ID NO: 281) | TCTTACGGTTACTACTACTACTTCTACTACTACGGTG GTATG (SEQ ID NO: 282) |
| Fzd7-R2-C11 | GGTCATTACTACCCGTACTACC TGTTCA (SEQ ID NO: 283) | ATCTATTATTCTTATATATG (SEQ ID NO: 284) | TCTATTTATTCTTATTCTGGCTAT ACTTAT (SEQ ID NO: 285) | TCTGTTTGGGGTTACCCGTACGGTATG (SEQ ID NO: 286) |
| Fzd7-R2-D2 | TCTTACTCTGGTTGGTCCGT TCA (SEQ ID NO: 287) | ATCTCTTATTCTTCTCTCTATC (SEQ ID NO: 288) | TCTATTTCTTCTTCTTCTCTAGCTAT ACTTCT (SEQ ID NO: 289) | TCTGCTTACCCGTTCTCCATTGGTCTCCGTCTTACCCGTCTCTTACG TTGGTTACTACTCTGGTTTG (SEQ ID NO: 290) |
| Fzd7-R2-D6 | TCTTACGCTTACCTCGATCA (SEQ ID NO: 291) | ATCTATTATTCTTCTTCTATG (SEQ ID NO: 202) | TCTATTTATTCTTATATTCTATGGCTAT ACTTAT (SEQ ID NO: 226) | TCTACGGTCCGGGTTCATTCTACTACTGGTACGTTGCTGCTG GGGTGGTTACGGTAHG (SEQ ID NO: 293) |
| Fzd7-R2-H11 | TACTCTGGTCCGATCA (SEQ ID NO: 294) | ATCTCTTATTATTCTTATATC (SEQ ID NO: 288) | TATATTTATTCCTTATTATAGCTAT ACTTAT (SEQ ID NO: 295) | TCTGTTTACTACCATTCTTCTGGTTGGGTTCCGCCGT GGTACTGGGGTTACGCTTTT (SEQ ID NO: 296) |
| Fzd7-R2-H4 | TACTCTTCTCCGATCA (SEQ ID NO: 297) | ATCTATTCTTCTTCTTCTATC (SEQ ID NO: 254) | TATATTTCTCCTTATTATAGCTAT ACTTAT (SEQ ID NO: 298) | TCTCATGCTTCCTCATTACTGGGGTTCTTGGTACTCTTACT CTGGTTTG (SEQ ID NO: 299) |
| Fzd7-R2-B10 | GGTTCTGTTTGGCTGTTCA (SEQ ID NO: 300) | ATCTCTTATTCTTCTCTCTATG (SEQ ID NO: 301) | TCTATTTCTTCTTCTTCTCTGGCTAT ACTTCT (SEQ ID NO: 289) | TACGGTTCCTCATTGGTCTCCGTCTTCTACCCGTTCTTACG ACTACTACTCTTACGCTTTG (SEQ ID NO: 302) |
| Fzd7-R2-G4 | GCTTACGCTTACCTGATC (SEQ ID NO: 303) | ATCTATTATTCTTATATATG (SEQ ID NO: 202) | TCTATTTATTCCTCATTCTATGGCTAT ACTTAT (SEQ ID NO: 226) | TCTGGTGCTCATTTCTACTACTGGTACGTTGCTGCTG CTATG (SEQ ID NO: 304) |
| Fzd7-R2-E9 | TCTGTTCACGTTGGTACCCGTTCA (SEQ ID NO: 305) | ATCTATTATTCTTCTTCTATC (SEQ ID NO: 240) | TCTCTTTCTTCTTCTTCTATAGCTCT ACTTAT (SEQ ID NO: 306) | GGTTACTGGTACGTTACGGTTGGGTCTTGGGTGCTTACT ACGGTTCCGGTTGGTATG (SEQ ID NO: 307) |
| Fzd7-R2-E5 | GCTTCTTGGTACCCAATCA (SEQ ID NO: 308) | ATCTATTATTCTTCTTCTATC (SEQ ID NO: 309) | TCTATTTCTTCTTCTTCTATTGGCTAT ACTTCT (SEQ ID NO: 233) | CCGGGTTACTGGGGTTACTACTGGGGTGCTGCTTACGGTA TG (SEQ ID NO: 310) |
| Fzd7-R2-F12 | GCTTACGCTTCCGTTCA (SEQ ID NO: 311) | ATCTATTATTCTTATATATG (SEQ ID NO: 206) | TCTATTTATTATTCTTATTCTGGCTAT ACTTAT (SEQ ID NO: 292) | TCTTCCTCTTCGGTCATTGGTTCATGCTGGTTTCGGTGTG CTATG (SEQ ID NO: 312) |
| Fzd7-R2-D10 | TACTGGGCTTCCGATCA (SEQ ID NO: 313) | ATCTATTATTCTTCTTCTATG (SEQ ID NO: 314) | TCTATTTATTCTTATTCTGGCTAT ACTTCT (SEQ ID NO: 315) | TACGCTTCTTACGTTGGTTACTACCCGTGGGGCTTTG (SEQ ID NO: 316) |
| Fzd7-R2-B5 | GGTTCCGCTTCTGTCTGTCTGA TCA (SEQ ID NO: 317) | ATCCTATTATTCTTCTATG (SEQ ID NO: 202) | TCTATTTATTCTTATGGCTAT ACTTCT (SEQ ID NO: 233) | TTTCTACTTCTTCTACTTCTCTGGTACCCGCCGG CTGGTTTG (SEQ ID NO: 318) |

FIGURE 1D, cont'd

| Fab ID | CDR L3 | CDR H1 | CDR H2 | CDR H3 |
|---|---|---|---|---|
| Fzd7-R2-A4 | GCTTACTGGTGGGTTGGTCCGA TCA (SEQ ID NO: 319) | CTCTCTTATTCTTCTTCTATC (SEQ ID NO: 320) | TATATTCTTCTTCTTCTTATGGCTAT ACTTCT (SEQ ID NO: 321) | TTCTTCTGCTTACTGGGCTTGGCATGGTTTG (SEQ ID NO: 322) |
| Fzd7-R2-E8 | GTTTCGGTGGTGGTGGTGGTCTGA TCA (SEQ ID NO: 323) | ATCTATTCTTCTTCTTATATC (SEQ ID NO: 324) | TATATTTATTCTTATTCTTCTTGGCTAT ACTTAT (SEQ ID NO: 325) | TGGTACCATCCGTACTGGTACGCTTCTGCTATT (SEQ ID NO: 326) |
| Fzd7-R3-H10 | TGGGCTTACGGTCCGGTTCA (SEQ ID NO: 327) | ATCTATTATTATTCTTCTATG (SEQ ID NO: 328) | TCTATTTATTCTTCTTCTTATAGCTAT ACTTCT (SEQ ID NO: 292) | TCTTCTCCGGGTGCTGATTACGGTTTG (SEQ ID NO: 329) |
| Fzd7-R2-D7 | TCTACTGTTACTACCTGATCA (SEQ ID NO: 330) | ATCTATTATTATTCTTCTATG (SEQ ID NO: 240) | TATATTTATTCCTTATTCTAGCTAT ACTTCT (SEQ ID NO: 331) | TACCATGGTTTCTACGGTATG (SEQ ID NO: 332) |
| Fzd7-R2-C10 | TCTGCTTGGTGGGCTTCTCGT TCA (SEQ ID NO: 333) | ATCTCTTATTCTTCTTATATC (SEQ ID NO: 334) | TCTATTTATCCTTATTCTAGCTAT ACTTAT (SEQ ID NO: 335) | TACTCTGGTTTCGCTATG (SEQ ID NO: 336) |
| Fzd7-R2-E11 | TACTCTTACGGTTACGCTTCTGT TCA (SEQ ID NO: 337) | CTCTCTTATTCTTCTTCTTGT (SEQ ID NO: 338) | TCTATTTATCCTTATTATAGCTAT ACTTAT (SEQ ID NO: 339) | TACTGGTCTGGTTTT (SEQ ID NO: 340) |
| Fzd7-R2-F9 | TGGGTACTACGGTTGGCATCGA TCA (SEQ ID NO: 341) | ATCTCTTATTCTTCTTCTATC (SEQ ID NO: 342) | TCTATTTATCCTTCTTATGGCTAT ACTTAT (SEQ ID NO: 244) | TACGGTTACTTCGGTATG (SEQ ID NO: 343) |
| Fzd7-R2-E3 | TCTTACTCTGCTTCTCTGTTCA (SEQ ID NO: 344) | CTCTATTATTCTTATCTTATC (SEQ ID NO: 345) | TCTATTTCTCCTTCTTATAGCTCT ACTTCT (SEQ ID NO: 346) | GTTTCTTACTGGGGTGCTGGTATG (SEQ ID NO: 347) |
| Fzd7-R2-A9 | TGGGTTCTTACGTTGCTCTGT TCA (SEQ ID NO: 348) | ATCTCTTATTCTTCTTCTATC (SEQ ID NO: 349) | TCTATTTATCCTTATTATGGCTCT ACTTAT (SEQ ID NO: 350) | GTTGGTCCGGGTTCTTACGGTGGTTTG (SEQ ID NO: 351) |
| Fzd7-R2-E7 | TACTACTCTTACTCTGTTGGC TGATCA (SEQ ID NO: 352) | ATCTCTTATTATTATATG (SEQ ID NO: 353) | TATATTTCTCCTTCTTCTTCTAGCTAT ACTTCT (SEQ ID NO: 354) | TGGTACGGTTGGGCTTTG (SEQ ID NO: 355) |
| Fzd7-R2-F1 | TCTTACTACCCGATCA (SEQ ID NO: 356) | CTCTCTTATTATATTCTTCTATC (SEQ ID NO: 357) | TCTATTTATCCTTCTCCTGGCTAT ACTTCT (SEQ ID NO: 248) | TTCTCTGGTTGGGCTTTG (SEQ ID NO: 358) |
| Fzd7-R2-G1 | TGGGGTTACGGTGTTGCTCTGATCA (SEQ ID NO: 359) | ATCTATTCTTCTTCTTATATC (SEQ ID NO: 342) | TCTATTTATCCTTCTCCTGGCTAT ACTTCT (SEQ ID NO: 360) | CATGGTTGGTACGGTTTG (SEQ ID NO: 361) |
| Fzd7-R2-G6 | TACTCTCTCTGTTCA (SEQ ID NO: 362) | ATCTATTATTATTCTTCTATG (SEQ ID NO: 328) | TATATTTATTCTTCTTCTTATGGCTAT ACTTAT (SEQ ID NO: 363) | GGTTACTTCTACTCTGGGGTGGTATG (SEQ ID NO: 364) |
| Fzd7-R2-G12 | TGGGGTTACGGTGCTCTGATCA (SEQ ID NO: 359) | ATCTATTATTCTTATTCTTATC (SEQ ID NO: 342) | TCTATTTATCCTTCTCCTGGCTAT ACTTCT (SEQ ID NO: 360) | CATGGTTGGTACGGTTTG (SEQ ID NO: 361) |
| Fzd7-R2-H1 | TACTGGTACGGTGTTGCTCCGA TCA (SEQ ID NO: 365) | ATCTATTATTCTTCTTCTATC (SEQ ID NO: 288) | TATATTTATTCCTTCTCCTGGCTCT ACTTCT (SEQ ID NO: 366) | GCTTCTTCTTGGTACGCTTTG (SEQ ID NO: 367) |
| Fzd7-R2-B11 | TACTTCTACTCTTCTTCTTACTCTC CGATCA (SEQ ID NO: 368) | ATCTCTTATTCTTCTTATATG (SEQ ID NO: 206) | TATATTTATTCTTCTTATAGCTCT ACTTAT (SEQ ID NO: 369) | GCTTCTTGGGCTTTG (SEQ ID NO: 370) |
| Fzd7-R2-A7 | TACCATTACGGTTACTACCCGT TCA (SEQ ID NO: 371) | CTCTTCTTATTCTTCTTATATC (SEQ ID NO: 372) | TATATTTATTCTTCTTATGGCTCT ACTTAT (SEQ ID NO: 366) | GCTTCTTGGGTGGGCTATT (SEQ ID NO: 373) |

FIGURE 1D, cont'd

| Fab ID | CDR L3 | CDR H1 | CDR H2 | CDR H3 |
|---|---|---|---|---|
| Fzd7-R2-H8 | TCTTTCTACTGGGGTTACCCGCCGTTCA (SEQ ID NO: 374) | ATCTATTCTTCTTCTATC (SEQ ID NO: 254) | TCTATTATTCTTATTATGGCTAT ACTTAT (SEQ ID NO: 375) | TGGTACGCTTTT (SEQ ID NO: 376) |
| Fzd7-R2-A1 | TACTACCATCCGATCA (SEQ ID NO: 377) | ATCTCTTCTTATTATATC (SEQ ID NO: 277) | TCTATTTATCCTTATTATAGCTCT ACTTAT (SEQ ID NO: 378) | GTTTGGTACGGTTGCTATG (SEQ ID NO: 379) |
| Fzd7-R2-A2 | GGTTCTTACTCTTACCCGTTCA (SEQ ID NO: 380) | ATCTCTTATTCTTATTCTATG (SEQ ID NO: 240) | TCTATTTATCCTTATTCTGGCTAT ACTTAT (SEQ ID NO: 381) | TGGCATGGTTACGGTATT (SEQ ID NO: 382) |
| Fzd7-R2-A12 | GGTCCGGCTTACTCTTACCTGT TCA (SEQ ID NO: 383) | ATCTATTCTTATTCTTATG (SEQ ID NO: 206) | TTATATTATCCTTATTATGGCTAT ACTTAT (SEQ ID NO: 229) | GGTTACTACGGTTTG (SEQ ID NO: 384) |
| Fzd7-R2-B2 | GCTTACGCTTACCTGATC (SEQ ID NO: 303) | ATCTCTTATTCTTCTTCTATG (SEQ ID NO: 202) | TCTATTTCTTCTCTCTTATGGCTAT ACTTAT (SEQ ID NO: 226) | TCTGGGTGGTCATTCTACTACTGGTACGTTGCTGCTG CTATG (SEQ ID NO: 304) |
| Fzd7-R2-C12 | TCTTTCTTATTCTCTGATC (SEQ ID NO: 276) | CTCTCTTATTCTTATATG (SEQ ID NO: 232) | TCTATTTATTCTTCTTATGGCTAT ACTTCT (SEQ ID NO: 233) | TACTACGGTTGGGCTTACTACTACTCTTACTTCCCGG CTTGGGCTGGTGGGTGGTATT (SEQ ID NO: 234) |
| Fzd7-R2-A3 | GCTTTTCGGTTGGCCGCTGATCA (SEQ ID NO: 385) | ATCTATTCTTATTCTATATC (SEQ ID NO: 217) | TATATTATCCTTATTCTCGGCTCT ACTTCT (SEQ ID NO: 386) | GCTGGTTGGTACGTTTACGGTTCCGTACGGTTTT (SEQ ID NO: 387) |
| Fzd7-R2-B12 | TCTTTCTTATTCTCTGATC (SEQ ID NO: 276) | CTCTCTTATTCTTATATG (SEQ ID NO: 232) | TCTATTTCTTCTCTCTTATGGCTAT ACTTAT (SEQ ID NO: 226) | GCTGCTGGTCCGTACTGGTACTCTTACTGGTACTCTG CTATG (SEQ ID NO: 388) |
| Fzd7-R2-C1 | TACGGTCATTACCTGATCA (SEQ ID NO: 389) | CTCTATTCTTATTCTATG (SEQ ID NO: 390) | TCTATTTCTTCTTATTATGGCTCT ACTTAT (SEQ ID NO: 391) | GCTCATGGTTCTTCTCCGGTTGGTACTACGCTCCGT ACGCTGGTGGTGGTTTG (SEQ ID NO: 257) |

FIGURE 2A

| Clone ID | Selection round ID | Elution 1 mg/ml | ug | Elution 2 mg/ml | ug | Total yield ug |
|---|---|---|---|---|---|---|
| D5 | 2 | 0.16 | 40.3 | 0.12 | 29.5 | 69.8 |
| B8 | 2 | 0.36 | 91.0 | 0.17 | 41.5 | 132.5 |
| C8 | 2 | 0.17 | 41.5 | 0.12 | 29.5 | 71.0 |
| C11 | 2 | 0.25 | 63.5 | 0.14 | 34.3 | 97.8 |
| D2 | 2 | 0.42 | 105.5 | 0.23 | 57.8 | 163.3 |
| D6 | 2 | 0.19 | 47.8 | 0.17 | 43.0 | 90.8 |
| H11 | 2 | 0.29 | 71.5 | 0.12 | 31.0 | 102.5 |
| H4 | 2 | 0.01 | 2.8 | 0.01 | 2.5 | 5.3 |
| B10 | 2 | 0.32 | 79.3 | 0.15 | 37.8 | 117.0 |
| G4 | 2 | 0.28 | 70.5 | 0.17 | 43.3 | 113.8 |
| E9 | 2 | 0.08 | 19.0 | 0.06 | 14.5 | 33.5 |
| E5 | 2 | 0.35 | 87.3 | 0.15 | 38.3 | 125.5 |
| F12 | 2 | 0.35 | 87.8 | 0.20 | 49.0 | 136.8 |
| D10 | 2 | 0.28 | 70.0 | 0.16 | 40.3 | 110.3 |
| E8 | 2 | 0.15 | 38.0 | 0.08 | 20.3 | 58.3 |
| D7 | 2 | 0.11 | 27.3 | 0.06 | 16.0 | 43.3 |
| C10 | 2 | 0.37 | 92.0 | 0.22 | 55.8 | 147.8 |
| E11 | 2 | 0.32 | 79.0 | 0.17 | 42.8 | 121.8 |
| F9 | 2 | 0.42 | 106.0 | 0.24 | 59.0 | 165.0 |
| E3 | 2 | 0.38 | 95.5 | 0.16 | 41.0 | 136.5 |
| E7 | 2 | 0.04 | 9.3 | 0.04 | 10.0 | 19.3 |
| G1 | 2 | 0.32 | 79.3 | 0.23 | 58.3 | 137.5 |
| G6 | 2 | 0.09 | 21.3 | 0.10 | 24.0 | 45.3 |
| H10 | 3 | 0.19 | 47.0 | 0.18 | 44.3 | 91.3 |
| G12 | 2 | 0.45 | 111.5 | 0.30 | 74.5 | 186.0 |
| H1 | 2 | 0.35 | 87.3 | 0.21 | 52.8 | 140.0 |
| B11 | 2 | 0.24 | 59.8 | 0.12 | 30.8 | 90.5 |

FIGURE 2A, cont'd

| Clone ID | Selection round ID | Elution 1 mg/ml | Elution 1 ug | Elution 2 mg/ml | Elution 2 ug | Total yield ug |
|---|---|---|---|---|---|---|
| A7 | 2 | 0.36 | 89.5 | 0.15 | 37.3 | 126.8 |
| H8 | 2 | 0.26 | 64.3 | 0.20 | 49.3 | 113.5 |
| A1 | 2 | 0.50 | 125.5 | 0.32 | 80.3 | 205.8 |
| A2 | 2 | 0.46 | 116.0 | 0.28 | 68.8 | 184.8 |
| A12 | 2 | 0.32 | 80.0 | 0.18 | 44.3 | 124.3 |
| B2 | 2 | 0.45 | 113.5 | 0.34 | 85.8 | 199.3 |
| C12 | 2 | 0.24 | 59.0 | 0.17 | 42.0 | 101.0 |
| B12 | 2 | 0.35 | 88.5 | 0.26 | 65.3 | 153.8 |
| C1 | 2 | 0.38 | 93.8 | 0.27 | 67.8 | 161.5 |
| B7 | 3 | 0.20 | 50.3 | 0.13 | 31.5 | 81.8 |
| D11 | 3 | 0.35 | 87.5 | 0.21 | 53.0 | 140.5 |
| F3 | 3 | 0.34 | 84.5 | 0.12 | 29.5 | 114.0 |
| E9 | 3 | 0.31 | 76.8 | 0.17 | 41.8 | 118.5 |
| B10 | 3 | 0.28 | 70.0 | 0.14 | 35.3 | 105.3 |
| G7 | 3 | 0.19 | 46.5 | 0.13 | 31.8 | 78.3 |
| C3 | 3 | 0.28 | 69.3 | 0.18 | 45.3 | 114.5 |
| A10 | 3 | 0.10 | 24.5 | 0.04 | 10.0 | 34.5 |
| B2 | 3 | 0.24 | 59.8 | 0.11 | 28.3 | 88.0 |
| B9 | 3 | 0.25 | 63.5 | 0.10 | 25.0 | 88.5 |
| E4 | 3 | 0.52 | 129.5 | 0.36 | 90.0 | 219.5 |
| G2 | 3 | 0.54 | 135.5 | 0.27 | 67.8 | 203.3 |
| D9 | 3 | 0.31 | 76.3 | 0.18 | 44.8 | 121.0 |
| G9 | 3 | 0.33 | 83.5 | 0.16 | 38.8 | 122.3 |
| H3 | 3 | 0.34 | 86.0 | 0.25 | 62.0 | 148.0 |

FIGURE 2B

| Clone ID | Selection round ID | OD 450 | | | | | |
|---|---|---|---|---|---|---|---|
| | | 10ug/ml (200nM) Fab | | | 1ug/ml (20nM) Fab | | |
| | | Fzd7-Fc | Fc | ratio | Fzd7-Fc | Fc | ratio |
| D5 | 2 | 3.21 | 0.17 | 19.3 | 2.65 | 0.06 | 44.2 |
| B8 | 2 | 1.16 | 0.05 | 21.4 | 0.24 | 0.05 | 4.5 |
| C8 | 2 | 1.36 | 0.09 | 15.1 | 0.55 | 0.05 | 10.9 |
| C11 | 2 | 1.09 | 0.06 | 19.2 | 0.24 | 0.07 | 3.5 |
| D2 | 2 | 1.60 | 0.05 | 30.8 | 0.50 | 0.06 | 8.0 |
| D6 | 2 | 3.09 | 0.12 | 25.8 | 2.98 | 0.06 | 50.5 |
| H11 | 2 | 3.23 | 0.06 | 57.7 | 3.18 | 0.05 | 61.1 |
| H4 | 2 | n.t | n.t | n.t | n.t | n.t | n.t |
| B10 | 2 | 2.99 | 0.06 | 50.6 | 2.82 | 0.06 | 49.5 |
| G4 | 2 | 3.17 | 0.07 | 48.1 | 3.15 | 0.05 | 60.6 |
| E9 | 2 | 3.22 | 0.07 | 46.7 | 3.15 | 0.05 | 63.0 |
| E5 | 2 | 3.17 | 0.06 | 54.7 | 3.17 | 0.07 | 46.0 |
| F12 | 2 | 3.11 | 0.06 | 51.0 | 1.05 | 0.08 | 13.5 |
| D10 | 2 | 3.19 | 0.07 | 43.8 | 3.01 | 0.05 | 60.1 |
| E8 | 2 | 3.20 | 0.09 | 36.0 | 3.16 | 0.05 | 60.7 |
| D7 | 2 | 3.18 | 0.07 | 43.6 | 3.22 | 0.07 | 48.0 |
| C10 | 2 | 2.05 | 0.06 | 37.2 | 0.37 | 0.07 | 5.5 |
| E11 | 2 | 3.22 | 0.06 | 56.5 | 3.24 | 0.05 | 60.0 |
| F9 | 2 | 3.16 | 0.06 | 54.4 | 3.11 | 0.06 | 53.5 |
| E3 | 2 | 2.19 | 0.07 | 32.7 | 0.28 | 0.05 | 5.2 |
| E7 | 2 | 0.08 | 0.09 | 1.0 | 0.07 | 0.06 | 1.1 |
| G1 | 2 | 3.18 | 0.05 | 58.9 | 3.17 | 0.05 | 62.1 |
| G6 | 2 | 3.21 | 0.06 | 57.2 | 3.23 | 0.05 | 64.6 |
| H10 | 3 | 3.22 | 0.06 | 57.6 | 3.19 | 0.05 | 61.3 |
| G12 | 2 | 3.19 | 0.14 | 23.3 | 3.13 | 0.06 | 56.9 |

FIGURE 2B, cont'd

|  |  | OD 450 | | | | | |
|---|---|---|---|---|---|---|---|
|  | Selection | 10ug/ml (200nM) Fab | | | 1ug/ml (20nM) Fab | | |
| Clone ID | round ID | Fzd7-Fc | Fc | ratio | Fzd7-Fc | Fc | ratio |
| H1 | 2 | 3.19 | 0.06 | 53.1 | 3.20 | 0.05 | 62.7 |
| B11 | 2 | 3.20 | 0.08 | 40.0 | 3.15 | 0.05 | 59.3 |
| A7 | 2 | 3.22 | 0.07 | 46.6 | 3.19 | 0.07 | 43.1 |
| H8 | 2 | 2.70 | 0.08 | 36.0 | 0.78 | 0.06 | 13.7 |
| A1 | 2 | 3.23 | 0.07 | 44.2 | 3.22 | 0.05 | 59.7 |
| A2 | 2 | 1.05 | 0.05 | 19.8 | 0.14 | 0.09 | 1.6 |
| A12 | 2 | 0.56 | 0.07 | 8.3 | 0.52 | 0.05 | 9.8 |
| B2 | 2 | 3.18 | 0.13 | 24.1 | 3.19 | 0.06 | 53.2 |
| C12 | 2 | 3.15 | 0.07 | 43.2 | 2.87 | 0.05 | 54.2 |
| B12 | 2 | 0.91 | 0.06 | 15.1 | 0.16 | 0.05 | 3.2 |
| C1 | 2 | 3.19 | 0.14 | 22.6 | 3.15 | 0.06 | 53.4 |
| B7 | 3 | 3.06 | 0.07 | 42.0 | 2.12 | 0.06 | 36.5 |
| D11 | 3 | 2.79 | 0.15 | 18.7 | 1.42 | 0.06 | 24.1 |
| F3 | 3 | 2.97 | 0.07 | 43.7 | 2.35 | 0.06 | 37.8 |
| E9 | 3 | 3.20 | 0.10 | 33.0 | 3.09 | 0.07 | 47.5 |
| B10 | 3 | 3.24 | 0.06 | 52.2 | 3.22 | 0.06 | 56.5 |
| G7 | 3 | 2.98 | 0.13 | 22.6 | 1.90 | 0.06 | 31.7 |
| C3 | 3 | 2.02 | 0.06 | 36.8 | 1.72 | 0.05 | 33.6 |
| A10 | 3 | 1.74 | 0.05 | 34.8 | 0.08 | 0.05 | 1.5 |
| B2 | 3 | 3.18 | 0.10 | 33.5 | 2.92 | 0.06 | 52.2 |
| B9 | 3 | 3.26 | 0.06 | 56.2 | 3.22 | 0.05 | 63.2 |
| E4 | 3 | 3.27 | 0.08 | 41.9 | 3.24 | 0.05 | 61.1 |
| G2 | 3 | 3.24 | 0.07 | 47.6 | 3.20 | 0.05 | 64.0 |
| D9 | 3 | 3.12 | 0.09 | 35.0 | 3.05 | 0.06 | 54.5 |
| G9 | 3 | 3.21 | 0.16 | 19.6 | 3.12 | 0.06 | 48.8 |
| H3 | 3 | 3.21 | 0.10 | 31.2 | 3.20 | 0.05 | 61.5 |

FIGURE 3

| Clone ID | Selection round ID | % population within the positive gate | |
|---|---|---|---|
| | | Over-expression line (MDA MB 231) | MDA MB 231 |
| D5 | 2 | 88.1 | 3.9 |
| B8 | 2 | 80.9 | 2.8 |
| C8 | 2 | 83.5 | 2.7 |
| C11 | 2 | 42.0 | 1.0 |
| D2 | 2 | 75.2 | 0.8 |
| D6 | 2 | 84.3 | 35.3 |
| H11 | 2 | 92.0 | 99.1 |
| H4 | 2 | n.t | n.t. |
| B10 | 2 | 88.4 | 35.0 |
| G4 | 2 | 85.4 | 5.1 |
| E9 | 2 | 90.7 | 99.4 |
| E5 | 2 | 86.2 | 6.3 |
| F12 | 2 | 59.9 | 1.4 |
| D10 | 2 | 91.7 | 96.4 |
| E8 | 2 | 89.2 | 77.7 |
| D7 | 2 | 75.7 | 1.7 |
| C10 | 2 | 50.5 | 0.9 |
| E11 | 2 | 94.2 | 99.2 |
| F9 | 2 | 88.3 | 50.3 |
| E3 | 2 | 3.0 | 0.8 |
| E7 | 2 | 0.1 | 0.2 |
| G1 | 2 | 83.4 | 28.6 |
| G6 | 2 | 93.4 | 99.4 |
| H10 | 3 | 93.2 | 99.0 |
| G12 | 2 | 83.8 | 33.3 |

FIGURE 3, cont'd

| Clone ID | Selection round ID | % population within the positive gate | |
|---|---|---|---|
| | | Over-expression line (MDA MB 231) | MDA MB 231 |
| H1 | 2 | 94.7 | 99.0 |
| B11 | 2 | 91.2 | 97.2 |
| A7 | 2 | 92.7 | 96.3 |
| H8 | 2 | 79.6 | 1.1 |
| A1 | 2 | 93.1 | 98.6 |
| A2 | 2 | 0.1 | 1.5 |
| A12 | 2 | 0.1 | 0.8 |
| B2 | 2 | 86.8 | 7.1 |
| C12 | 2 | 86.9 | 11.9 |
| B12 | 2 | 74.6 | 0.9 |
| C1 | 2 | 87.3 | 66.5 |
| B7 | 3 | 80.1 | 0.7 |
| D11 | 3 | 81.0 | 1.2 |
| F3 | 3 | 82.5 | 1.0 |
| E9 | 3 | 87.1 | 96.6 |
| B10 | 3 | 93.7 | 98.2 |
| G7 | 3 | 84.2 | 15.3 |
| C3 | 3 | 2.2 | 0.7 |
| A10 | 3 | 54.3 | 44.5 |
| B2 | 3 | 86.2 | 15.9 |
| B9 | 3 | 91.5 | 46.7 |
| E4 | 3 | 93.4 | 98.8 |
| G2 | 3 | 94.1 | 99.2 |
| D9 | 3 | 80.9 | 0.7 |
| G9 | 3 | 84.7 | 6.1 |
| H3 | 3 | 92.2 | 99.0 |

FIGURE 4A

| clone ID | selection round ID | human Fzd1-Fc | mouse Fzd2-Fc | human Fzd5-Fc | human Fzd8-Fc | human Fzd7-Fc |
|---|---|---|---|---|---|---|
| H11 | 2 | + | + | - | - | + |
| E9 | 2 | + | + | + | + | + |
| D10 | 2 | + | + | + | - | + |
| E8 | 2 | - | + | - | - | + |
| E11 | 2 | + | + | + | - | + |
| G6 | 2 | + | + | + | + | + |
| H10 | 3 | + | + | + | + | + |
| H1 | 2 | + | + | + | + | + |
| B11 | 2 | + | + | - | - | + |
| A7 | 2 | + | + | - | - | + |
| A1 | 2 | + | + | - | - | + |
| E9 | 3 | + | + | - | - | + |
| B10 | 3 | + | + | + | + | + |
| E4 | 3 | + | + | + | + | + |
| G2 | 3 | + | + | + | + | + |
| H3 | 3 | + | + | + | + | + |
| % Amino acid identify with FZD7 CRD | | 82 | 94 | 52 | 51 | 100 |

+, binding detected; -, binding not detected

FIGURE 4B

| | FZD CRD | | | | | | | | | |
|---|---|---|---|---|---|---|---|---|---|---|
| | 1 | 2 | 3 | 4 | 5 | 6 | 7 | 8 | 9 | 10 |
| % sequence ID with Fzd7 CRD | 82 | 92 | 37 | 38 | 52 | 33 | 100 | 44 | 35 | 42 |
| A1 | + | + | - | - | + | - | + | + | - | - |
| D10 | + | + | - | - | + | - | + | + | - | - |
| E4 | + | + | - | - | + | - | + | + | - | - |
| E8 | - | + | - | - | - | - | + | - | - | - |
| G2 | + | + | - | + | + | - | + | + | - | - |
| G6 | + | + | - | - | + | - | + | + | - | - |
| H1 | + | + | - | - | - | - | + | + | - | - |
| H3 | + | + | - | - | + | - | + | + | - | - |
| H10 | + | + | - | - | + | - | + | + | - | - |
| Negative control | - | - | - | - | - | - | - | - | - | - |

FIGURE 5

(% of Fab phage in presence of 750 nM Fab) Blocking Fab

| Detected phage-Fab | D10 | G6 | H10 | H1 | A1 | E4 | H3 | G2 |
|---|---|---|---|---|---|---|---|---|
| D10 | 8.8 | 4.8 | 6.8 | 4.7 | 5.0 | 6.1 | 5.2 | 21.8 |
| G6 | 50.9 | 6.4 | 20.1 | 10.4 | 8.2 | 7.4 | 25.5 | 43.8 |
| H10 | 28.1 | 4.5 | 7.4 | 4.3 | 5.2 | 3.2 | 15.0 | 21.7 |
| H1 | 67.3 | 17.2 | 53.5 | 8.5 | 13.7 | 21.9 | 59.3 | 62.9 |
| A1 | 49.1 | 5.8 | 21.8 | 4.5 | 4.2 | 6.5 | 34.4 | 48.8 |
| E4 | 54.1 | 7.0 | 20.9 | 12.0 | 7.3 | 5.1 | 26.7 | 38.8 |
| H3 | 29.1 | 9.6 | 27.7 | 18.3 | 15.1 | 10.5 | 16.2 | 51.8 |
| G2 | 26.4 | 4.7 | 7.4 | 4.5 | 4.7 | 4.6 | 8.2 | 14.4 |
| E8 | 14.5 | 8.0 | 7.1 | 6.7 | 6.5 | 5.9 | 11.8 | 13.2 |

FIGURE 6A

| Clone ID | selection round ID | ka (M⁻¹s⁻¹) | kd (s⁻¹) | KD M | nM | statistics Rmax | Chi2 | Chi2/Rmax*100 | Ligand Density (RU) |
|---|---|---|---|---|---|---|---|---|---|
| D10 | 2 | 9.77E+04 | 8.81E-04 | 9.02E-09 | 9.02 | 43.48 | 2.98 | 6.85 | 180 |
| E8 | 2 | 2.31E+05 | 3.91E-04 | 1.69E-09 | 1.69 | 41.65 | 4.05 | 9.72 | 180 |
| G6 | 2 | 2.01E+06 | 1.10E-03 | 5.45E-10 | 0.55 | 58.47 | 8.72 | 14.91 | 180 |
| H10 | 3 | 5.33E+05 | 5.48E-04 | 1.03E-09 | 1.03 | 48.39 | 3.34 | 6.90 | 180 |
| H1 | 2 | 8.52E+05 | 4.57E-04 | 5.37E-10 | 0.54 | 54.56 | 3.43 | 6.29 | 180 |
| A1 | 2 | 4.76E+05 | 9.94E-04 | 2.09E-09 | 2.09 | 52.08 | 5.09 | 10.03 | 180 |
| E4 | 3 | 1.90E+06 | 8.03E-04 | 4.22E-10 | 0.42 | 55.77 | 5.1 | 9.14 | 180 |
| G2 | 3 | 1.38E+05 | 3.12E-04 | 2.27E-09 | 2.27 | 42.61 | 2.89 | 6.78 | 180 |
| H3 | 3 | 1.05E+06 | 9.78E-04 | 9.31E-10 | 0.93 | 56.79 | 5.71 | 10.05 | 180 |

FIGURE 7

| Fab ID | Fab | | | | | | IgG |
| --- | --- | --- | --- | --- | --- | --- | --- |
| | FZD1 ECD | mFZD2 ECD | FZD4 ECD | FZD5 ECD | FZD8 ECD | FZD7 ECD | FZD7 ECD |
| A1 | 1.07 | 1.75 | 13.3 | 15.8 | 9.31 | 2.09 | 0.24 |
| D10 | 10 | 5.13 | x | 2.9 | 3.21 | 9.02 | 1.45 |
| E4 | 0.33 | 0.65 | x | 1.43 | 0.88 | 0.42 | 0.49 |
| E8 | x | 5.4 | x | 7.46 | x | 1.69 | x |
| G2 | 2.35 | 1.74 | x | 2.51 | 2.49 | 2.27 | 0.33 |
| G6 | 0.87 | 0.96 | 5.46 | 4.63 | 3.57 | 0.55 | 0.3 |
| H1 | 0.64 | 0.57 | x | x | x | 0.54 | 0.57 |
| H3 | 2.26 | 1.22 | x | 0.16 | 0.2 | 0.93 | 0.46 |
| H10 | 3.67 | 0.95 | x | 3.06 | 2.5 | 1.03 | 0.67 |

X, binding to the FZD ECD not detected by SPR

FZD7 H10- IgG (mAb # 111)
FZD7 G2-IgG (mAb #140)

FZD7 H10-IgG (mAb #111)
FZD7 G2-IgG (mAb #140)

| Proliferation (%) | 0ug/ml | 1 ug/ml | 2ug/ml | 5 ug/ml | 10ug/ml | 50ug/ml |
|---|---|---|---|---|---|---|
| Human Gamma Globulin | 100.00 | 92.13 | 92.07 | 92.35 | 101.60 | 103.29 |
| FZD7 A1-IgG (IgG #105) | 100.00 | 81.92 | 80.06 | 77.78 | 75.25 | 85.61 |
| FZD7 E4-IgG (IgG #107) | 100.00 | 72.75 | 65.39 | 63.01 | 65.49 | 48.17 |
| FZD7 H10-IgG (IgG #111) | 100.00 | 55.74 | 53.05 | 46.89 | 38.46 | 43.96 |

| Proliferation (%) | 0ug/ml | 1 ug/ml | 2ug/ml | 5 ug/ml | 10ug/ml | 50ug/ml |
|---|---|---|---|---|---|---|
| Human Gamma Globulin | 100.00 | 100.27 | 95.90 | 97.74 | 94.23 | 98.69 |
| FZD7 H1-IgG (IgG # 112) | 100.00 | 81.64 | 84.10 | 77.29 | 93.96 | 78.37 |
| FZD7 G2-IgG (IgG # 140) | 100.00 | 47.79 | 42.74 | 40.37 | 36.99 | 34.47 |
| 18R5-IgG | 100.00 | 57.56 | 60.31 | 39.57 | 46.68 | 39.39 |

| Antibody | Mice/Group | % Tumor Growth Inhibition | T-test |
|---|---|---|---|
| Control Buffer | 9 | 0.0 | |
| Ab#111 (mAb H10) 5 mg/kg | 9 | 36.3 | 0.0320 |
| Ab#111 (mAb H10) 20 mg/kg | 9 | 56.8 | 0.0021 |
| Ab#111 (mAb H10) 50 mg/kg | 9 | 65.8 | 0.0002 |
| Ab#112 (mAb H01) 5 mg/kg | 9 | 35.4 | 0.0376 |
| Ab#112 (mAb H01) 20 mg/kg | 9 | 37.0 | 0.0336 |
| Ab#112 (mAb H01) 50mg/kg | 9 | 44.7 | 0.0105 |
| DPBS | 8 | 3.7 | 0.8074 |

US 10,689,442 B2

ANTIBODIES AGAINST FRIZZLED RECEPTOR

RELATED APPLICATIONS

This application is a continuation of U.S. patent application Ser. No. 14/911,983, filed on Feb. 12, 2016, which is a national stage application filed under 35 U.S.C. § 371, of International Application No. PCT/US2014/051070, filed Aug. 14, 2014, which claims the benefit of U.S. Provisional Application No. 61/865,668, filed Aug. 14, 2013, the contents of which are herein incorporated by reference in their entirety.

INCORPORATION-BY-REFERENCE OF SEQUENCE LISTING

The contents of the file named "UTOR-002_C01US Sequence Listing_ST25.txt", which was created on Aug. 1, 2018 and is 83.3 KB in size, are hereby incorporated by reference in their entirety.

FIELD OF THE INVENTION

This invention relates generally to the generation of antibodies, e.g., monoclonal antibodies, that recognize one or more Frizzled receptors, and to methods of using these anti-Frizzled antibodies as therapeutics.

BACKGROUND OF THE INVENTION

Frizzled receptors belong to a class of G protein-coupled receptors. Aberrant Frizzled receptor expression or activity has been implicated in various disorders. Accordingly, there exists a need for therapies that target and inhibit one or more Frizzled receptors.

SUMMARY OF THE INVENTION

The present invention provides high affinity antibodies such as monoclonal antibodies which recognize a Frizzled receptor or a combination of Frizzled receptors, for example, a human Frizzled receptor or a combination of human Frizzled receptors. In some embodiments, the antibodies bind to the cysteine rich domain (CRD) of a Frizzled receptor or the CRDs of a combination of Frizzled receptors. These antibodies are capable of modulating, e.g., blocking, inhibiting, reducing, antagonizing, neutralizing or otherwise interfering with one or more biological activities of a Frizzled receptor or a combination of Frizzled receptors, for example, binding to a Wnt protein ligand, which activates a Wnt signaling pathway.

These antibodies and antigen-binding fragments thereof bind to one or more Frizzled receptors expressed on the cell surface. For example, these antibodies bind to one or more Frizzled receptors on various cancer cell lines and inhibit the growth of cancer cells of multiple tissue origins. These antibodies also bind to one or more Frizzled receptors on various cancer cell lines and inhibit the growth of cancer stem cells. Thus, the antibodies and antigen-binding fragments thereof are useful for treating, preventing, delaying the progression of or otherwise ameliorating a symptom of cancer, as well as other diseases where Frizzled receptor expression and/or activity is dysregulated such as, by way of non-limiting example, bone diseases, including, e.g., osteoporosis, osteoarthritis (OA), and rheumatoid arthritis (RA). In some embodiments, the antibodies and antigen-binding fragments thereof are useful for treating a cancer, such as, by way of non-limiting example, breast cancer, including triple negative breast cancer, lung cancer, colon cancer, ovarian cancer, pancreatic cancer, gastrointestinal (GI) cancer, neuroblastoma, renal cancer, prostate cancer, melanoma, leukemia, and/or Wilm's tumor. In some embodiments, the antibodies and antigen-binding fragments thereof are useful for treating a cancer that is associated with cancer stem cells. In some embodiments, these anti-Frizzled receptor antibodies and fragments of the invention are useful in modulating, e.g., blocking, inhibiting, reducing, antagonizing, neutralizing or otherwise interfering with the survival, migration and/or invasion, e.g., metastasis, of a cancer cell. In some embodiments, these anti-Frizzled receptor antibodies and fragments of the invention are useful in modulating, e.g., blocking, inhibiting, reducing, antagonizing, neutralizing or otherwise interfering with the survival, migration and/or invasion, e.g., metastasis, of a breast cancer cell, a lung cancer cell, a colon cancer cell and/or an ovarian cancer cell.

Exemplary antibody fragments of the invention include, for example, the Fab fragments having the complementarity determining region (CDR) sequences shown in FIG. 1C and encoded by the sequences shown in FIG. 1D, where the variable light chain complementarity determining region 1 (CDR L1 or VL CDR1) includes the amino acid sequence SVSSA (SEQ ID NO: 392) and the variable light chain complementarity determining region 2 (CDR L2 or VL CDR2) includes the amino acid sequence SASSLYS (SEQ ID NO: 393). Exemplary monoclonal antibodies of the invention include, for example, antibodies having the light chain and heavy chain sequences shown in FIGS. 1A and 1B. Exemplary monoclonal antibodies of the invention include, for example, IgG antibodies having the combination of complementarity determining regions (CDRs) shown in FIG. 1C and encoded by the sequences shown in FIG. 1D, where the CDR L1 includes the amino acid sequence SVSSA (SEQ ID NO: 392) and the CDR L2 includes the amino acid sequence SASSLYS (SEQ ID NO: 393).

In some embodiments, the monoclonal antibody is an antibody or an antigen binding fragment thereof that binds to the same Frizzled epitope as antibodies having the light chain and heavy chain sequences shown in FIGS. 1A and 1B, or the antibody fragment is a fragment that binds to the same Frizzled epitope as the Fab fragments having the sequences shown in FIG. 1C and encoded by the sequences shown in FIG. 1. In some embodiments, the antibody or antigen binding fragment thereof inhibits interaction between one or more Frizzled receptors and one or more Wnt protein ligands. In some embodiments, the antibody or antigen binding fragment thereof inhibits Wnt signaling. In some embodiments, the antibody fragment is a fragment of an antibody that binds to the same Frizzled epitope as antibodies having the light chain and heavy chain sequences shown in FIGS. 1A and 1B. In some embodiments, the antibody or antigen binding fragment thereof inhibits interaction between one or more Frizzled receptors and one or more Wnt protein ligands. In some embodiments, the antibody or antigen binding fragment thereof inhibits Wnt signaling. These antibodies are collectively referred to herein as "anti-Frizzled receptor antibodies," and these fragments are collectively referred to herein as "anti-Frizzled receptor antibody fragments." In some embodiments, the antibody or immunologically active fragment thereof that binds one or more Frizzled receptors is a monoclonal antibody, domain antibody, single chain, Fab fragment, a F(ab')$_2$ fragment, a scFv, a scab, a dAb, a single domain heavy chain antibody, and a single domain light chain antibody. In some embodiments, such an antibody or immunologically active fragment thereof that binds one or more Frizzled receptors is a mouse, chimeric, humanized or fully human monoclonal antibody. These antibodies show specificity for one or more Frizzled receptors, preferably one or more human Frizzled receptors, and they have been shown to modulate, e.g., block, inhibit, reduce, antagonize, neutralize or otherwise interfere with at least one biological activity of one or more Frizzled receptors, preferably, one or more human Frizzled receptors.

In some embodiments, the antibodies and antigen-binding fragments thereof contain a heavy chain region having the amino acid sequence of SEQ ID NO: 4. In some embodiments, the antibodies and antigen-binding fragments thereof contain a light chain region having the amino acid sequence of SEQ ID NO: 2. In some embodiments, the antibodies and antigen-binding fragments thereof contain a heavy chain region having the amino acid sequence of SEQ ID NO: 4 and a light chain region having the amino acid sequence of SEQ ID NO: 2.

In some embodiments, the antibodies and antigen-binding fragments thereof contain a heavy chain region having an amino acid sequence at least 90%, 91%, 92%, 93%, 94%, 95%, 96%, 97% 98%, 99% or more identical to the amino acid sequence of SEQ ID NO: 4. In some embodiments, the antibodies and antigen-binding fragments thereof contain a light chain region having an amino acid sequence at least 90%, 91%, 92%, 93%, 94%, 95%, 96%, 97% 98%, 99% or more identical to the amino acid sequence of SEQ ID NO: 2. In some embodiments, the antibodies and antigen-binding fragments thereof contain a heavy chain region having an amino acid sequence at least 90%, 91%, 92%, 93%, 94%, 95%, 96%, 97% 98%, 99% or more identical to the amino acid sequence of SEQ ID NO: 4, and a light chain region having an amino acid sequence at least 90%, 91%, 92%, 93%, 94%, 95%, 96%, 97% 98%, 99% or more identical to the amino acid sequence of SEQ ID NO: 2.

In some embodiments, the antibodies and antigen-binding fragments thereof contain a heavy chain region that is encoded by the nucleic acid sequence of SEQ ID NO: 3. In some embodiments, the antibodies and antigen-binding fragments thereof contain a light chain region that is encoded by the nucleic acid sequence of SEQ ID NO: 1. In some embodiments, the antibodies and antigen-binding fragments thereof contain a heavy chain region that is encoded by the nucleic acid sequence of SEQ ID NO: 3 and a light chain region that is encoded by the nucleic acid sequence of SEQ ID NO: 1.

In some embodiments, the antibodies and antigen-binding fragments thereof contain a heavy chain region that is encoded by a nucleic acid sequence that is at least 90%, 91%, 92%, 93%, 94%, 95%, 96%, 97% 98%, 99% or more identical to the nucleic acid sequence of SEQ ID NO: 3. In some embodiments, the antibodies and antigen-binding fragments thereof contain a light chain region that is encoded by a nucleic acid sequence that is at least 90%, 91%, 92%, 93%, 94%, 95%, 96%, 97% 98%, 99% or more identical to the nucleic acid sequence of SEQ ID NO: 1. In some embodiments, the antibodies and antigen-binding fragments thereof contain a heavy chain region that is encoded by a nucleic acid sequence that is at least 90%, 91%, 92%, 93%, 94%, 95%, 96%, 97% 98%, 99% or more identical to the nucleic acid sequence of SEQ ID NO: 3, and a light chain region that is encoded by a nucleic acid sequence that is at least 90%, 91%, 92%, 93%, 94%, 95%, 96%, 97% 98%, 99% or more identical to the nucleic acid sequence of SEQ ID NO: 1.

In some embodiments, the antibodies and antigen-binding fragments thereof contain a heavy chain region with three heavy chain CDRs where the variable heavy chain (VH) complementarity determining region 1 (CDR H1) includes an amino acid sequence selected from the group consisting of those shown in FIG. 1C; the VH complementarity determining region 2 (CDR H2) includes an amino sequence selected from the group consisting of those shown in FIG. 1C; and the VH complementarity determining region 3 (CDR H3) includes an amino acid sequence selected from the group consisting of those shown in FIG. 1C.

In some embodiments, the antibodies and antigen-binding fragments thereof contain a heavy chain region with three heavy chain CDRs where the CDR H1 includes an amino acid sequence at least 90%, 91%, 92%, 93%, 94%, 95%, 96%, 97% 98%, 99% or more identical to an amino sequence selected from the group consisting of those shown in FIG. 1C; the CDR H2 includes an amino acid sequence at least 90%, 91%, 92%, 93%, 94%, 95%, 96%, 97% 98%, 99% or more identical to an amino sequence selected from the group consisting of those shown in FIG. 1C; and the CDR H3 includes an amino acid sequence at least 90%, 91%, 92%, 93%, 94%, 95%, 96%, 97% 98%, 99% or more identical to an amino sequence selected from the group consisting of those shown in FIG. 1C.

In some embodiments, the antibodies and antigen-binding fragments thereof contain a light chain region with three light chain CDRs where the variable light chain (VL) CDR1 (CDR L1) includes the sequence of SEQ ID NO: 392; the CDR L2 includes the amino acid sequence of SEQ ID NO: 393; and the CDR L3 includes an amino acid sequence selected from the group consisting of those shown in FIG. 1C.

In some embodiments, the antibodies and antigen-binding fragments thereof contain a light chain region with three light chain CDRs where the CDR L1 includes an amino acid sequence at least 90%, 91%, 92%, 93%, 94%, 95%, 96%, 97% 98%, 99% or more identical to the sequence of SEQ ID NO: 392; the CDR L2 includes an amino acid sequence at least 90%, 91%, 92%, 93%, 94%, 95%, 96%, 97% 98%, 99% or more identical to an amino acid sequence of SEQ ID NO: 393; and the CDR L3 includes an amino acid sequence at least 90%, 91%, 92%, 93%, 94%, 95%, 96%, 97% 98%, 99% or more identical to an amino sequence selected from the group consisting of those shown in FIG. 1C.

In some embodiments, the antibodies and antigen-binding fragments thereof contain a heavy chain region with three heavy chain CDRs and three light chain CDRs where the CDR H1 includes an amino acid sequence selected from the group consisting of those shown in FIG. 1C; the CDR H2 includes an amino sequence selected from the group consisting of those shown in FIG. 1C; the CDR H3 includes an amino acid sequence selected from the group consisting of those shown in FIG. 1C; the CDR L1 includes the sequence of SEQ ID NO: 392; the CDR L2 includes the amino acid sequence of SEQ ID NO: 393; and the CDR L3 includes an amino acid sequence selected from the group consisting of those shown in FIG. 1C.

In some embodiments, the antibodies and antigen-binding fragments thereof contain a heavy chain region with three heavy chain CDRs and three light chain CDRs where the CDR H1 includes an amino acid sequence at least 90%, 91%, 92%, 93%, 94%, 95%, 96%, 97% 98%, 99% or more identical to an amino sequence selected from the group consisting of those shown in FIG. 1C; the CDR H2 includes an amino acid sequence at least 90%, 91%, 92%, 93%, 94%, 95%, 96%, 97% 98%, 99% or more identical to an amino sequence selected from the group consisting of those shown in FIG. 1C; the CDR H3 includes an amino acid sequence at least 90%, 91%, 92%, 93%, 94%, 95%, 96%, 97% 98%, 99% or more identical to an amino sequence selected from the group consisting of those shown in FIG. 1C; the CDR L1 includes an amino acid sequence at least 90%, 91%, 92%, 93%, 94%, 95%, 96%, 97% 98%, 99% or more identical to the sequence of SEQ ID NO: 392; the CDR L2 includes an amino acid sequence at least 90%, 91%, 92%, 93%, 94%, 95%, 96%, 97% 98%, 99% or more identical to the amino acid sequence of SEQ ID NO: 393; and the CDR L3 includes an amino acid sequence at least 90%, 91%, 92%, 93%, 94%, 95%, 96%, 97% 98%, 99% or more identical to an amino sequence selected from the group consisting of those shown in FIG. 1C.

In some embodiments, the antibodies and antigen-binding fragments thereof contain a heavy chain region having the amino acid sequence of SEQ ID NO: 4, where one or more of the heavy chain CDR sequences is replaced with the corresponding CDR H1, CDR H2 and/or CDR H3 sequence selected from those listed in FIG. 1C and encoded by the sequences shown in FIG. 1D. In some embodiments, the antibodies and antigen-binding fragments thereof contain a light chain region having the amino acid sequence of SEQ ID NO: 2, where the CDR L3 is replaced with a CDR L3 sequence selected from those listed in FIG. 1C and encoded by the sequences shown in FIG. 1D. In some embodiments, the antibodies and antigen-binding fragments thereof contain a heavy chain region having the amino acid sequence of SEQ ID NO: 4, where one or more of the heavy chain CDR sequences is replaced with the corresponding CDR H1, CDR H2 and/or CDR H3 sequence selected from those listed in FIG. 1C and encoded by the sequences shown in FIG. 1D, and a light chain region having the amino acid sequence of SEQ ID NO: 2, where the CDR L3 is replaced with a CDR L3 sequence selected from those listed in FIG. 1C and encoded by the sequences shown in FIG. 1D.

In some embodiments, the antibodies and antigen-binding fragments thereof contain a heavy chain region having an amino acid sequence at least 90%, 91%, 92%, 93%, 94%, 95%, 96%, 97% 98%, 99% or more identical to the amino acid sequence of SEQ ID NO: 4, where one or more of the heavy chain CDR sequences is replaced with the corresponding CDR H1, CDR H2 and/or CDR H3 sequence selected from those listed in FIG. 1C and encoded by the sequences shown in FIG. 1D. In some embodiments, the antibodies and antigen-binding fragments thereof contain a light chain region having an amino acid sequence at least 90%, 91%, 92%, 93%, 94%, 95%, 96%, 97% 98%, 99% or more identical to the amino acid sequence of SEQ ID NO: 2, where the CDR L3 is replaced with a CDR L3 sequence selected from those listed in FIG. 1C and encoded by the sequences shown in FIG. 1D. In some embodiments, the antibodies and antigen-binding fragments thereof contain a heavy chain region having an amino acid sequence at least 90%, 91%, 92%, 93%, 94%, 95%, 96%, 97% 98%, 99% or more identical to the amino acid sequence of SEQ ID NO: 4, where one or more of the heavy chain CDR sequences is replaced with the corresponding CDR H1, CDR H2 and/or CDR H3 sequence selected from those listed in FIG. 1C and encoded by the sequences shown in FIG. 1D, and a light chain region having an amino acid sequence at least 90%, 91%, 92%, 93%, 94%, 95%, 96%, 97% 98%, 99% or more identical to the amino acid sequence of SEQ ID NO: 2, where the CDR L3 is replaced with a CDR L3 sequence selected from those listed in FIG. 1C and encoded by the sequences shown in FIG. 1D.

In some embodiments, an exemplary antibody or antigen-binding fragments thereof contain a CDR L1 that includes the amino acid sequence SVSSA (SEQ ID NO: 392), a CDR L2 that includes the amino acid sequence SASSLYS (SEQ ID NO: 393), a CDR L3 region that includes the amino acid sequence WAYGPF (SEQ ID NO: 53), a CDR H1 region that includes the amino acid sequence IYYYSM (SEQ ID NO: 54), a CDR H2 region that includes the amino acid sequence SIYSSYSYTS (SEQ ID NO: 19), and a CDR H3 region that includes the amino acid sequence SSPGADYGL (SEQ ID NO: 55). This antibody is referred to herein as H10 or mAb #111, which are used interchangeably throughout the disclosure.

In some embodiments, an exemplary antibody or antigen binding fragments thereof contain a CDR L1 that includes the amino acid sequence SVSSA (SEQ ID NO: 392), a CDR L2 that includes the amino acid sequence SASSLYS (SEQ ID NO: 393), a CDR L3 region that includes the amino acid sequence GVYLF (SEQ ID NO: 112), a CDR H1 region that includes the amino acid sequence IYSSSI (SEQ ID NO: 113), a CDR H2 region that includes the amino acid sequence SIYSSYGSTS (SEQ ID NO: 114), and a CDR H3 region that includes the amino acid sequence YHYPFGHAL (SEQ ID NO: 115). This antibody is referred to herein as G2 or mAb #140, which are used interchangeably throughout the disclosure.

In some embodiments, an exemplary antibody or antigen binding fragments thereof contain a CDR L1 that includes the amino acid sequence SVSSA (SEQ ID NO: 392), a CDR L2 that includes the amino acid sequence SASSLYS (SEQ ID NO: 393), a CDR L3 region that includes the amino acid sequence YYHPI (SEQ ID NO: 159), a CDR H1 region that includes the amino acid sequence ISSYYI (SEQ ID NO: 150), a CDR H2 region that includes the amino acid sequence SIYPYYSSTY (SEQ ID NO: 160), and a CDR H3 region that includes the amino acid sequence VWYGAM (SEQ ID NO: 161). This antibody is referred to herein as A1 or mAb #105, which are used interchangeably throughout the disclosure.

In some embodiments, an exemplary antibody or antigen binding fragments thereof contain a CDR L1 that includes the amino acid sequence SVSSA (SEQ ID NO: 392), a CDR L2 that includes the amino acid sequence SASSLYS (SEQ ID NO: 393), a CDR L3 region that includes the amino acid sequence SSYSLI (SEQ ID NO: 71), a CDR H1 region that includes the amino acid sequence LSYYSM (SEQ ID NO: 93), a CDR H2 region that includes the amino acid sequence SIYPSYGYTY (SEQ ID NO: 84), and a CDR H3 region that includes the amino acid sequence PSPGSYHGM (SEQ ID NO: 94). This antibody is referred to herein as E4 or mAb #107, which are used interchangeably throughout the disclosure.

In some embodiments, an exemplary antibody or antigen binding fragments thereof contain a CDR L1 that includes the amino acid sequence SVSSA (SEQ ID NO: 392), a CDR L2 that includes the amino acid sequence SASSLYS (SEQ ID NO: 393), a CDR L3 region that includes the amino acid sequence YWYGVAPI (SEQ ID NO: 132), a CDR H1 region that includes the amino acid sequence ISSSYI (SEQ ID NO: 133), a CDR H2 region that includes the amino acid sequence YIYSSYGSTY (SEQ ID NO: 134), and a CDR H3 region that includes the amino acid sequence ASWYAL (SEQ ID NO: 135). This antibody is referred to herein as H1 or mAb #112, which are used interchangeably throughout the disclosure.

The present invention also provides methods of treating, preventing, delaying the progression of, or otherwise ameliorating a symptom of one or more pathologies associated with aberrant Frizzled receptor activity, aberrant Frizzled receptor expression and/or aberrant Wnt signaling by administering an anti-Frizzled monoclonal antibody of the invention or immunologically active fragment thereof (e.g., antigen-binding fragment) to a subject in which such treatment or amelioration is desired. The subject to be treated is, e.g., human. The monoclonal antibody is administered in an amount sufficient to treat, prevent or alleviate a symptom associated with the pathology. The amount of monoclonal antibody sufficient to treat or prevent the pathology in the subject is, for example, an amount that is sufficient to inhibit, reduce or otherwise antagonize Frizzled receptor binding to a Wnt protein ligand. The amount of monoclonal antibody sufficient to treat or prevent the pathology in the subject is, for example, an amount that is sufficient to inhibit, reduce or otherwise antagonize Wnt signaling.

Pathologies treated and/or prevented using the anti-Frizzled receptor antibodies and anti-Frizzled receptor antibody fragments of the invention include, for example, cancer and/or bone diseases.

Pharmaceutical compositions according to the invention can include an antibody or antibody fragment of the invention and a carrier. These pharmaceutical compositions can be included in kits, such as, for example, diagnostic kits.

BRIEF DESCRIPTION OF THE DRAWINGS

FIGS. 1A and 1B are a series of illustrations depicting the heavy chain and light chain sequences of Fab H3. As an example, the amino acid and nucleotide sequences of CDRs and backbone are shown. The CDRs are underlined. The amino acid residues of CDRs listed are the following positions inclusive as designed by the IMGT nomenclature: CDR L3: 107-116; CDR H1: 30-39; CDR H2: 55-66, CDR H3: 107-115.

FIGS. 1C and 1D are a series of tables depicting the sequences of the CDRs (L3, H1, H2, and H3). Unique Fab sequences from the selections are shown. Clonal phage were amplified in 96-well culture boxes for ELISA screening. Ninety-five clones from round 2 and ninety-five clones from round 3 were screened for ELISA reactivity to the FZD7-CDR-Fc domain and a control Fc protein. A total of 57/95 phage clones from Round 3 and 59/95 phage clones from Round 2 showed signal to background ratios greater than three. Phage clones were sequenced to determine the CDR L3, H1, H2, and H3 compositions. Amino acid residues listed are the following positions inclusive as designated by the IMGT nomenclature: CDR L3: 107-116; CDR H1: 30-39; CDR H2: 55-66, CDR H3: 107-115.

FIG. 2A is a table depicting the purification summary of Fabs. Unique Fabs isolated from library screens were subcloned into an IPTG inducible expression vector and expressed in 25 ml small scale cultures. Lysates of overnight culture pellets were batch purified on Protein A beads and subjected to two sequential elutions. Yields of each elution and the total Fab yields are indicated.

FIG. 2B is a table depicting the binding of purified Fabs to purified FZD7-Fc measured by ELISA. Fabs purified from 25 ml bacterial cultures were assayed for binding to FZD7-Fc fusion protein (R&D systems) and Fc protein. ELISA plates (384 well) were coated with 2 ug/ml of protein in PBS overnight at four degrees. Wells were blocked with 0.5% BSA/PBS for 1 hour at room temperature, washed three times with 0.05% Tween20/PBS (wash buffer), and then primary dilutions of Fabs in 0.5% BSA/0.05% Tween20/PBS (dilution buffer) were added at indicated concentrations. Fabs were incubated for 1 hour at room temperature, wells were washed six times, and anti-FLAG-HRP (Sigma) was added at 1:5000 in dilution buffer. Secondary antibody was incubated for 45 minutes at room temperature, and wells were washed six times and developed with TMB substrate with an acid stop. The absorbance at 450 nm was read. n.t.=not tested.

FIG. 3 is a table depicting the binding of the purified Fabs to cells expressing FZD7 (flow cytometry). Small scale Fabs were assayed for binding to full-length FZD7 receptor to an over-expression line in MDA MB 231 cells. In parallel, Fabs were assayed for binding to endogenous receptor expressed on the MDA MB 231 cells. Cells were harvested using an EDTA solution, blocked in 2% FBS/PBS (stain buffer), and stained with 200 nM Fab for 30 min on ice. Cells were washed two times with stain buffer and incubated with anti-F(ab')2-APC secondary antibody (Jackson Immuno) at 1:1000 for 15 minutes on ice. All antibodies were diluted in stain buffer. Cells were washed three times with stain buffer and then fixed with 1% paraformaldehye for analysis by flow cytometry. The live cell population was gated based on forward and side scatter profiles, and then a positive fluorescence gate was set against a negative control Fab that did not bind to the cells. The percent of the cell population within the positive gates is indicated.

FIG. 4A is a table depicting the binding specificity of Fabs displayed on phage determined by ELISA. Phage-Fab clones were assayed for cross-binding by ELISA to FZD CDR-Fc fusion proteins (R&D systems). ELISA plates (384 well) were coated with 2 ug/ml of protein in PBS, overnight at four degrees, and binding phage were detected using an anti-M13-HRP secondary antibody. ELISAs were developed with TMB substrate with an acid stop. Positive binding results (OD450 above background signal to an Fc control protein) is indicated (+).

FIG. 4B is a table depicting the binding specificity of Fabs determined by Immuno-staining. Fabs were evaluated for cross-binding by immunofluorescence on CHO lines stably expressing GPI-linked CRD domains. +, binding detected; −, binding not detected.

FIG. 5 is a table depicting the epitope binning of the FZD7 Fab clones (competitive ELISA assay). Fzd7-Fc was coated at 2 ug/ml (384 well plates) in PBS overnight at 4 degrees. Wells were blocked with 0.5% BSA/PBS for one hour at room temperature, washed three times with 0.05% Tween20/PBS, and then indicated Fabs were diluted to 1 uM in 0.5% BSA/0.05% Tween20/PBS (dilution buffer) and added to the wells. Fabs were incubated for one hour at room temperature and then 10 ul of indicated phage was added to the well. The added phage were from PEG precipitation of a 30 ml overnight culture, and were diluted in dilution buffer to a concentration previously determined to give an ELISA signal within the linear range. Samples were incubated 20 min at room temperature and then wells were washed six times. Anti-M13-HRP (1:5000 in dilution buffer) was added for 45 minutes at room temperature, and wells were washed six times and developed with TMB substrate with an acid stop. The absorbance at 450 nm was read. The percent binding of each phage clone in the presence of the Fabs was determined by dividing the A450 signal of sample wells by the A450 signal of wells containing a negative control Fab that does not bind the Fzd7-Fc protein.

FIGS. 6A-6J is a table and a series of graphs depicting the binding affinity of the anti-FZD7 Fabs measured by Surface Plasmon Resonance (SPR). The affinity parameters are summarized in the table (FIG. 6A). FIGS. 6B-6J show the histograms of the SPR measurements.

FIG. 7 is a table depicting the binding affinity of the anti-FZD7 antibodies to additional FZDs measured by SPR. Binding affinities of the Fab panel to Fzd CDR-Fc fusion proteins (R&D systems) were assessed by SPR. Human domains were used for Fzd domains 1, 4, 5, 7, and 8. In the case of Fzd2, a mouse domain showing high sequence identity with human was used. 'x' denotes cases in which positive binding to the antigen was not observed by SPR.

FIG. 12A depicts a dose dependent decrease in the proliferation of HPAFII cells following 5 days exposure to either mAb H10 (also referred to herein as mAb #111) or G2 (also referred to herein as mAb #140). Following exposure to mAb H10 at 10 µg/ml or 50 µg/ml, there was a decrease in proliferation of 24.4% and 38.0%, respectively; following exposure to mAb G2 at 10 µg/ml or 50 µg/ml there was a decrease in proliferation of 30.4% and 48.0%, respectively. FIG. 12B depicts a dose dependent decrease in the proliferation of IMMPC2 cells following 5 days of exposure of either mAb H10 or G2. Following exposure to mAb H10 at 10 µg/ml or 50 µg/ml, there was a decrease in proliferation of 14.1% and 16.2%, respectively; following exposure to mAb G2 at 10 µg/ml or 50 µg/ml, there was a decrease in proliferation of 15.7% and 17.9% respectively. FIG. 12C depicts a dose dependent decrease in the proliferation of PANC08.13 cells, following 5 days of exposure of either to either mAb H10 or G2. Following exposure to mAb H10 at 10 µg/ml or 50 µg/ml, there was a decrease in proliferation of 0.16% and 7.7%, respectively; following exposure to mAb G2 at 10 µg/ml or 50 µg/ml there was a decrease in proliferation of 4.7% and 7.7%, respectively. FIG. 12D depicts a dose dependent decrease in proliferation of ASPC-1 cells following 5 days of exposure to either mAb H10 or G2. Following exposure to mAb H10 at 10 µg/ml or 50 µg/ml, there was a decrease in proliferation of 37.5% or 41.9%, respectively; following exposure to mAb G2 at 10 µg/ml or 50 µg/ml there was a decrease in proliferation of 42.3% and 45.8%, respectively. FIG. 12E depicts a dose dependent decrease in the proliferation of Capan-2 cells, following 5 days of exposure to anti-FZD7 mAbs A1 (also referred to herein as mAb #105), E4 (also referred to herein as mAb #107), H10 (mAb #111), H1 (also referred to herein as mAb #112), and G2 (mAb #140). The levels of reduction in proliferation were comparable with those found after exposure to the 18R5 antibody. Collectively, exposure of the anti-FZD7 mAbs at either 10 µg/ml or 50 µg/ml resulted in a decrease in the proliferation of the Capan-2 cells by greater than 35%.

FIG. 13A depicts the dose dependent reduction of proliferation of ASPC-1 cells following a 5 day incubation with mAbs A1 (mAb #105), E4 (mAb #107) or H10 (mAb #111) at a concentration of 1 µg/ml, 2 µg/ml, 5 µg/ml, 10 µg/ml, or 50 µg/ml. FIG. 13 B depicts a does dependent reduction of proliferation of ASPC-1 cells following a 5 day incubation with mAbs H1 (mAb #112), G2 (mAb #140) or 18R5 at a concentration of 1 µg/ml, 2 µg/ml, 5 µg/ml, 10 µg/ml, or 50 µg/ml.

DETAILED DESCRIPTION

Figure 6B:
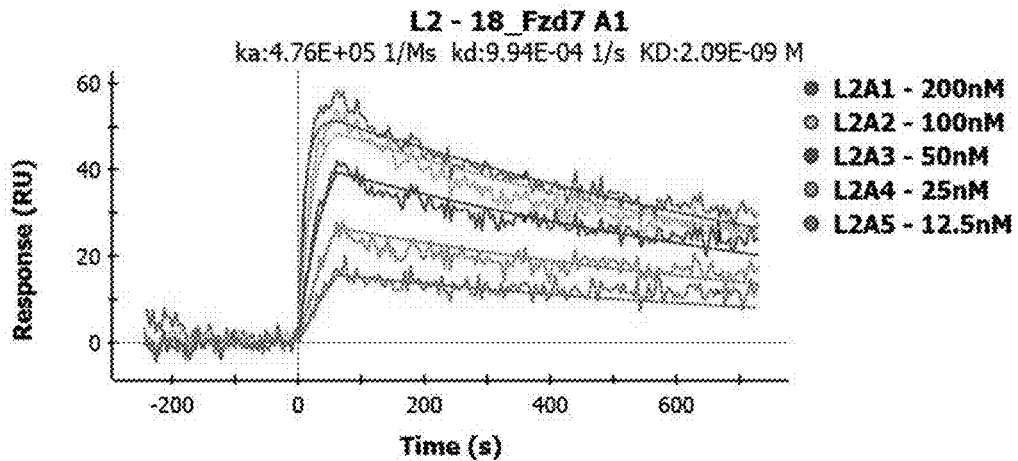
Figure 6C:
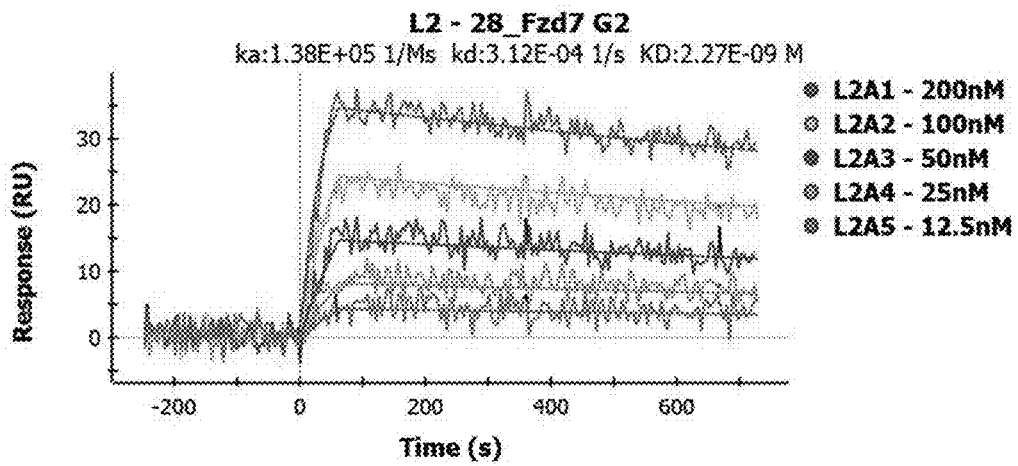
Figure 6D:
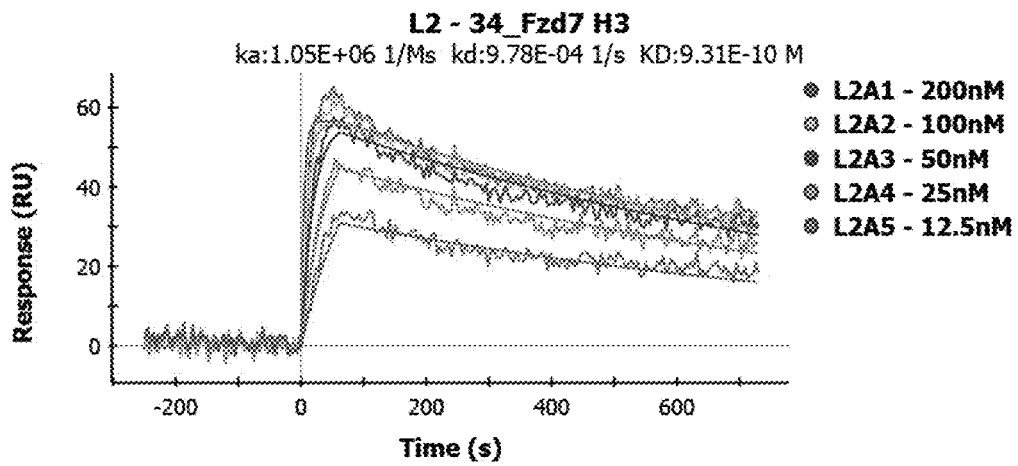
Figure 6E:
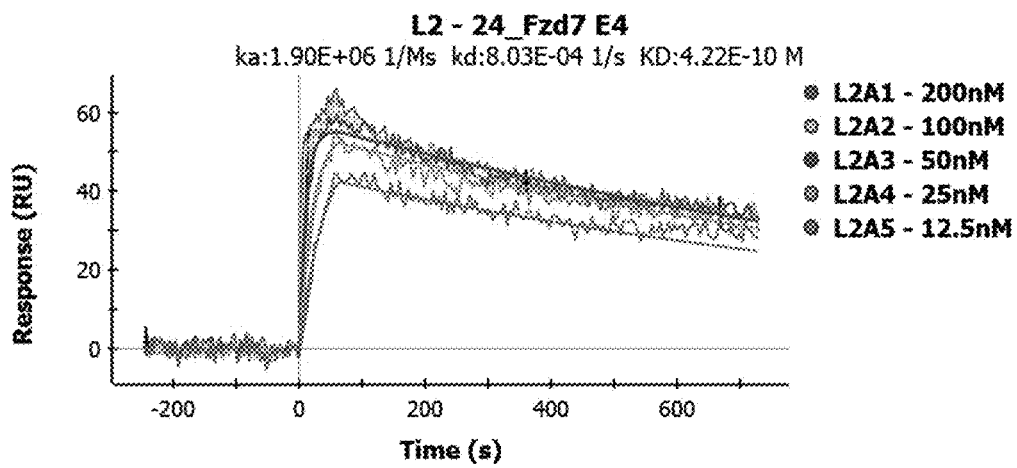
Figure 6F:
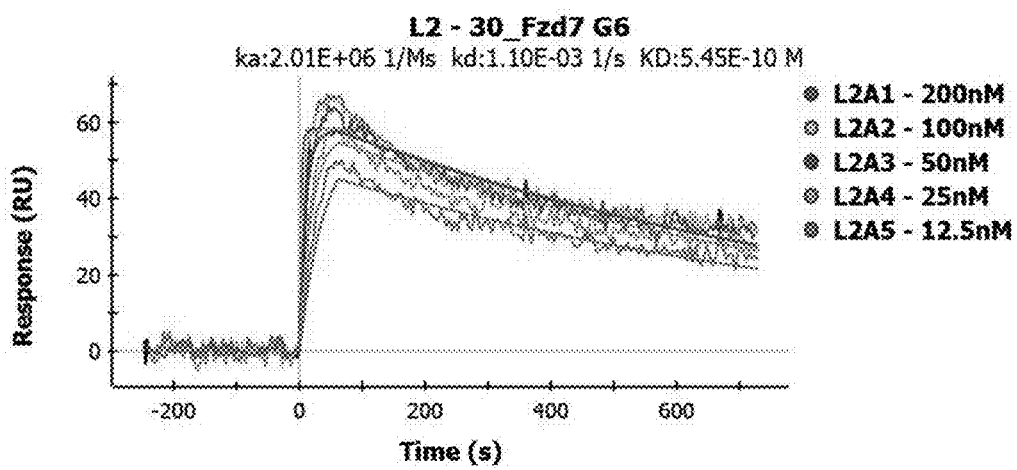
Figure 6G:
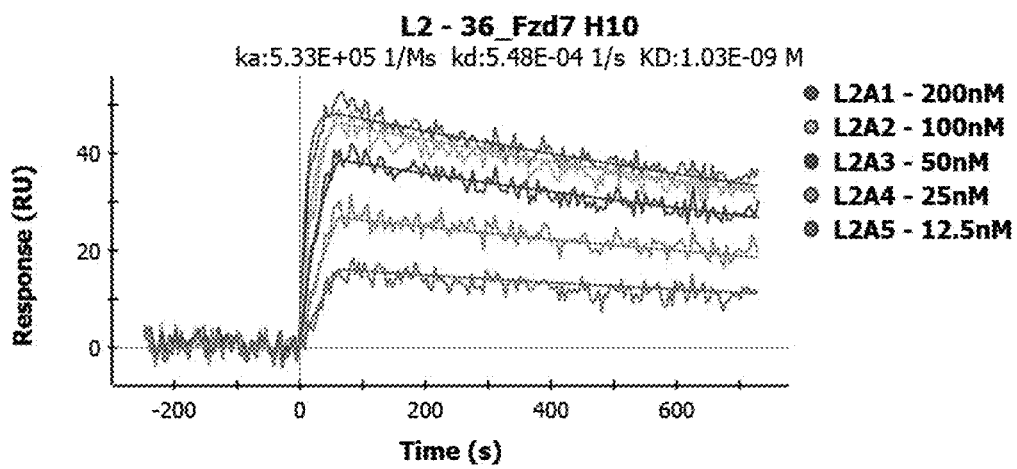
Figure 6H:
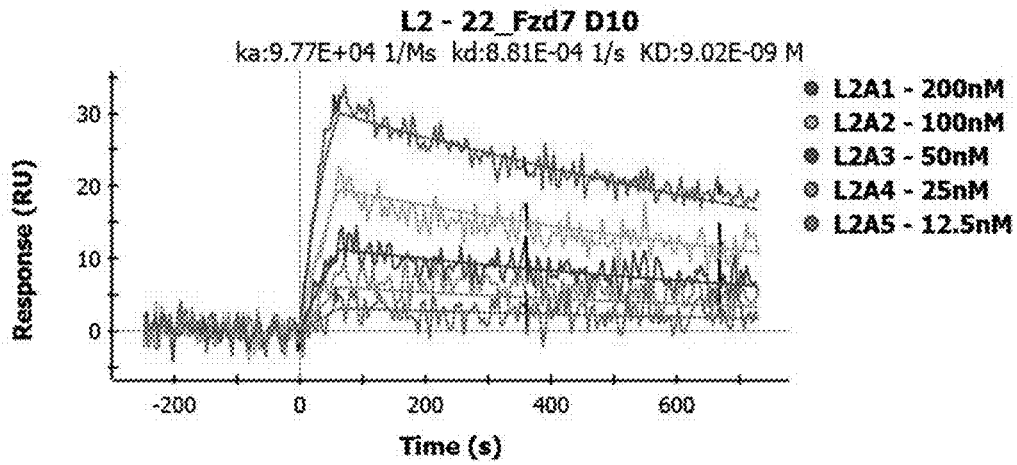
Figure 6I:
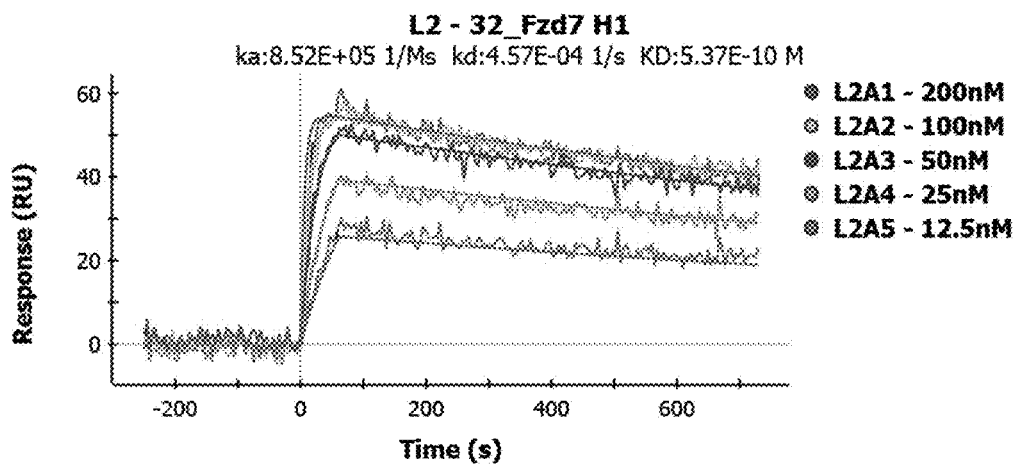
Figure 6J:
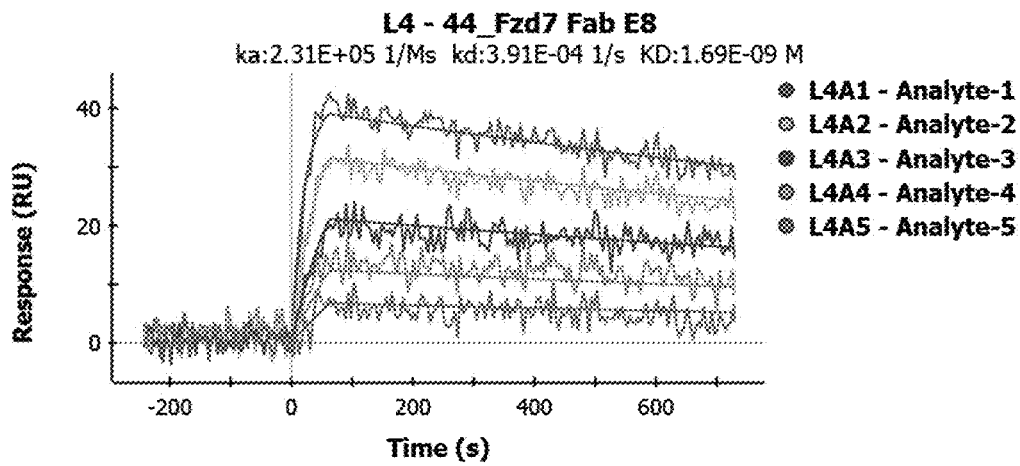

The present invention provides high affinity antibodies such as monoclonal antibodies which recognize one or more Frizzled receptors. Frizzled receptors are an important class of G protein-coupled receptors that have been implicated in various biological processes, including development, cell proliferation, differentiation, survival and migration as well as in numerous pathological conditions such as cancers. The antibodies provided herein bind to a Frizzled receptor or to a combination of Frizzled receptors, block ligand Wnt binding and modulate Frizzled receptor-mediated signaling. Therefore, these antibodies have therapeutic potential for treating cancer and other diseases where Frizzled receptors are dysregulated.

Frizzled receptors are involved in many important biological processes such as development, cell proliferation, survival, migration and stem cell maintenance. Abnormal expression and signaling of these receptors and their ligands, Wnt proteins, have been associated with numerous cancers, including colon, lung, breast and ovarian cancers. Frequently, multiple Wnt ligands and/or Frizzled receptors are up-regulated and lead to aberrant signaling that drives tumorigenesis. Therefore, inhibition of multiple Frizzled receptors can be used to achieve increased anti-cancer efficacy. In addition, Frizzled receptors have also been implicated in cancer stem cells, a small population of cancer cells that are thought to be responsible for drug resistance, tumor relapse and metastasis. Thus, antagonistic antibodies against Frizzled receptors may be used to target cancer stem cells and to treat various type of cancer. For example, the antagonistic antibodies against FZD7 provided herein are useful to treat cancers that express FZD7 and depend on FZD7. Since these antibodies also bind to additional FZD receptors, these antibodies may be used to treat cancers that express and depend on other Frizzled receptors.

The Wnt signaling pathways are a group of signal transduction pathways made of proteins that pass signals from outside of a cell through cell surface receptors to the inside of the cell. Three Wnt signaling pathways have been characterized: the canonical Wnt pathway, the noncanonical planar cell polarity pathway, and the noncanonical Wnt/calcium pathway. All three Wnt signaling pathways are activated by the binding of a Wnt-protein ligand to a Frizzled receptor, which passes the biological signal to the protein Disheveled inside the cell. The canonical Wnt pathway leads to regulation of gene transcription, the noncanonical planar cell polarity pathway regulates the cytoskeleton that is responsible for the shape of the cell, and the noncanonical Wnt/calcium pathway regulates calcium inside the cell.

The antibodies of the invention modulate the interaction between one or more Frizzled receptors and a Wnt protein ligand. Frizzled receptors include a Frizzled receptor selected from Frizzled-1 (FZD1), Frizzled-2 (FZD2), Frizzled-3 (FZD3), Frizzled-4 (FZD4), Frizzled-5 (FZD5), Frizzled-6 (FZD6), Frizzled-8 (FZD8), Frizzled-9 (FZD9) and Frizzled-10 (FZD10). Wnt protein ligands include a human Wnt protein such as, for example, a human Wnt protein selected from Wnt1, Wnt2, Wnt2B, Wnt3, Wnt3A, Wnt4, Wnt5A, Wnt5B, Wnt6, Wnt7A, Wnt7B, Wnt8A, Wnt8B, Wnt9A, Wnt9B, Wnt10A, Wnt10B, Wnt11, and Wnt16. The anti-Frizzled antibodies inhibit or otherwise antagonize binding to a Wnt protein ligand and modulate activation of a Wnt signaling pathway. For example, the anti-Frizzled antibodies inhibit or otherwise antagonize binding to a Wnt protein ligand and modulate activation of and/or signaling via the canonical Wnt pathway, the noncanonical planar cell polarity pathway, and/or the noncanonical Wnt/calcium pathway.

In some embodiments, the antibodies bind the cysteine-rich domain (CRD) of FZD7. In some embodiments, the antibodies bind one or more Frizzled receptors selected from Frizzled-1 (FZD1), Frizzled-2 (FZD2), Frizzled-3 (FZD3), Frizzled-4 (FZD4), Frizzled-5 (FZD5), Frizzled-6 (FZD6), Frizzled-7 (FZD7), Frizzled-8 (FZD8), Frizzled-9 (FZD9) and Frizzled-10 (FZD10). In some embodiments the antibodies bind more than one Frizzled receptor selected from FZD1, FZD2, FZD3, FZD4, FZD5, FZD6, FZD7, FZD8, FZD9 and FZD10. For example, in some embodiments, the antibodies bind at least 2, at least 3, at least 4, at least 5, at least 6, at least 7, at least 8, or at least 9 or more Frizzled receptors.

In some embodiments, the antibodies bind the cysteine-rich domain (CRD) of a Frizzled receptor. In some embodiments, the antibodies bind the cysteine-rich domain (CRD) of one or more Frizzled receptors selected from FZD1, FZD2, FZD3, FZD4, FZD5, FZD6, FZD7, FZD8, FZD9 and FZD10. In some embodiments, the antibodies bind the cysteine-rich domain (CRD) of more than one Frizzled receptor selected from FZD1, FZD2, FZD3, FZD4, FZD5, FZD6, FZD7, FZD8, FZD9 and FZD10. For example, in some embodiments, the antibodies bind the CRD domains of at least 2, at least 3, at least 4, at least 5, at least 6, at least 7, at least 8, or at least 9 or more Frizzled receptors. These antibodies are capable of modulating, e.g., blocking, inhibiting, reducing, antagonizing, neutralizing or otherwise interfering with one or more biological activities of one or more Frizzled receptors.

In some embodiments, the antibodies bind Frizzled-7 receptor, also referred to herein as Frizzled-7 and/or FZD7. In some embodiments, the antibodies bind human FZD7. In some embodiments, the antibodies bind FZD7 in combination with one or more Frizzled receptors selected from FZD1, FZD2, FZD3, FZD4, FZD5, FZD6, FZD8, FZD9 and FZD10. In some embodiments, the antibodies bind human FZD7 in combination with one or more human Frizzled receptors selected from human FZD1, human FZD2, human FZD3, human FZD4, human FZD5, human FZD6, human FZD8, human FZD9 and human FZD10.

The antibodies of the present invention bind to an epitope on one or more Frizzled receptors, e.g., an epitope on human FZD7, with an equilibrium binding constant ($K_d$) of ≤1 µM, e.g., ≤100 nM, preferably ≤10 nM, and more preferably ≤1 nM. For example, the anti-Frizzled receptor antibodies and fragments provided herein exhibit a $K_d$ in the range shown in FIG. 6 and/or FIG. 7.

The anti-Frizzled receptor antibodies and fragments of the invention serve to modulate, block, inhibit, reduce, antagonize, neutralize or otherwise interfere with at least one functional activity of one or more Frizzled receptors. For example, the anti-Frizzled receptor antibodies and/or anti-Frizzled receptor antibody fragments completely or partially inhibit a Frizzled functional activity by partially or completely modulating, blocking, inhibiting, reducing antagonizing, neutralizing, or otherwise interfering with the binding of one or more Frizzled receptors to Wnt protein ligand. For example, the anti-Frizzled receptor antibodies and/or anti-Frizzled receptor antibody fragments completely or partially inhibit Frizzled functional activity by partially or completely modulating, blocking, inhibiting, reducing antagonizing, neutralizing, or otherwise interfering with the activation of one or more Frizzled receptors.

Anti-Frizzled receptor antibodies and/or anti-Frizzled receptor antibody fragments are considered to completely block at least one functional activity of one or more Frizzled receptors when the level of the functional activity in the presence of the anti-Frizzled receptor antibody and/or anti-Frizzled receptor antibody fragment is decreased by at least 95%, e.g., by 96%, 97%, 98%, 99% or 100% as compared to the level of the functional activity in the absence of interaction, e.g., binding, with the anti-Frizzled receptor antibody and/or anti-Frizzled receptor antibody fragment. Anti-Frizzled receptor antibodies and/or anti-Frizzled receptor antibody fragments are considered to partially block at least one functional activity of one or more Frizzled receptors when the level of the functional activity in the presence of the anti-Frizzled receptor antibody and/or anti-Frizzled receptor antibody fragment is decreased by at least 50%, e.g., 55%, 60%, 75%, 80%, 85% or 90% as compared to the level of the functional activity in the absence of interaction, e.g., binding, with the anti-Frizzled receptor antibody and/or anti-Frizzled receptor antibody fragment.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" "or directed against" is meant that the antibody reacts with one or more antigenic determinants of the desired antigen and does not react with other polypeptides or binds at much lower affinity ($K_d>10^{-6}$). Antibodies include, but are not limited to, polyclonal, monoclonal, chimeric, dAb (domain antibody), single chain, $F_{ab}$, $F_{ab'}$ and $F_{(ab')2}$ fragments, scFvs, and an $F_{ab}$ expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin or fragment thereof, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is ≤1 µM; e.g., ≤100 nM, preferably ≤10 nM and more preferably ≤1 nM.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to one or more Frizzled receptors, when the equilibrium binding constant ($K_d$) is ≤1 µM, preferably ≤100 nM, more preferably ≤10 nM, and most preferably ≤100 µM to about 1 µM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence. Polynucleotides in accordance with the invention include the nucleic acid molecule encoding the heavy chain immunoglobulin molecule presented in SEQ ID NO: 4, e.g., the nucleic acid sequence of SEQ ID NO: 3, and the nucleic acid molecule encoding the light chain immunoglobulin molecule represented in SEQ ID NO: 2, e.g., the nucleic acid sequence of SEQ ID NO: 1.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the invention comprise the heavy chain immunoglobulin molecule represented in SEQ ID NO: 4, and the light chain immunoglobulin molecule represented in SEQ ID NO: 2 as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means a polymer of nucleotides of at least 10 bases in length, either ribonucleotides or deoxynucleotides or a modified form of either type of nucleotide. The term includes single and double stranded forms of DNA.

The term "oligonucleotide" referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the invention are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes Oligonucleotides linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest will be at least 80%, and more typically with preferably increasing homologies of at least 85%, 90%, 95%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman Adv. Appl. Math. 2:482 (1981), by the homology alignment algorithm of Needleman and Wunsch J. Mol. Biol. 48:443 (1970), by the search for similarity method of Pearson and Lipman Proc. Natl. Acad. Sci. (U.S.A.) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See Immunology—A Synthesis (2nd Edition, E. S. Golub and D. R. Gren, Eds., Sinauer Associates, Sunderland? Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and which are 5' to the 5' end of the RNA transcript are referred to as "upstream sequences", sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity.

Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

The term "polypeptide fragment" as used herein refers to a polypeptide that has an amino terminal and/or carboxy-terminal deletion, but where the remaining amino acid sequence is identical to the corresponding positions in the naturally-occurring sequence deduced, for example, from a full length cDNA sequence. Fragments typically are at least 5, 6, 8 or 10 amino acids long, preferably at least 14 amino acids long' more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has specific binding to one or more Frizzled receptors, under suitable binding conditions. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics". Fauchere, J. Adv. Drug Res. 15:29 (1986), Veber and Freidinger TINS p. 392 (1985); and Evans et al. J. Med. Chem. 30:1229 (1987). Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —$CH_2NH$—, —$CH_2S$—, —$CH_2$—$CH_2$—, —CH=CH—-(cis and trans), —$COCH_2$—, $CH(OH)CH_2$—, and —$CH_2SO$—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992)); for example, by adding internal cysteine residues capable of forming intramolecular disulfide bridges which cyclize the peptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

The term "antineoplastic agent" is used herein to refer to agents that have the functional property of inhibiting a development or progression of a neoplasm in a human, particularly a malignant (cancerous) lesion, such as a carcinoma, sarcoma, lymphoma, or leukemia. Inhibition of metastasis is frequently a property of antineoplastic agents.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present.

Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

Other chemistry terms herein are used according to conventional usage in the art, as exemplified by The McGraw-Hill Dictionary of Chemical Terms (Parker, S., Ed., McGraw-Hill, San Francisco (1985)).

Anti-Frizzled Receptor Antibodies and Fragments

Monoclonal antibodies and antigen-binding fragments thereof have the ability to inhibit Frizzled function and/or Frizzled activation. Inhibition is determined, for example, using the materials and methods described herein.

Exemplary antibody fragments of the invention include, for example, the Fab fragments having the sequences shown in FIG. 1C and encoded by the sequences shown in FIG. 1D, where the variable light chain complementarity determining region 1 (CDR L1 or VL CDR1) includes the amino acid sequence SVSSA (SEQ ID NO: 392) and the variable light chain complementarity determining region 2 (CDR L2 or VL CDR2) includes the amino acid sequence SASSLYS (SEQ ID NO: 393). The amino acids encompassing the complementarity determining regions (CDR) are as defined by E. A. Kabat et al. (See Kabat, E A, et al., Sequences of Protein of immunological interest, Fifth Edition, US Department of Health and Human Services, US Government Printing Office (1991)). Exemplary monoclonal antibodies of the invention include, for example, antibodies having the light chain and heavy chain sequences shown in FIGS. 1A and 1B. Exemplary monoclonal antibodies of the invention include, for example, antibodies having the combination of complementarity determining regions (CDRs) shown in FIG. 1C and encoded by the sequences shown in FIG. 1D, where the CDR L1 includes the amino acid sequence SVSSA (SEQ ID NO: 392) and the CDR L2 includes the amino acid sequence SASSLYS (SEQ ID NO: 393). Alternatively, the monoclonal antibody is an antibody that binds to the same Frizzled epitope as these antibodies or antibody fragments.

Those skilled in the art will recognize that it is possible to determine, without undue experimentation, if an anti-Frizzled receptor antibody (e.g., monoclonal antibody) has the same specificity as an antibody or antibody fragment of the invention by ascertaining whether the former prevents the latter from binding to collagen. If the monoclonal antibody being tested competes with the monoclonal antibody of the invention, as shown by a decrease in binding by the monoclonal antibody of the invention, then the two monoclonal antibodies bind to the same, or a closely related, epitope.

An alternative method for determining whether a monoclonal antibody has the specificity of an antibody or antibody fragment of the invention is to pre-incubate the monoclonal antibody of the invention with soluble Frizzled receptor protein, and then add the monoclonal antibody being tested to determine if the monoclonal antibody being tested is inhibited in its ability to bind one or more Frizzled receptors. If the monoclonal antibody being tested is inhibited then, in all likelihood, it has the same, or functionally equivalent, epitopic specificity as the monoclonal antibody of the invention.

Screening of monoclonal antibodies and antigen-binding fragments thereof, can be also carried out, e.g., by measuring binding between one or more Frizzled receptors and a Wnt protein ligand, and determining whether the test monoclonal antibody is able to modulate, block, inhibit, reduce, antagonize, neutralize or otherwise interfere with binding between the Frizzled receptor(s) and the Wnt protein ligand.

Various procedures known within the art may be used for the production of monoclonal antibodies directed against one or more Frizzled receptors, or against derivatives, fragments, analogs homologs or orthologs thereof. (See, for example, Antibodies: A Laboratory Manual, Harlow E, and Lane D, 1988, Cold Spring Harbor Laboratory Press, Cold Spring Harbor, N.Y., incorporated herein by reference). Fully human antibodies are antibody molecules in which the entire sequence of both the light chain and the heavy chain, including the CDRs, arise from human genes. Such antibodies are termed "human antibodies" or "fully human antibodies" herein. Human monoclonal antibodies are prepared, for example, using the procedures described in the Examples provided below. Human monoclonal antibodies can be also prepared by using the trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96)

Antibodies are purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

The antibodies and fragments of the invention are monoclonal antibodies. Monoclonal antibodies that modulate, block, inhibit, reduce, antagonize, neutralize or otherwise interfere with Frizzled receptor activity, expression and/or Wnt signaling are generated, e.g., by immunizing an animal with membrane bound and/or soluble Frizzled receptor, such as, for example, murine, rat or human Frizzled receptor or an immunogenic fragment, derivative or variant thereof. Alternatively, the animal is immunized with cells transfected with a vector containing a nucleic acid molecule encoding a Frizzled receptor is expressed and associated with the surface of the transfected cells. Alternatively, the antibodies are obtained by screening a library that contains antibody or antigen binding domain sequences for binding to one or more Frizzled receptors. This library is prepared, e.g., in bacteriophage as protein or peptide fusions to a bacteriophage coat protein that is expressed on the surface of assembled phage particles and the encoding DNA sequences contained within the phage particles (i.e., "phage displayed library"). Hybridomas resulting from myeloma/B cell fusions are then screened for reactivity to one or more Frizzled receptors.

Monoclonal antibodies are prepared, for example, using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (MA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies and antigen-binding fragments thereof can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Human Antibodies and Humanization of Antibodies

Monoclonal antibodies and antigen-binding fragments thereof include fully human antibodies or humanized antibodies. These antibodies are suitable for administration to humans without engendering an immune response by the human against the administered immunoglobulin.

An anti-Frizzled receptor antibody or fragment is generated, for example, using the procedures described in the Examples provided below.

In some methods, an anti-Frizzled receptor antibody or fragment is developed, for example, using phage-display methods using antibodies containing only human sequences. Such approaches are well-known in the art, e.g., in WO92/01047 and U.S. Pat. No. 6,521,404, which are hereby incorporated by reference. In this approach, a combinatorial library of phage carrying random pairs of light and heavy chains are screened using natural or recombinant source of a Frizzled receptor or fragments thereof. In another approach, an antibody or fragment can be produced by a process wherein at least one step of the process includes immunizing a transgenic, non-human animal with a human Frizzled receptor protein. In this approach, some of the endogenous heavy and/or kappa light chain loci of this xenogenic non-human animal have been disabled and are incapable of the rearrangement required to generate genes encoding immunoglobulins in response to an antigen. In addition, at least one human heavy chain locus and at least one human light chain locus have been stably transfected into the animal. Thus, in response to an administered antigen, the human loci rearrange to provide genes encoding human variable regions immunospecific for the antigen. Upon immunization, therefore, the xenomouse produces B-cells that secrete fully human immunoglobulins.

A variety of techniques are well-known in the art for producing xenogenic non-human animals. For example, see U.S. Pat. Nos. 6,075,181 and 6,150,584, which is hereby incorporated by reference in its entirety. This general strategy was demonstrated in connection with generation of the first XenoMouse™ strains as published in 1994. See Green et al. Nature Genetics 7:13-21 (1994), which is hereby incorporated by reference in its entirety. See also, U.S. Pat. Nos. 6,162,963, 6,150,584, 6, 114,598, 6,075,181, and 5,939,598 and Japanese Patent Nos. 3 068 180 B2, 3 068 506 B2, and 3 068 507 B2 and European Patent No., EP 0 463 151 B1 and International Patent Applications No. WO 94/02602, WO 96/34096, WO 98/24893, WO 00/76310 and related family members.

In an alternative approach, others have utilized a "minilocus" approach in which an exogenous Ig locus is mimicked through the inclusion of pieces (individual genes) from the Ig locus. Thus, one or more VH genes, one or more $D_H$ genes, one or more $J_H$ genes, a mu constant region, and a second constant region (preferably a gamma constant region) are formed into a construct for insertion into an animal. See e.g., U.S. Pat. Nos. 5,545,806; 5,545,807; 5,591,669; 5,612,205; 5,625,825; 5,625,126; 5,633,425; 5,643,763; 5,661,016; 5,721,367; 5,770,429; 5,789,215; 5,789,650; 5,814,318; 5,877; 397; 5,874,299; 6,023,010; and 6,255,458; and European Patent No. 0 546 073 B 1; and International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and related family members.

Generation of human antibodies from mice in which, through microcell fusion, large pieces of chromosomes, or entire chromosomes, have been introduced, has also been demonstrated. See European Patent Application Nos. 773 288 and 843 961.

Human anti-mouse antibody (HAMA) responses have led the industry to prepare chimeric or otherwise humanized antibodies. While chimeric antibodies have a human constant region and a immune variable region, it is expected that certain human anti-chimeric antibody (HACA) responses will be observed, particularly in chronic or multi-dose utilizations of the antibody. Thus, it would be desirable to provide fully human antibodies against one or more Frizzled receptors in order to vitiate or otherwise mitigate concerns and/or effects of HAMA or HACA response.

The production of antibodies with reduced immunogenicity is also accomplished via humanization, chimerization and display techniques using appropriate libraries. It will be appreciated that murine antibodies or antibodies from other species can be humanized or primatized using techniques well known in the art. See e.g., Winter and Harris Immunol Today 14:43 46 (1993) and Wright et al. Crit, Reviews in Immunol. 12125-168 (1992). The antibody of interest may be engineered by recombinant DNA techniques to substitute the CH1, CH2, CH3, hinge domains, and/or the framework domain with the corresponding human sequence (See WO 92102190 and U.S. Pat. Nos. 5,530,101; 5,585,089; 5,693,761; 5,693,792; 5,714,350; and 5,777,085). Also, the use of Ig cDNA for construction of chimeric immunoglobulin genes is known in the art (Liu et al. P.N.A.S. 84:3439 (1987) and J. Immunol. 139:3521 (1987)). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) Sequences of Proteins of immunological Interest, N.I.H. publication no. 91-3242. Human C region genes are readily available from known clones. The choice of isotype will be guided by the desired effecter functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Antibody fragments, such as Fv, F(ab')$_2$ and Fab may be prepared by cleavage of the intact protein, e.g., by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g., SV-40 early promoter, (Okayama et al. Mol. Cell. Bio. 3:280 (1983)), Rous sarcoma virus LTR (Gorman et al. P.N.A.S. 79:6777 (1982)), and moloney murine leukemia virus LTR (Grosschedl et al. Cell 41:885 (1985)). Also, as will be appreciated, native Ig promoters and the like may be used.

Further, human antibodies or antibodies from other species can be generated through display type technologies, including, without limitation, phage display, retroviral display, ribosomal display, and other techniques, using techniques well known in the art and the resulting molecules can be subjected to additional maturation, such as affinity maturation, as such techniques are well known in the art. Wright et al. Crit, Reviews in Immunol. 12125-168 (1992), Hanes and Pluckthun PNAS USA 94:4937-4942 (1997) (ribosomal display), Parmley and Smith Gene 73:305-318 (1988) (phage display), Scott, TIBS, vol. 17:241-245 (1992), Cwirla et al. PNAS USA 87:6378-6382 (1990), Russel et al. Nucl. Acids Research 21:1081-1085 (1993), Hoganboom et al. Immunol. Reviews 130:43-68 (1992), Chiswell and McCafferty TIBTECH; 10:80-8A (1992), and U.S. Pat. No. 5,733,743. If display technologies are utilized to produce antibodies that are not human, such antibodies can be humanized as described above.

Using these techniques, antibodies can be generated to Frizzled receptor-expressing cells, soluble forms of one or more Frizzled receptors or combination thereof, epitopes or peptides thereof, and expression libraries thereto (See e.g., U.S. Pat. No. 5,703,057) which can thereafter be screened as described above for the activities described herein.

The anti-Frizzled receptor antibodies and fragments of the invention can be expressed by a vector containing a DNA segment encoding the single chain antibody described above.

These can include vectors, liposomes, naked DNA, adjuvant-assisted DNA, gene gun, catheters, etc. Vectors include chemical conjugates such as described in WO 93/64701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci USA 87:1149 (1990), Adenovirus Vectors (see LeGal LaSalle et al., Science, 259:988 (1993); Davidson, et al., Nat. Genet 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, CaPO$_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g. adenovirus, HSV) to a desired location. Additionally, the particles can be delivered by intracerebroventricular (icy) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266:292-305 (1994)). Other methods that can be used include catheters, intravenous, parenteral, intraperitoneal and subcutaneous injection, and oral or other known routes of administration.

These vectors can be used to express large quantities of antibodies that can be used in a variety of ways. For example, to detect the presence of one or more Frizzled receptors in a sample. The antibody can also be used to try to bind to and disrupt a Frizzled receptor-related activity.

Techniques can be adapted for the production of single-chain antibodies specific to an antigenic protein of the invention (see e.g., U.S. Pat. No. 4,946,778). In addition, methods can be adapted for the construction of Fab expression libraries (see e.g., Huse, et al., 1989 Science 246: 1275-1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an Fab fragment generated by reducing the disulfide bridges of an $F_{(ab')2}$ fragment; (iii) an $F_{ab}$ fragment generated by the treatment of the antibody molecule with papain and a reducing agent and (iv) Fv fragments.

The invention also includes $F_v$, $F_{ab}$, $F_{ab'}$ and $F_{(ab')2}$ anti-Frizzled receptor antibody fragments, single chain anti-Frizzled receptor antibodies, bispecific anti-Frizzled receptor antibodies, and heteroconjugate anti-Frizzled receptor antibodies.

Bispecific antibodies are antibodies that have binding specificities for at least two different antigens. In the present case, one of the binding specificities is for a Frizzled receptor or a combination of Frizzled receptors. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from E. coli and chemically coupled to form bispecific antibodies. Shalaby et al., J. Exp. Med. 175:217-225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$)

connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994).

Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate antibodies are also within the scope of the present invention. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody of the invention with respect to effector function, so as to enhance, e.g., the effectiveness of the antibody in treating diseases and disorders associated with aberrant Frizzled receptor activation and/or activity. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies and antigen-binding fragments thereof. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987).

Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030, 719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NETS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Use of Antibodies Against Frizzled Receptors

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

In one embodiment, antibodies and antigen-binding fragments thereof, which include a monoclonal antibody of the invention, may be used as therapeutic agents. Such agents will generally be employed to diagnose, prognose, monitor, treat, alleviate, and/or prevent a disease or pathology associated with aberrant Frizzled receptor activity and/or activation in a subject. A therapeutic regimen is carried out by identifying a subject, e.g., a human patient suffering from (or at risk of developing) a disease or disorder associated with aberrant Frizzled receptor activity, e.g., cancer or an inflammatory disorder, using standard methods. An antibody preparation, preferably one having high specificity and high affinity for its target antigen, is administered to the subject and will generally have an effect due to its binding with the target. Administration of the antibody may abrogate or inhibit or interfere with a function of the target (e.g., one or more Frizzled receptors). Administration of the antibody may abrogate or inhibit or interfere with the binding of the target (e.g., one or more Frizzled receptor) with an endogenous ligand (e.g., collagen) to which it naturally binds. Administration of the antibody may modulate, block, inhibit, reduce, antagonize, neutralize, or otherwise interfere with one or more biological activities of one or more Frizzled receptors.

Diseases or disorders related to aberrant Frizzled receptor activity, activation, expression and/or Wnt signaling include cancers and inflammatory disorders.

A therapeutically effective amount of an antibody of the invention relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Efficaciousness of treatment is determined in association with any known method for diagnosing or treating the particular cancer and/or inflammatory-related disorder. Alleviation of one or more symptoms of the cancer and/or inflammatory-related disorder indicates that the antibody confers a clinical benefit.

Methods for the screening of antibodies that possess the desired specificity include, but are not limited to, enzyme linked immunosorbent assay (ELISA) and other immunologically mediated techniques known within the art.

In another embodiment, antibodies and fragments directed against one or more Frizzled receptors may be used in methods known within the art relating to the localization and/or quantitation of one or more Frizzled receptors (e.g., for use in measuring levels of one or more Frizzled receptors within appropriate physiological samples, for use in diagnostic methods, for use in imaging the protein, and the like). In a given embodiment, antibodies specific to one or more Frizzled receptors, or derivative, fragment, analog or homolog thereof, that contain the antibody derived antigen binding domain, are utilized as pharmacologically active compounds (referred to hereinafter as "Therapeutics").

In another embodiment, an antibody or fragment specific for one or more Frizzled receptors can be used to isolate a Frizzled receptor polypeptide, by standard techniques, such as immunoaffinity, chromatography or immunoprecipitation. Antibodies directed against one or more Frizzled receptors (or a fragment thereof) can be used diagnostically to monitor protein levels in tissue as part of a clinical testing procedure to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

In yet another embodiment, an antibody according to the invention can be used as an agent for detecting the presence of one or more Frizzled receptors (or a protein fragment thereof) in a sample. In some embodiments, the antibody contains a detectable label. Antibodies are polyclonal, or more preferably, monoclonal. An intact antibody, or a fragment thereof (e.g., $F_{ab}$, scFv, or $F_{(ab)2}$) is used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Therapeutic Administration and Formulations of Anti-Frizzled Receptor Antibodies and Fragments The antibodies of the invention (also referred to herein as "active compounds"), and derivatives, fragments, analogs and homologs thereof, can be incorporated into pharmaceutical compositions suitable for administration. Principles and considerations involved in preparing such compositions, as well as guidance in the choice of components are provided, for example, in Remington's Pharmaceutical Sciences: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Such compositions typically comprise the antibody and a pharmaceutically acceptable carrier. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)).

As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated.

The formulations to be used for in vivo administration must be sterile. This is readily accomplished by filtration through sterile filtration membranes.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a sustained/controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

For example, the active ingredients can be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

The materials can also be obtained commercially from Alza Corporation and Nova Pharmaceuticals, Inc. Liposomal suspensions (including liposomes targeted to infected cells with monoclonal antibodies to viral antigens) and can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

In one embodiment, the active compounds are administered in combination therapy, i.e., combined with other agents, e.g., therapeutic agents, that are useful for treating pathological conditions or disorders, such as various forms of cancer and inflammatory diseases. The term "in combination" in this context means that the agents are given substantially contemporaneously, either simultaneously or sequentially. If given sequentially, at the onset of administration of the second compound, the first of the two compounds is preferably still detectable at effective concentrations at the site of treatment.

For example, the combination therapy can include one or more antibodies and antigen-binding fragments thereof coformulated with, and/or coadministered with, one or more additional therapeutic agents, e.g., one or more cytokine and growth factor inhibitors, immunosuppressants, anti-inflammatory agents, metabolic inhibitors, enzyme inhibitors, antineoplastic agents, and/or cytotoxic or cytostatic agents, as described in more detail below. Such combination therapies may advantageously utilize lower dosages of the administered therapeutic agents, thus avoiding possible toxicities or complications associated with the various monotherapies.

Preferred therapeutic agents used in combination with an antibody of the invention are those agents that interfere at different stages in an inflammatory response. In one embodiment, one or more antibodies described herein may be coformulated with, and/or coadministered with, one or more additional agents such as other cytokine or growth factor antagonists (e.g., soluble receptors, peptide inhibitors, small molecules, ligand fusions); or antibodies or antigen binding fragments thereof that bind to other targets (e.g., antibodies that bind to other cytokines or growth factors, their receptors, or other cell surface molecules); and anti-inflammatory cytokines or agonists thereof.

Design and Generation of Other Therapeutics

In accordance with the present invention and based on the activity of the antibodies that are produced and characterized herein with respect to Frizzled receptors, the design of other therapeutic modalities beyond antibody moieties is facilitated. Such modalities include, without limitation, advanced antibody therapeutics, such as bispecific antibodies, immunotoxins, and radiolabeled therapeutics, generation of peptide therapeutics, gene therapies, particularly intrabodies, antisense therapeutics, and small molecules.

For example, in connection with bispecific antibodies, bispecific antibodies can be generated that comprise (i) two antibodies-one with a specificity to one or more Frizzled receptors and another to a second molecule that are conjugated together, (ii) a single antibody that has one chain specific to one or more Frizzled receptors and a second chain specific to a second molecule, or (iii) a single chain antibody that has specificity to one or more Frizzled receptors and a second molecule. Such bispecific antibodies are generated using techniques that are well known for example, in connection with (i) and (ii) See e.g., Fanger et al. Immunol Methods 4:72-81 (1994) and Wright et al. Crit, Reviews in Immunol. 12125-168 (1992), and in connection with (iii) See e.g., Traunecker et al. Int. J. Cancer (Suppl.) 7:51-52 (1992).

In connection with immunotoxins, antibodies can be modified to act as immunotoxins utilizing techniques that are well known in the art. See e.g., Vitetta Immunol Today 14:252 (1993). See also U.S. Pat. No. 5,194,594. In connection with the preparation of radiolabeled antibodies, such modified antibodies can also be readily prepared utilizing techniques that are well known in the art. See e.g., Junghans et al. in Cancer Chemotherapy and Biotherapy 655-686 (2d edition, Chafner and Longo, eds., Lippincott Raven (1996)). See also U.S. Pat. Nos. 4,681,581, 4,735,210, 5,101,827, 5,102,990 (RE 35,500), 5,648,471, and 5,697,902. Each of immunotoxins and radiolabeled molecules would be likely to kill cells expressing one or more Frizzled receptors.

In connection with the generation of therapeutic peptides, through the utilization of structural information related to one or more Frizzled receptors and antibodies thereto, such as the antibodies and antigen-binding fragments thereof or screening of peptide libraries, therapeutic peptides can be generated that are directed against one or more Frizzled receptors. Design and screening of peptide therapeutics is discussed in connection with Houghten et al. Biotechniques 13:412-421 (1992), Houghten PNAS USA 82:5131-5135 (1985), Pinalla et al. Biotechniques 13:901-905 (1992), Blake and Litzi-Davis BioConjugate Chem. 3:510-513 (1992). Immunotoxins and radiolabeled molecules can also be prepared, and in a similar manner, in connection with peptidic moieties as discussed above in connection with antibodies. Assuming that the Frizzled receptor molecule (or a form, such as a splice variant or alternate form) is functionally active in a disease process, it will also be possible to design gene and antisense therapeutics thereto through conventional techniques. Such modalities can be utilized for modulating the function of one or more Frizzled receptors. In connection therewith the antibodies of the present invention facilitate design and use of functional assays related thereto. A design and strategy for antisense therapeutics is discussed in detail in International Patent Application No. WO 94/29444. Design and strategies for gene therapy are well known. However, in particular, the use of gene therapeutic techniques involving intrabodies could prove to be particularly advantageous. See e.g., Chen et al. Human Gene Therapy 5:595-601 (1994) and Marasco Gene Therapy 4:11-15 (1997). General design of and considerations related to gene therapeutics is also discussed in International Patent Application No. WO 97/38137.

Knowledge gleaned from the structure of one or more targeted Frizzled receptor molecules and its/their interactions with other molecules in accordance with the present invention, such as the antibodies and antigen-binding fragments thereof, and others can be utilized to rationally design additional therapeutic modalities. In this regard, rational drug design techniques such as X-ray crystallography, computer-aided (or assisted) molecular modeling (CAMM), quantitative or qualitative structure-activity relationship (QSAR), and similar technologies can be utilized to focus drug discovery efforts. Rational design allows prediction of protein or synthetic structures which can interact with the molecule or specific forms thereof which can be used to modify or modulate the activity of one or more Frizzled receptors. Such structures can be synthesized chemically or expressed in biological systems. This approach has been reviewed in Capsey et al. Genetically Engineered Human Therapeutic Drugs (Stockton Press, N.Y. (1988)). Further, combinatorial libraries can be designed and synthesized and used in screening programs, such as high throughput screening efforts.

Screening Methods

The invention provides methods (also referred to herein as "screening assays") for identifying modulators, i.e., candidate or test compounds or agents (e.g., peptides, peptidomimetics, small molecules or other drugs) that modulate or otherwise interfere with the binding of one or more Frizzled receptors to a Wnt protein ligand and/or with Frizzled activation, or candidate or test compounds or agents that modulate or otherwise interfere with Wnt signaling function. Also provided are methods of identifying compounds useful to treat disorders associated with aberrant Frizzled receptor activity, activation, expression and/or phosphorylation. The invention also includes compounds identified in the screening assays described herein.

In one embodiment, the invention provides assays for screening candidate or test compounds which modulate a function of one or more Frizzled receptors. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. (See, e.g., Lam, 1997. Anticancer Drug Design 12: 145).

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. Proc. Natl. Acad. Sci. U.S.A. 90: 6909; Erb, et al., 1994. Proc. Natl. Acad. Sci. U.S.A. 91: 11422; Zuckermann, et al., 1994. J. Med. Chem. 37: 2678; Cho, et al., 1993. Science 261: 1303; Carrell, et al., 1994. Angew. Chem. Int. Ed. Engl. 33: 2059; Carell, et al., 1994. Angew. Chem. Int. Ed. Engl. 33: 2061; and Gallop, et al., 1994. J. Med. Chem. 37: 1233.

Libraries of compounds may be presented in solution (see e.g., Houghten, 1992. Biotechniques 13: 412-421), or on beads (see Lam, 1991. Nature 354: 82-84), on chips (see Fodor, 1993. Nature 364: 555-556), bacteria (see U.S. Pat. No. 5,223,409), spores (see U.S. Pat. No. 5,233,409), plasmids (see Cull, et al., 1992. Proc. Natl. Acad. Sci. USA 89: 1865-1869) or on phage (see Scott and Smith, 1990. Science 249: 386-390; Devlin, 1990. Science 249: 404-406; Cwirla, et al., 1990. Proc. Natl. Acad. Sci. U.S.A. 87: 6378-6382; Felici, 1991. J. Mol. Biol. 222: 301-310; and U.S. Pat. No. 5,233,409.).

In one embodiment, a candidate compound is introduced to an antibody-antigen complex and determining whether the candidate compound disrupts the antibody-antigen complex, wherein a disruption of this complex indicates that the candidate compound modulates a function of one or more Frizzled receptor and/or the interaction between one or more Frizzled receptors and a Wnt protein ligand.

Determining the ability of the test compound to interfere with or disrupt the antibody-antigen complex can be accomplished, for example, by coupling the test compound with a radioisotope or enzymatic label such that binding of the test compound to the antigen or biologically-active portion thereof can be determined by detecting the labeled compound in a complex. For example, test compounds can be labeled with $^{125}$I, $^{35}$S, $^{14}$C, or $^{3}$H, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product.

In one embodiment, the assay comprises contacting an antibody-antigen complex with a test compound, and determining the ability of the test compound to interact with the antigen or otherwise disrupt the existing antibody-antigen complex. In this embodiment, determining the ability of the test compound to interact with the antigen and/or disrupt the antibody-antigen complex comprises determining the ability of the test compound to preferentially bind to the antigen or a biologically-active portion thereof, as compared to the antibody.

In another embodiment, the assay comprises contacting an antibody-antigen complex with a test compound and determining the ability of the test compound to modulate the antibody-antigen complex. Determining the ability of the test compound to modulate the antibody-antigen complex can be accomplished, for example, by determining the ability of the antigen to bind to or interact with the antibody, in the presence of the test compound.

The screening methods disclosed herein may be performed as a cell-based assay or as a cell-free assay. The cell-free assays of the invention are amenable to use of either the soluble form or the membrane-bound form of one or more Frizzled receptors, and fragments thereof. In the case of cell-free assays comprising the membrane-bound forms of one or more Frizzled receptors, it may be desirable to utilize a solubilizing agent such that the membrane-bound form of the proteins are maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, N-dodecyl--N,N-dimethyl-3-ammonio-1-propane sulfonate, 3-(3-cholamidopropyl)dimethylamminiol-1-propane sulfonate (CHAPS), or 3-(3-cholamidopropyl)dimethylamminio1-2-hydroxy-1-propane sulfonate (CHAPSO).

In more than one embodiment, it may be desirable to immobilize either the antibody or the antigen to facilitate separation of complexed from uncomplexed forms of one or both following introduction of the candidate compound, as well as to accommodate automation of the assay. Observation of the antibody-antigen complex in the presence and absence of a candidate compound can be accomplished in any vessel suitable for containing the reactants. Examples of such vessels include microtiter plates, test tubes, and microcentrifuge tubes. In one embodiment, a fusion protein can be provided that adds a domain that allows one or both of the proteins to be bound to a matrix. For example, GST-antibody fusion proteins or GST-antigen fusion proteins can be adsorbed onto glutathione sepharose beads (Sigma Chemical, St. Louis, Mo.) or glutathione derivatized microtiter plates, that are then combined with the test compound, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly. Alternatively, the complexes can be dissociated from the matrix, and the level of antibody-antigen complex formation can be determined using standard techniques.

Other techniques for immobilizing proteins on matrices can also be used in the screening assays of the invention. For example, either the antibody (e.g. the anti-Frizzled receptor antibodies and fragments of the invention) or the antigen (e.g. one or more Frizzled receptors) can be immobilized utilizing conjugation of biotin and streptavidin. Biotinylated antibody or antigen molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, other antibodies reactive with the antibody or antigen of interest, but which do not interfere with the formation of the antibody-antigen complex of interest, can be derivatized to the wells of the plate, and unbound antibody or antigen trapped in the wells by antibody conjugation. Methods for detecting such complexes, in addition to those described above for the GST-immobilized complexes, include immunodetection of complexes using such other antibodies reactive with the antibody or antigen.

The invention further pertains to novel agents identified by any of the aforementioned screening assays and uses thereof for treatments as described herein.

Diagnostic and Prophylactic Formulations

The anti-Frizzled antibodies and fragments of the invention are used in diagnostic and prophylactic formulations. In one embodiment, an anti-Frizzled antibody or fragment of the invention is administered to patients that are at risk of developing one or more of the aforementioned diseases, such as for example, without limitation, cancer and/or inflammatory disorders. A patient's or organ's predisposition to one or more of these diseases can be determined using genotypic, serological or biochemical markers.

Antibodies and antigen-binding fragments thereof are also useful in the detection of one or more Frizzled receptors in patient samples and accordingly are useful as diagnostics. For example, the anti-Frizzled receptor antibodies and fragments of the invention are used in in vitro assays, e.g., ELISA, to detect Frizzled receptor levels in a patient sample.

In one embodiment, an anti-Frizzled receptor antibody or fragment of the invention is immobilized on a solid support (e.g., the well(s) of a microtiter plate). The immobilized antibody serves as a capture antibody for any Frizzled receptor that may be present in a test sample. Prior to contacting the immobilized antibody with a patient sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of Frizzled receptor antigen in the test sample is determined by comparison with a standard curve developed from the standard samples.

It will be appreciated that based on the results obtained using the anti-Frizzled receptor antibodies and fragments of the invention in an in vitro diagnostic assay, it is possible to stage a disease (e.g., a clinical indication associated with cancer or inflammatory disorder) in a subject based on expression levels of the Frizzled receptor antigen. For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

The following examples, including the experiments conducted and results achieved are provided for illustrative purposes only and are not to be construed as limiting upon the present invention.

Example 1: Materials and Methods

Phage display selection: Phage display selections were performed on recombinant human FZD7 extracellular domains (R&D Systems) according to the procedure described by Sachdev S. Sidhu and Frederic A. Fellouse. "Synthetic therapeutic antibodies." *Nat Chem Biol.* 2(12) (2006):682-8.

Fab expression and purification: IPTG-inducible expression plasmids were used for the production of Fabs in BL21 bacterial cells. Briefly, 25 ml overnight bacterial cultures are back diluted in 1 L 2YT media. At an O.D.=1 cells were induced with a final concentration of 1 mM IPTG. After 4 hours of induction the cells were collected by centrifugation and the pellets were frozen at −20° C. The next day pellets were resuspended in 40 ml lysis buffer (1% Triton X-100, 2 mM $MgCl_2$, 0.2 mM PMSF, 0.1% (w/v) lysozyme and 1 ul benzonase (2.5 U/ml) prior to lysis at 4° C. for 1 hour. The Fab containing supernatant was separated from cell debris by centrifugation at 11000 RPM for 45 min. Fabs were captured at 4° C. for 1 hour with Sepharose A beads, using 1 ml bead volume per 40 ml Fab solution. The beads were collected in 25 ml columns (Biorad), followed by 3×10 ml PBS washes. Fabs were eluted with 8 ml of elution buffer (50 mM $NaH_2PO_4$, 100 mM $H_3PO_4$, 140 mM NaCl, pH 2.8) and neutralized with Tris-HCl pH 8.0 at a final concentration of 200 mM. PBS buffer exchange was carried out using standard dialysis.

IgG expression and purification: IgG was expressed in 293 F cells and purified from the condition media according to conventional methodology. Briefly, equal amounts of DNA constructs encoding light chain or heavy chain were co-transfected into 293 F cells. The cell culture condition media were harvested 120-145 hours post transfection. Appropriate amount of Protein A beads were added to the condition media and mixed at room temperature for 1-2 hours. The supernatant was removed and the beads were washed 3 times with PBS and the IgG was then eluted with elution buffer (0.1 M Glycine-HCl, pH 2.7) and neutralized with neutralization buffer (1 M Tris-HCl, pH 9.0). The purified IgG was then dialysed and buffer exchanged into PBS.

ELISA assays: Binding of the Fabs were assessed by immobilizing 100 nM FZD7 antigen and Fc control protein for 1 hour at RT, followed by an 1 hour blocking step in 60 ul of PBS-BSA solution (for details see Sachdev S. Sidhu and Frederic A. Fellouse. "Synthetic therapeutic antibodies." *Nat Chem Biol.* 2(12)(2006):682-8). After blocking 100 nM Fab was added to each well, incubated for 30 min, washed 6 times with PBS-Tween buffer and detected with anti-FLAG-HRP (1:5000 dilution).

Affinity measurement using Surface Plasmon Resonance (SPR): For kinetic analysis, Fab proteins were purified from *Escherichia coli*. Binding kinetics were determined by surface plasmon resonance using a PROTEON (BioRAD) with antigen immobilized on GLC chips at a density sufficient to produce ~100 response units when saturated with Fab. Serial dilutions of Fab proteins were injected at 100 ul minute for 1 minute. PBS was then injected at 100 ul/minute for 10 minutes to observe dissociation. Binding responses were corrected by subtraction of responses on a blank flow cell. For kinetic analysis, a 1:1 Langmuir model of global fittings of $k_{on}$, and $k_{off}$ was used. The $K_d$ values were determined from the ratios of $k_{on}$, and $k_{off}$.

Epitope binning: Briefly, 100 nM immobilized antigen was pre-incubated with 500 nM purified Fab for 1 hour. Freshly prepared phage, carrying the anti-FZD7 Fab molecules, were added to the antigen-Fab complex containing wells. Fabs that block overlapping phage-Fab-antigen interactions were grouped together. For details see Sachdev S. Sidhu and Frederic A. Fellouse. "Synthetic therapeutic antibodies." *Nat Chem Biol.* 2(12) (2006):682-8.

Cell surface binding by flow cytometry: Cells are collected by EDTA solution and wash with PBS once, aliquot to 0.2-1×10$^6$ cells per sample; the cells were incubated with tested antibody (1 μg ab per sample in 100 ul PBS-0.5% BSA) for 60 min on ice; Cells were then washed with 1 ml PBS-0.1% BSA twice and incubated with 100 ul Goat anti-Human Fab-488 diluted in PBS-0.1% BSA for 1530 min at RT, in the dark. Cells were then washed with 1 ml PBS-0.1% BSA twice before re-suspended in filtered 0.2-0.5 ml 4% Paraformaldehyde. The cell samples are subjected to FACS analysis immediately or, to be kept at 4° C. for later analysis. Secondary Ab used: Alexa Fluor® 488 goat anti-human Fab (Jackson #109-546-097) 1:1000 EDTA Solution (for detach adherent cells): 0.15 g disodium EDTA (1 mM), 4.0 g NaCl, 0.28 g sodium bicarbonate, 0.5 g dextrose (D-glucose), 0.2 g KCl, Dissolved in 500 ml double distilled water.

TopFlash reporter assay: Lentivirus containing the Top-Flash β-catenin-dependent luciferase reporter (firefly luciferase) and Renilla luciferase were used to establish stable MDA-MB-231 and HEK293T Wnt-reporter lines. Twenty-four hours prior treatments, cells were seeded on 24-well plate at 50% confluency in a final volume of 500 ul. The following day, half of the media was replaced with 250 μl of Wnt3a or control conditioned media from L cells and Fabs or IgGs were added at the desired concentration. The cells were then assayed 15 hours after stimulation in accordance with the dual luciferase protocol (Promega) using an Envision multilabel plate reader (Perkin-Elmer).

Immunofluorescence staining: Lentivirus containing the CRD of FZD receptors fused to a myc tag and a GPI anchor sequence were used to establish stable CHO cells. CHO stable cell lines or MDA-MB-231 cells were seeded on coverslips and incubated 1 hour at 4° C. in DMEM, 10% FBS, 1% Pen/Strep in presence of 200 nM of Fabs or IgG or 1:200 dilution of anti-cMyc (SantaCruz). Cells were fixed for 15 minutes in 3.7% paraformaldehyde and block with 10% normal donkey serum (NDS) for 30 minutes and incubated with secondary anti-Fab 488 Alexa fluor (Jackson) or anti-rabbit 488 Alexa Fluor (Molecular Probe) with 0.1% NDS for 60 minutes at room temperature. Coverslips were mounted with Vectashield (Vector Laboratories Inc) containing DAPI and imaged with a Nikon Eclipse 80i or a LSM 700 (Zeiss).

The Sulforhodamine B (SRB) assay to measure cell growth: Cancer cells were plated in a 96 well plate with the following densities: ASPC1 at 1800/well, HPAFII at 1500/well, CAPAN2 at 3000/well and IMIMPC2 at 600/well. Cells were cultured overnight, followed by the addition of anti-FZD7 IgGs to the cells in a total volume of 100 μl of culture medium and kept in the incubator for 5 days. The cells were subsequently fixed in situ by gently aspirating off the culture medium, followed by the addition of 50 μl of ice cold 10% TAC (Tri-chloroacetic Acid) to each well and incubated at 4° C. for 30-60 min.

The plates were washed with tap water five times and allowed to air dry for 5 minutes. Subsequently, 50 μl of 0.4% Sulforhodamine B solution in 1% acetic acid were added to each well and incubated for 30 min at room temperature for staining. Following staining, plates were washed four times with freshly-made 1% acetic acid to remove any unbound dye and then allowed to air dry for 5 mins. The stain was solubilized with 100 μl of 10 mM Tris (PH 10.5) per well. The plate was then placed on an orbital rotator for 5 minutes before Absorbance was read at 570 nm.

Cell culture: Human pancreatic adenocarcinoma cell lines, AsPC-1, CAPAN2 and HPAFII were purchased from the American Type Culture Collection (Manassas, Va., USA). The AsPC-1 cells were maintained in RPMI1640 medium (Life Technologies, Grand Island, N.Y., USA. Cat #: A10491-01) supplemented with 10% FCS (Life Technologies, Grand Island, N.Y., USA. Cat #: 12483-020), 100 U/ml of penicillin and 100 U/ml streptomycin (Life Technologies, Grand Island, N.Y., USA. Cat #: 15140-122) at 37° C. in a humidified atmosphere containing 5% $CO_2$.

The CAPAN2 cells were maintained in McCoy's 5a medium (Life Technologies, Grand Island, N.Y., USA. Cat #: 16600) supplemented with 10% FCS (Life Technologies, Grand Island, N.Y., USA. Cat #: 12483-020), 100 U/ml of penicillin and 100 U/ml streptomycin (Life Technologies, Grand Island, N.Y., USA. Cat #: 15140-122) at 37° C. in a humidified atmosphere containing 5% $CO_2$.

The HPAFII cells were maintained in EMEM medium (Wisent Inc., St-Bruno, QC, Canada. Cat #: 320-026-CL) supplemented with 10% FCS (Life Technologies, Grand Island, N.Y., USA. Cat #: 12483-020), 100 U/ml of penicillin and 100 U/ml streptomycin (Life Technologies, Grand Island, N.Y., USA. Cat #: 15140-122) at 37° C. in a humidified atmosphere containing 5% $CO_2$.

The cells were confirmed to be free from mycoplasma by periodic testing with a MycoAlert® Mycoplasma Detection Kit (Lonza, Rockland, Me., USA. Cat #: LT07-318).

Test Antibodies (for in vivo experiments): Five recombinant anti-Frizzled 7 antibodies (FZD7 Abs) were tested in these experiments. These antibodies were A1 (mAb #105), E4 (mAb #107), H10 (mAb #111), H1 (mAb #112) and G2 (mAb #140). Each antibody was diluted from its stock concentration with vehicle buffer to the dose concentration (1.33 mg/ml—equal to 20 mg/kg at a dose volume of 15 ml/kg). Vehicle buffer was DPBS (without calcium and magnesium, Life Technologies, Grand Island, N.Y., USA. Cat #: 14190-144) containing 5% of d-(+)-Trehalose Dihydrate (Bioshop, Burlington, ON, Canada. Cat #: TRE222).

For the dose response study, two anti-Frizzled antibodies (FZD7 Abs), Ab 111 and Ab 112, were tested with 3 different dose levels (50, 20 and 5 mg/kg) in these experiments. Each antibody was diluted from its stock concentration with vehicle buffer to the dose concentrations (3.33, 1.33 and 0.33 mg/ml—equal to 50, 20 and 5 mg/kg respectively at a dose volume of 15 ml/kg). Vehicle buffer was DPBS (without calcium and magnesium, Life Technologies, Grand Island, N.Y., USA. Cat #: 14190-144) containing 5% of d-(+)-Trehalose Dihydrate (Bioshop, Burlington, ON, Canada. Cat #: TRE222).

For testing in CAPAN2 and HPAFII xenograft models, anti-Frizzled 7 antibody (FZD7 Ab), Ab111, was tested with 2 different dose levels (20 and 5 mg/kg) in these experiments. The antibody was diluted from its stock concentration with vehicle buffer to the dose concentrations (1.33 and 0.33 mg/ml—equal to 20 and 5 mg/kg respectively at a dose volume of 15 ml/kg). Vehicle buffer was DPBS (without calcium and magnesium, Life Technologies, Grand Island, N.Y., USA. Cat #: 14190-144).

Example 2: Selection, Generation and Characterization of Fabs Against Frizzled Receptors A synthetic Fab phage display library referred to as "Library F" was used to generate antibodies against Frizzled receptors. Using recombinant Frizzled receptor 7 (FZD7) cysteine-rich domain (CRD) fused to the Fc region of human IgG as the antigen, four rounds of sequential selection with Library F were performed, and multiple phage Fab clones that specifically bind to the FZD7-CRD-Fc but not Fc control were identified (see Materials and Methods).

Library F is a single framework human Fab library constructed similarly to previously described libraries. (See e.g., Fellouse F A, Pal G, "Methods for the Construction of Phage-Displayed Libraries" in Phage Display in Biotechnology and Drug Discovery. Boca Raton: CRC Press (2005); and Fellouse F A et al. "High-throughput generation of synthetic antibodies from highly functional minimalist phage-displayed libraries." J Mol Biol 373 (2007): 924-940).

Library F is an Fab-phage library that was constructed by introducing degenerate codons into positions in CDR-H1, CDR-H2, CDR-H3 and CDR-L3 of a single human Fab framework. The loop length of the CDR-L3 and/or CDR-H3 in Library F can vary as shown in the table below. In this library, CDR-L1 includes the amino acid sequence SVSSA (SEQ ID NO: 392) and the CDR L2 includes the amino acid sequence SASSLYS (SEQ ID NO: 393). The library has a total diversity of $3 \times 10^{10}$ unique clones, and the details of the library design are shown in Table 1 below, where the bolded positions in the CDR-L3 and CDR-H3 regions represent positions that were replaced by random loops of all possible varying lengths, as indicated.

TABLE 1

CDR Sequences of Library F clones

| CDR L3 (SEQ ID NO: 394) | | | | | | | | | |
|---|---|---|---|---|---|---|---|---|---|
| Position | 91 | 92 | 93 | 94 | 95 | 96 | | | |
| | Z | Z | Z | Z | PL | IL | | | |

Z = 25% Y, 20% S, 20% G, 10% A and 5% each of F, W, H, P, V
Loop Length (8-12 aa)

| CDR H1 (SEQ ID NO: 395) | | | | | | | | | |
|---|---|---|---|---|---|---|---|---|---|
| Position | 29 | 30 | 31 | 32 | 33 | 34 | | | |
| | IL | YS | YS | YS | YS | IM | | | |

| CDR H2 (SEQ ID NO: 396) | | | | | | | | | |
|---|---|---|---|---|---|---|---|---|---|
| Position | 50 | 51 | 52 | 52a | 53 | 54 | 55 | 56 | 57 | 58 |
| | YS | I | YS | PS | YS | YS | GS | YS | T | YS |

| CDR H3 (SEQ ID NO: 397) | | | | | | | | | | |
|---|---|---|---|---|---|---|---|---|---|---|
| Position | 94 | 95 | 96 | 97 | 98 | 99 | 100 | 100a | 100b | 100c | 101 |
| | R | Z | Z | Z | Z | Z | Z | Z | AG | FILM | D |

Z = 25% Y, 20% S, 20% G, 10% A and 5% each of F, W, H, P, V
Loop Length (5-22 aa)

Sequencing and sequence analysis of these clones led to identification of 61 Fab clones with unique sequences (FIG. 1). These clones were then cloned into IPTG-inducible E. coli expression vector, and Fab proteins were expressed and purified (FIG. 2A). It was confirmed that these purified anti-FZD7 Fabs bind to the FZD7-CRD-Fc, but not to the Fc control (FIG. 2B).

The binding of the purified Fabs to the FZD7 expressed on cells was tested. To see if these Fabs recognize the FZD7 receptor expressed on cells, a flow cytometry analysis was performed. The Fabs, except Fabs A2, A12, C3, E3 and E7, bound to cells that are known to express FZD7 as well as to the same cells that have been engineered to over-express FZD7 (FIG. 3). The Fabs that showed good binding in the flow cytometry assay were selected and purified for further analysis.

The binding specificity of the Fab phage clones was tested. To determine if these Fab clones also bound to other Frizzled receptors, phage binding ELISA assay was carried out using purified FZD ECD-Fc fusion proteins. This analysis demonstrated that, in addition to FZD7, the Fab phage clones also bound to other Frizzled receptors (FIG. 4A). The binding specificities of these Fabs were further determined by immunofluorescence staining using cells overexpressing individual FZD ECDs. Fabs A1, D10, E4, G2, H3 and H10 shared the same binding specificity profile, which is different from those of Fab E8, G6 or H1 (FIG. 4B).

Next, epitope binning of the anti-FZD Fabs was performed. To learn if the anti-FZD7 Fabs share binding sites on the antigen FZD7, competitive ELISA assays were performed to determine if purified Fabs would competes with Fab phage clones for binding to the antigen (FZD7 CRD-Fc). These experiments showed that Fab effectively competed with its own corresponding phage clone (FIG. 5). In addition, Fabs G6, H1, A1 and E4 effectively blocked binding of all other Fab phage clones, while Fab D10 only effectively blocked the binding of Fab phage clone E8 (FIG. 5), suggesting these Fabs share overlapping binding sites on FZD7.

Next, the affinity of the anti-FZD7 Fabs was determined by Surface Plasmon Resonance (SPR). SPR was used to determine the binding affinity of the FZD7 Fabs to FZDs. FIG. 6, which summarizes the binding affinity obtained by SPR, demonstrates that the affinity values of these Fabs for FZD7 ranged from 0.4-9 nM. Binding affinity for a subset of additional FZDs was also obtained (FIG. 7).

Figure 8:
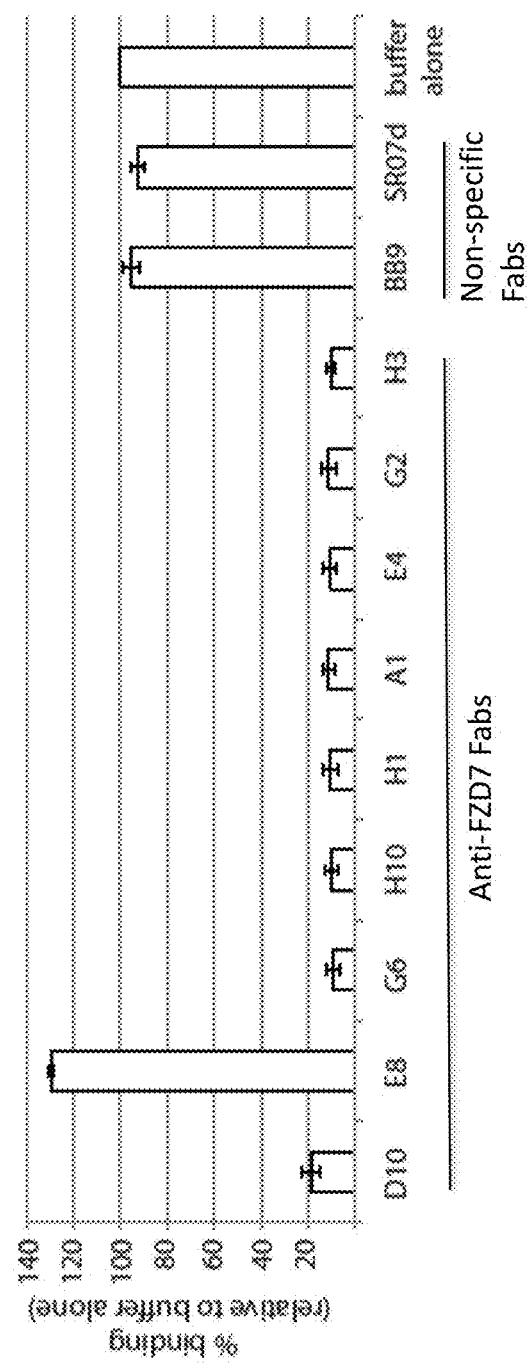
FIG. 8 is a graph depicting the inhibition of Wnt5a binding by anti-FZD7 Fabs. Wnt 5a (R&D systems) was biotinylated using a commercial kit (Thermo 21329 EZ-link NHS-PEG4-Biotin) and excess biotin was removed by buffer exchange using a 3000MWCO Amicon filter. Fzd7-Fc was diluted in 1% BSA/PBS (dilution buffer) and incubated with desired Fab or buffer samples for 1 hour at room temperature in 96-well TC plates pre-blocked with 1% BSA. Control wells with Fc protein were also included. Biotinylated wnt5a was added to the wells and plates were incubated for an additional hour. Control wells in which buffer alone was added in lieu of biotinylated wnt5a were also included. Biotinylated Wnt5a was added at a final concentration of 150 ng/ul, Fab proteins were at a final concentration of 0.5 µM, and Fzd7-Fc was at a final concentration previously determined to give absorbance readings within the linear range. Fabs BB9 and SR07d were included as negative control samples given their specificity for other protein antigens. Samples were transferred to pre-blocked streptavidin coated plates (R&D systems) and allowed to capture for 1 hour at room temperature. Wells were washed four times with 0.05% Tween20/PBS and then anti-Fc-HRP (1:5000 in dilution buffer, Jackson Immuno) was added to the wells for 45 min at room temperature. Wells were washed four times and developed with TMB reagent with an acid stop. The absorbance at 450 nm was read and the percent binding was calculated as the A450 of the desired Fab well divided by the A450 of the buffer alone well, multiplied by 100. Error bars represent three independent ELISA experiments.
Figure 9:
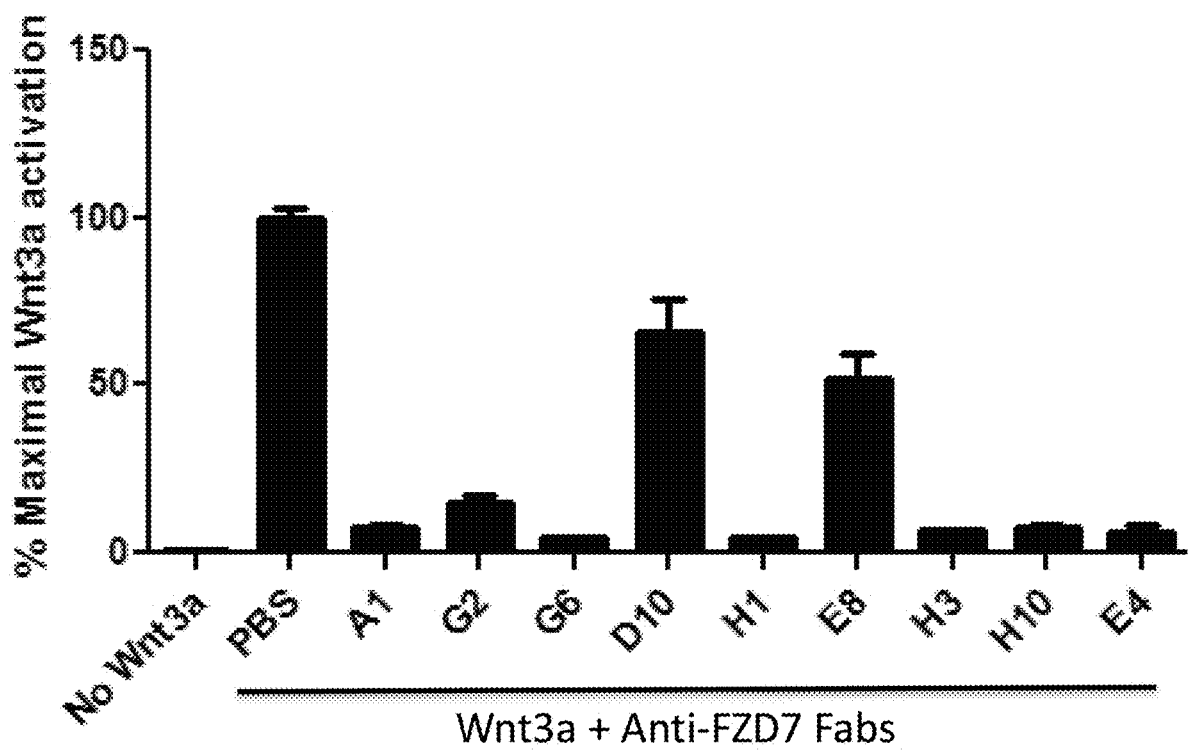
FIG. 9 is a graph depicting the effect of anti-FZD7 Fabs on the Wnt3a-induced transcriptional activity. A TOP-FLASH receptor system (TCF/LEF binding sites are linked to a luciferase reporter gene) was stably introduced into MDA MB 231 cells. Fabs at a final concentration of 400 nM were incubated for 15 hours with Wnt3a conditioned media and appropriate control wells. Wells were lysed and luciferase signals were read. Error bars represent n=3.

The effect of the anti-FZD Fabs on Wnt ligand binding and ligand-induced transcription was analyzed. An ELISA assay was used to directly determine if the Fabs were able to block Wnt ligand binding to FZD7. As shown in FIG. 8, Fabs A1, D10, E4, G2, H3, H10, G6 or H1 effectively inhibited ligand Wnt 5a binding. But Fab E8 did not block the binding of Wnt5a to FZD7. Further, in a transcriptional reporter assay, Fabs A1, G2, H1, H3, H10 and E4 inhibited Wnt 3a-induced transcriptional activity by more than 70% in comparison to the PBS control (FIG. 9).

The effect of anti-FZD mAb (IgGs) on ligand Wnt3a-induced transcriptional activity was also analyzed. The anti-FZD Fabs were converted into full-length antibodies as IgG$_1$, and the mAbs were expressed and purified from mammalian cells. The purified antibodies were subsequently used for biochemical and biological characterization studies.

Figure 10:
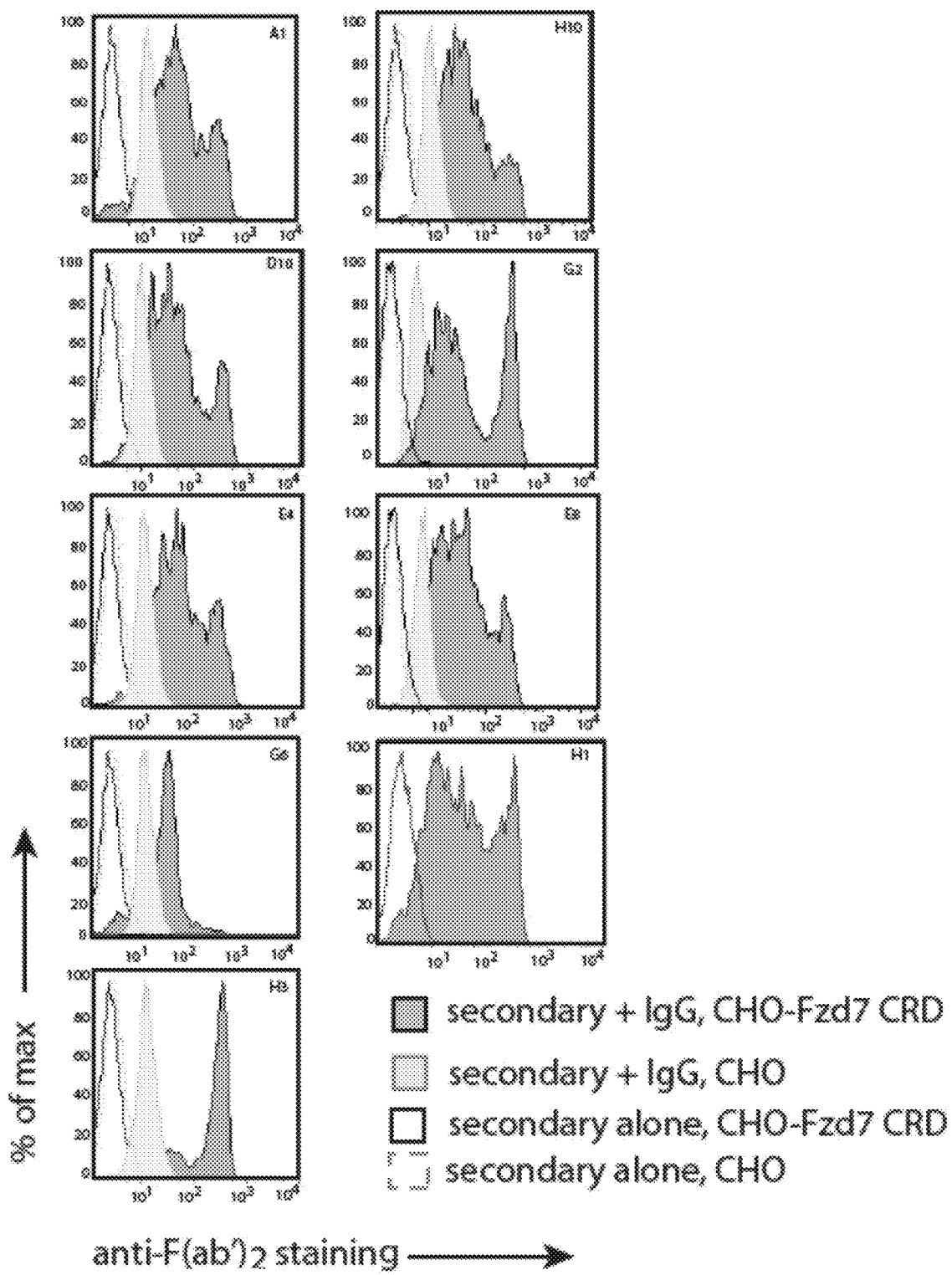
FIG. 10 is a series of graphs depicting the binding of anti-FZD7 IgGs to FZD7 ECD expressed on cell surface. Anti-Fzd7 IgGs were stained by flow cytometry at 25 nM on indicated cell-lines. IgGs were detected using an anti-F(ab) 2-FITC labeled secondary antibody (Jackson Immuno), fixed with PFA, and then data was acquired on a BD facscalibur.

First the binding affinities of these mAbs to FZD7 were determined using SPR method (see Materials and Methods). As shown in FIG. 7, K$_D$ values were estimated ranging from 0.2-1.5 nM. Second, the antibodies were examined in a flow cytometry analysis to determine if these mAbs bind to FZD7 expressed on cells. The antibodies were shown to be bind to the FZD7-overexpressing CHO cells better than CHO cells, indicating the antibodies recognized FZD7 expressed on cells (FIG. 10).

Figure 11:
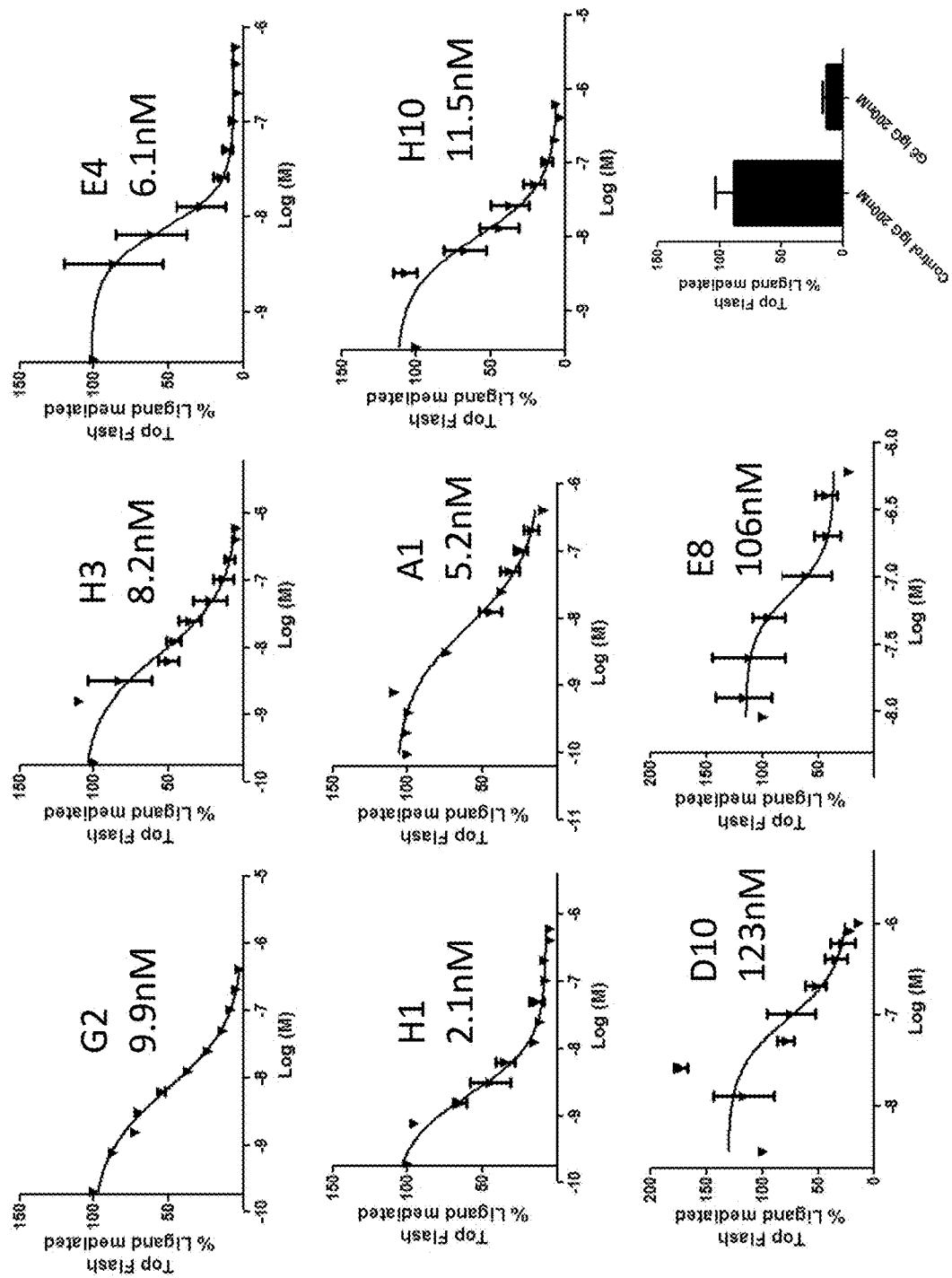
FIG. 11 is a series of graphs depicting the effect of anti-FZD7 IgGs on Wnt3a-induced transcription. Dose-dependent inhibition curves are shown. The $IC_{50}$ values are indicated. For IgG G6, only single dose inhibition was done. At 200 nM, IgG G6 shows >70%.

The anti-FZD7 antibodies were also tested in a ligand (Wnt3a)-dependent transcriptional reporter assay to see if they blocked signal transduction mediated by Wnt ligand and FZD7. As shown in FIG. 11, IgGs A1, G2, H1, H3, E4, D10, H10 and E8 inhibited Wnt 3a-induced transcriptional activity in a dose-dependent manner. The IC$_{50}$ values were estimated ranging from 2 nM to 125 nM (FIG. 11).

Example 3: In vitro Assessment of Tumor Response Following Administration of Anti-FZD7 mAbs Human pancreatic cancer cell lines, ASPC1, HPAFII, CAPAN2 and IMMIPC2 were used to assess the response of cancer cell proliferation following treatment with anti-FZD7 mAbs. For these studies the pancreatic cell lines were plated in 96 well plates at the following densities: ASPC1 cells were plated at 1800 cells/well, HPAFII cells were plated at 1500 cells/well, CAPAN2 cells were plated at 3000 cells/well, and IMMIPC2 cells were plated at 600 cells per well. Following an overnight culture period, anti-FZD7 mAbs (H10 (mAb #111), G2 (mAb #140), A1 (mAb #105), E4 (mAb #107), or 18R5) or as a negative control, human gamma globulin, were added to the cells for 5 days.

Figure 12A:
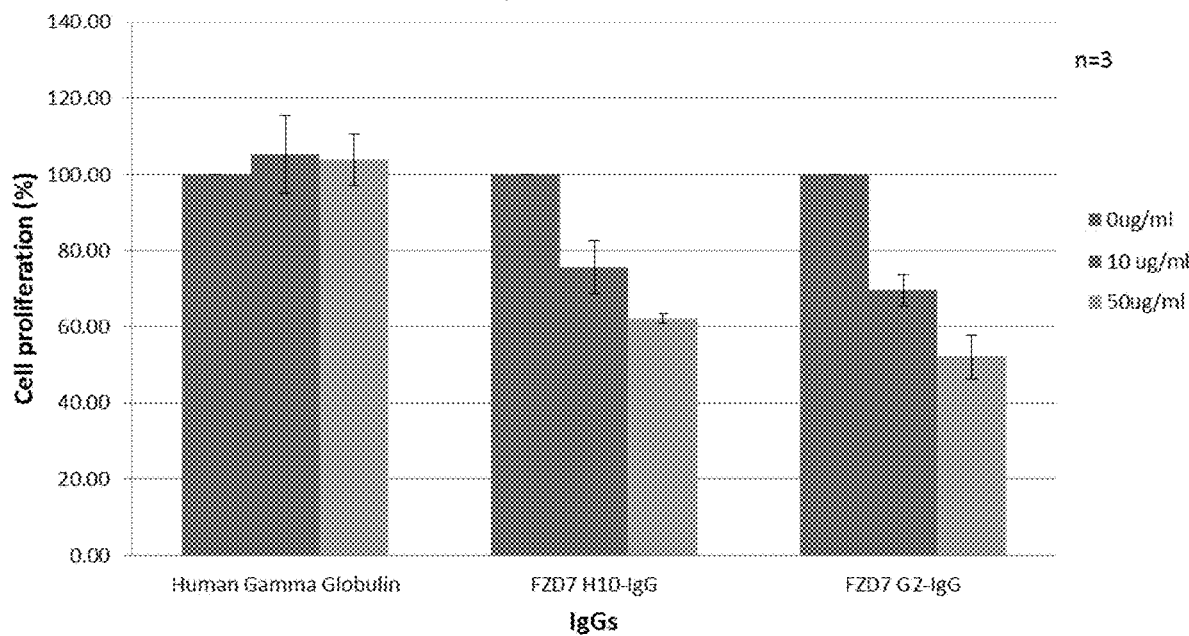
FIG. 12A-12E are a series of graphs and tables depicting a dose dependent decrease in the proliferation of pancreatic cancer cell lines following 5 days of exposure to anti-FZD7 monoclonal antibodies.
Figure 12B:
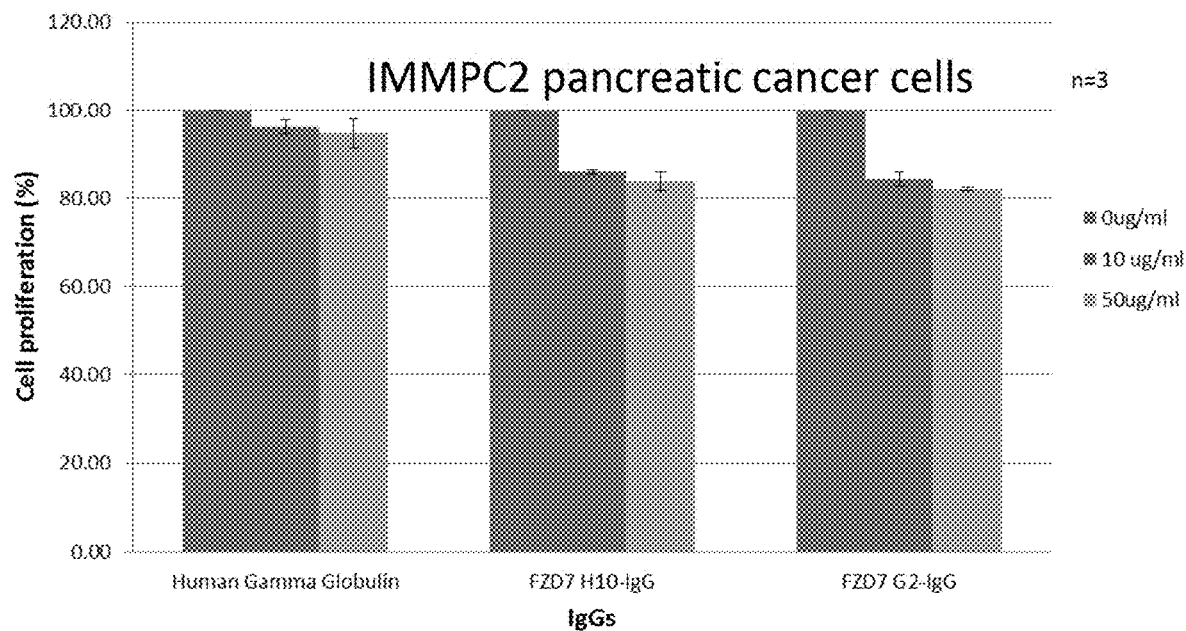
Figure 12C:
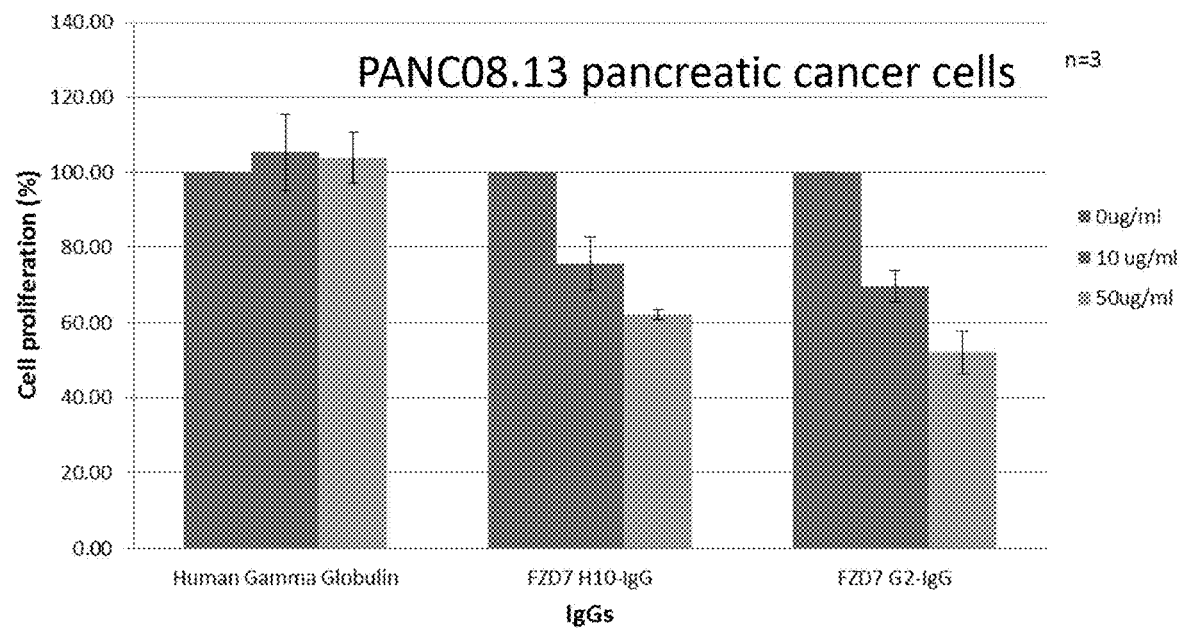
Figure 12D:
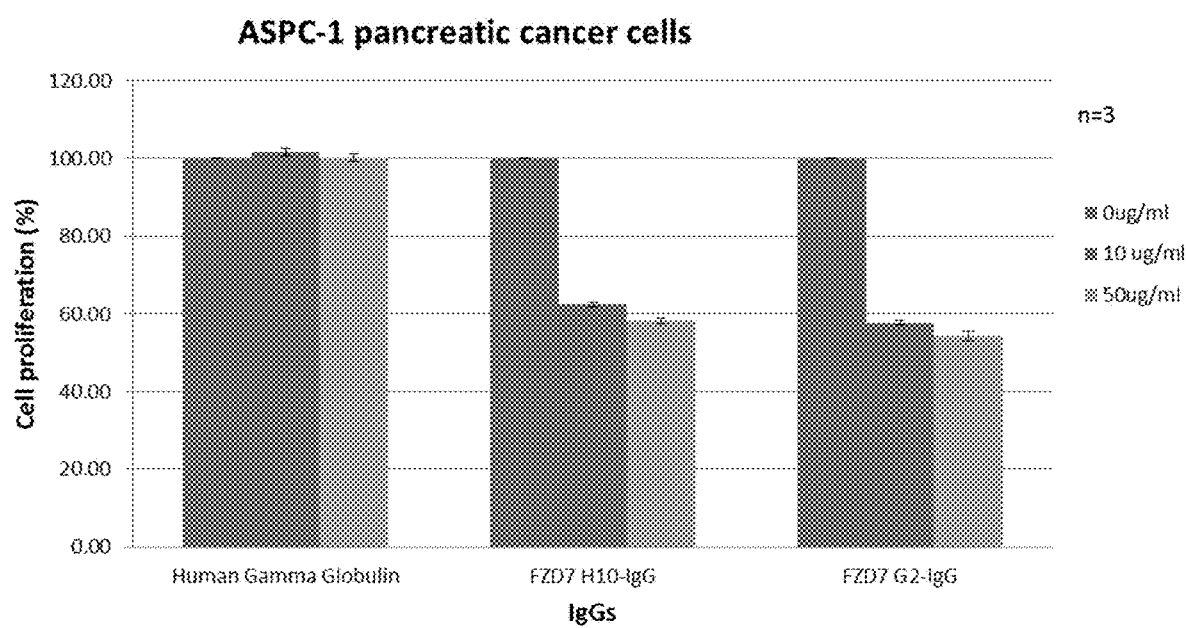
Figure 12E:
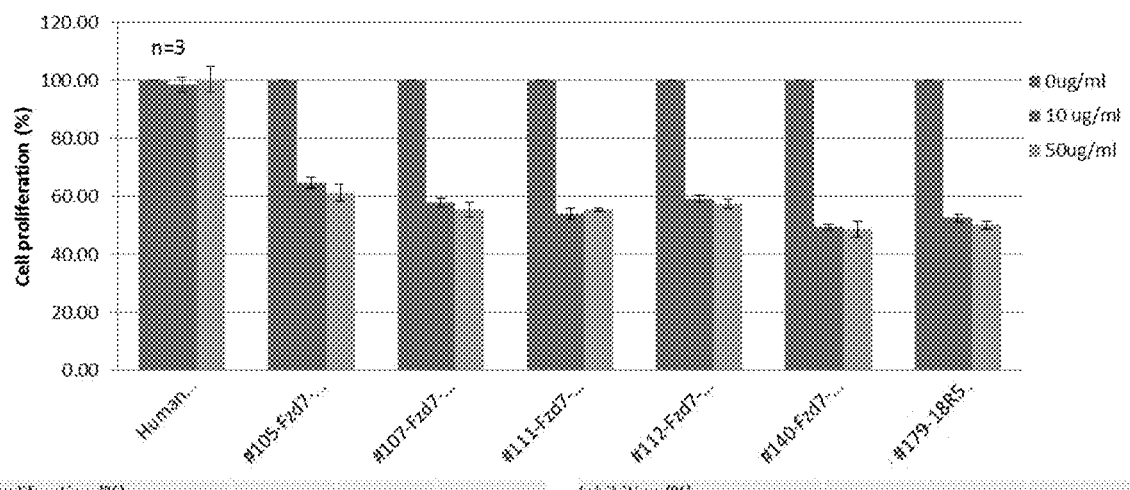

A dose dependent response in cancer cell proliferation was also shown for the cancer cell lines HPAFII, IMMPC2, PANC08.13, and ASPC1 following administration of anti-FZD7 mAbs. Following a 5 day treatment of either 10 µg/ml or 50 µg/ml of mAb H10 or G2, there was a dose dependent response in cell proliferation for the HPAFII, IMMPC2 and PANC08.13 cells. (See FIG. 12A-12D). Anti-FZD7 antibodies A1 (mAb #105), E4 (mAb #107), H10 (mAb #111), H1 (mAb #112), G2 (mAb #140), and 18R5 were also shown to have a dose dependent response in the reduction of cell proliferation of Capan-2 cells. (See FIG. 12E).

Figure 13A:
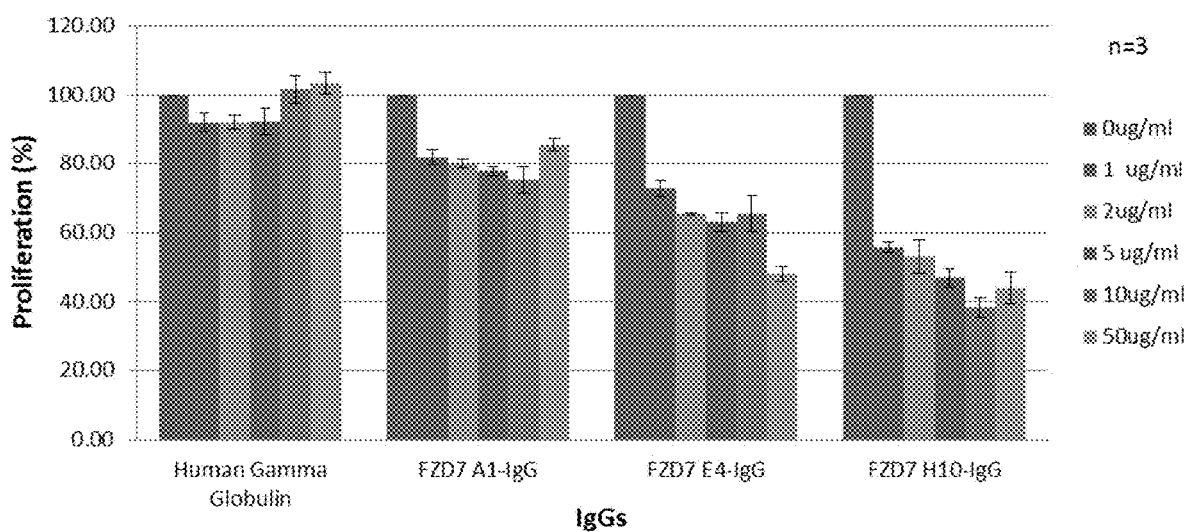
FIG. 13A-13B are a series of graphs and tables depicting a dose dependent response in the proliferation of the cancer cell line APSC-1, following 5 days of incubation with anti-FZD7 antibodies, A1 (mAb #105), E4 (mAb #107), H10 (mAb #111), H1 (mAb #112), G2 (mAb #140) or 18R5.
Figure 13B:
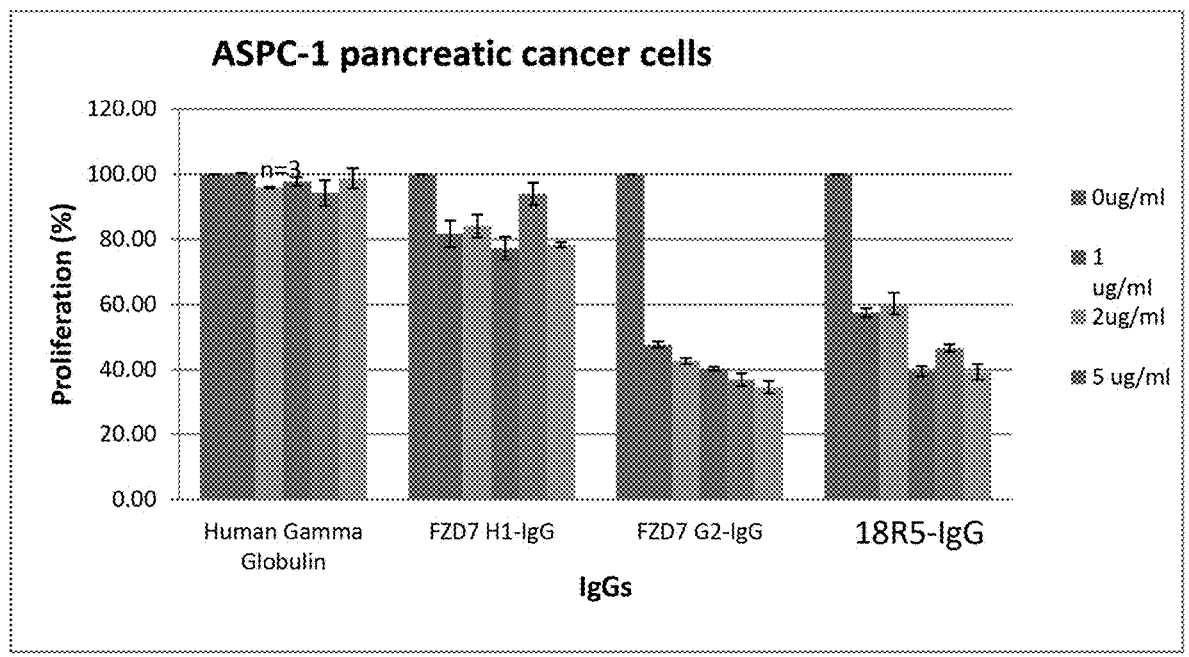

For the in vitro experiments using ASPC-1 cells the concentrations of the antibodies added to the culture medium included 1 µg/ml, 2 µg/ml, 5 µg/ml, 10 µg/ml, or 50 µg/ml. Dose-dependent inhibition of cell proliferation was shown for mAbs A1, E4, and H1. (See FIGS. 13A and 13B).

Example 4: In Vivo Assessment of Tumor Response Following Administration of Anti-FZD7 mAbs Five to six week old female C.B-17 SCID mice (Taconic Farms, Germantown, N.Y., USA) received transplants of one of three pancreatic cell lines, AsPC1, CAPAN2 or HPAFII, followed by administration of anti-FZD7 mAbs to assess response to mAb treatment. Below are detailed descriptions of the in vivo work and results.

Figure 14:
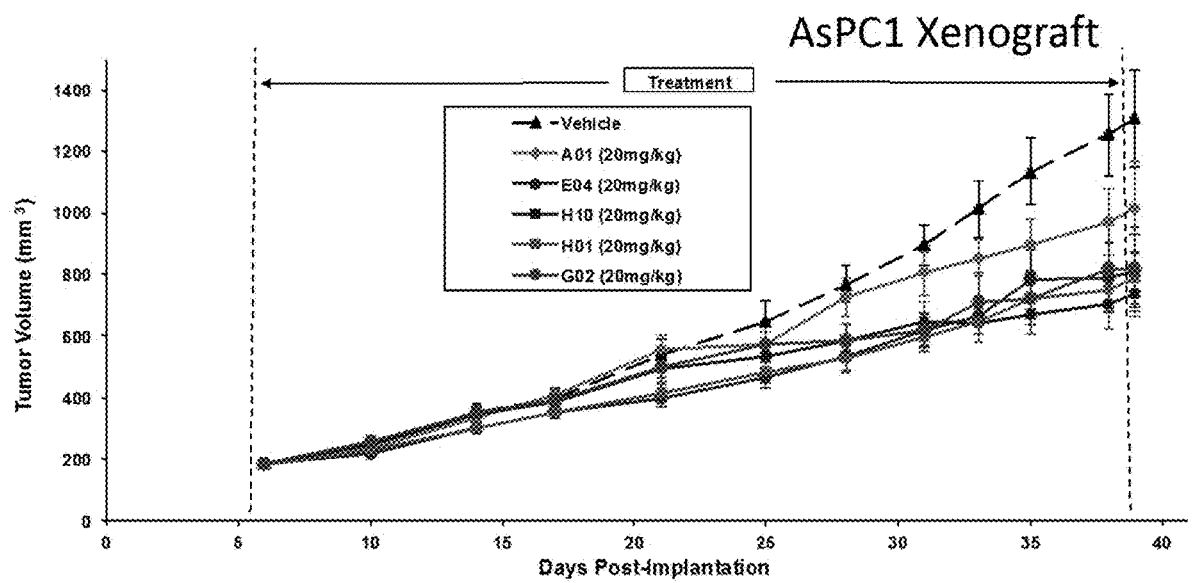
FIG. 14 is a graph and a table depicting in vivo tumor growth inhibition following administration of anti-FZD7 mAbs to a mouse xenograft tumor model. Three million AsPC1 cells were transplanted into the flank of C.B-17 SCID mice, followed by treatment with 20 mg/kg anti-FZD7 mAb starting on day 6 administered twice per week. All tested anti-FZD7 antibodies (i.e. A01 (mAb #105), E04 (mAb #107), H10 (mAb #111), H01 (mAb #112), G02 (mAb #140)) demonstrated anti-tumor activity with tumor growth inhibition (TGI) ranging from 25%-50%.

AsPC1 Transplants: C.B-17 SCID mice were injected in the right flank with 3 million AsPC1 cells in 100 µl of DPBS, followed by a 6 day rest period to allow the formation of an average tumor volume of 184.9 mm$^3$. There were a total of 6 experimental groups, with each group containing 9 mice. The anti-FZD7 antibodies, A1 (mAb #105), E4 (mAb #107), H10 (mAb #111), H01 (mAb #112), G2 (mAb #140), or a vehicle control (100 µl DPBS), were administered via IP twice per week, for a total of 5 weeks, at a concentration of 20 mg/kg. All anti-FZD7 mAbs resulted in a marked decrease in tumor volume after the 5 week dosing regimen, ranging from a 25.6% reduction (following administration of mAb A1), to a 50.8% reduction (following administration of mAb H10). (See FIG. 14).

Figure 15:
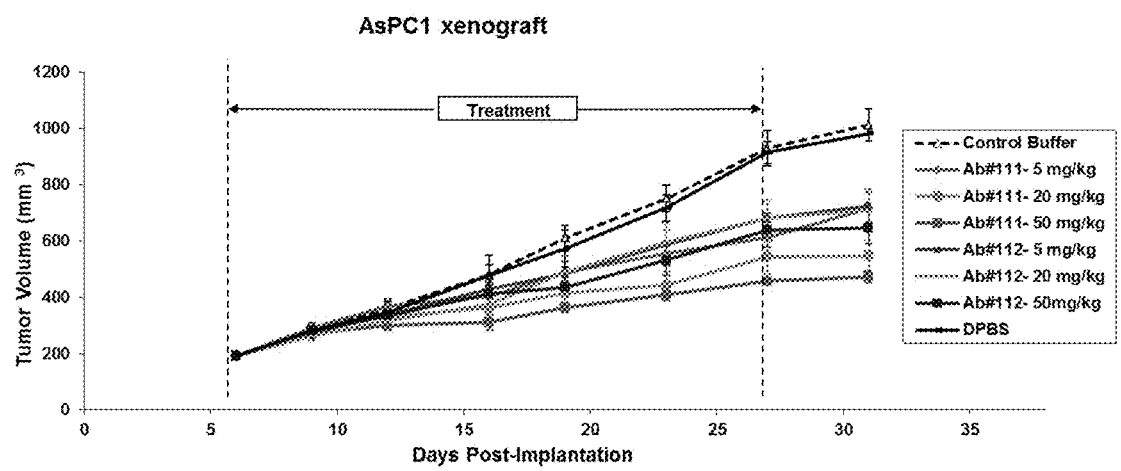
FIG. 15 is a graph and a table depicting in vivo dose-dependent tumor growth inhibition following administration of anti-FZD7 antibodies, H10 (mAb #111) and H01 (mAb #112). Three million AsPC1 cells were transplanted into the flank of C.B-17 SCID mice, followed by treatment starting on day 6 post-transplant with either H10 (mAb #111) or H01(mAb #112) at a concentration of 5 mg/kg, 20 mg/kg, or 50 mg/kg administered twice per week. Dose-dependent tumor growth inhibitory activities were observed for both H10 (mAb #111) and H01 (mAb #112), with a reduction in tumor volume ranging from 36.3-65.8% for H10 (mAb #111) and 35.4%-44.7% for mAb H01 (mAb #112), respectively.

Dose dependent responses in the AsPC1 mouse xenografts were also assessed with mAb111 (also referred to herein as H10) and mAb112 (also referred to herein as H1). Mouse xenograft recipients began treatment following 6 days of tumor growth (average volume=193.6 mm$^3$) with dosages of 5 mg/kg, 20 mg/kg, 50 mg/kg, or vehicle only (DPBS) control, twice per week for a total of 4 weeks. For these experiments there were a total of 8 groups, wherein each group contained 9 animals, except for the DPBS control group which contained 8 animals. There was a dose dependent decrease in tumor volume size following treatment, ranging from a 36.3% reduction in tumor volume with the 5 mg/kg dose, to a 65.8% reduction in tumor volume with the 50 mg/kg dose, following administration of mAb111; following treatment with mAb112, there was a reduction in tumor volume size ranging from 3 5.4% (5 mg/kg dose) to 44.7% (50 mg/kg). (See FIG. 15).

Figure 16:
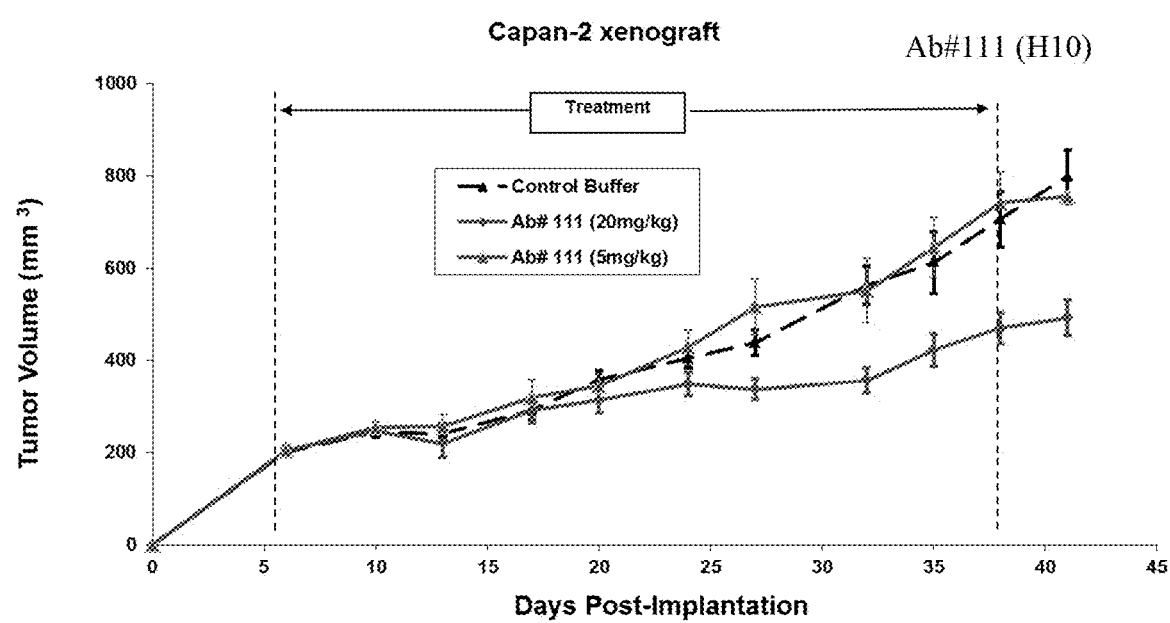
FIG. 16 is a graph depicting dose-dependent tumor growth inhibition following administration of anti-FZD7 antibody H10 (mAb #111) in a Capan-2 xenograft mouse model. Four million Capan-2 cells were transplanted into the flank of C.B-17 SCID mice, followed by treatment on day 6 post-transplant with H10 (mAb #112) at concentrations of either 5 mg/kg or 20 mg/kg administered twice per week, for a total 10 doses. Administration of 20 mg/kg resulted in the reduction of tumor volume by 52%.

CAPAN2 Transplants: C.B-17 SCID mice were injected in the right flank with 4 million AsPC1 cells, followed by a 6 day rest period to allow the formation of an average tumor volume of 203.6 mm$^3$. For these experiments, anti-FZD7 mAb, mAb111, was administered via IP in dosages of either 5 mg/kg or 20 mg/kg, or as a control, vehicle only (DPBS). The dosage regimen was administered twice per week for a total of 5 weeks. The mice were distributed randomly into 3 groups, with each group containing 10 mice. Administration of mAb111 resulted in reduction of the tumor volume by 52% following 5 weeks of treatment. (See FIG. 16).

Figure 17:
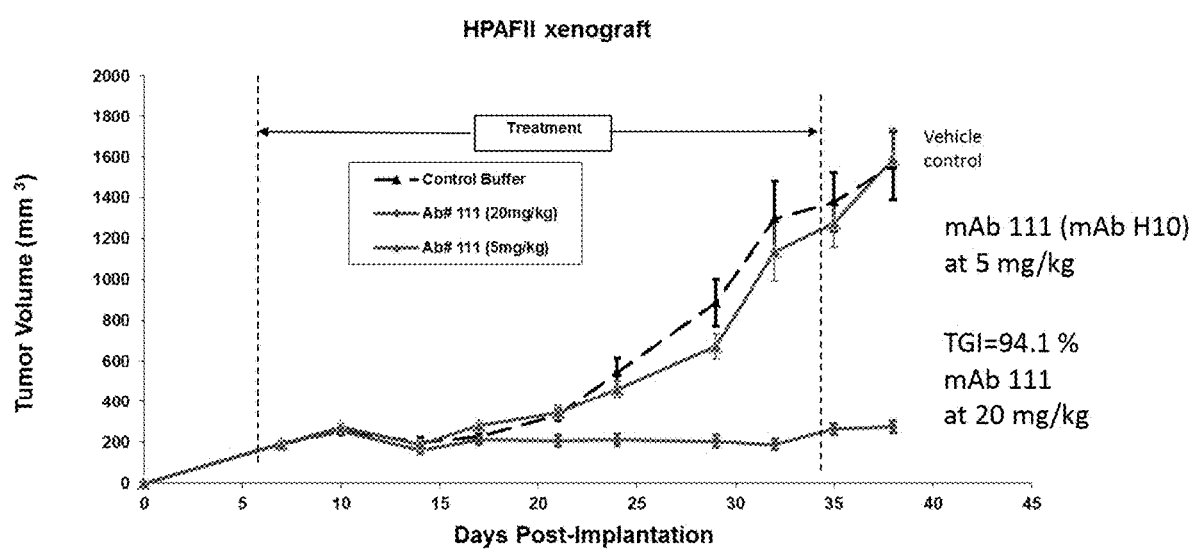
FIG. 17 is a graph depicting dose-dependent tumor growth inhibition following administration of anti-FZD7 antibody H10 (mAb #111) in a HPAFII xenograft mouse model. Three million HPAFII cells were transplanted into the flank of C.B-17 SCID mice, followed by twice weekly treatment on day 6 post-transplant with H10 (mAb #111) for 4.5 weeks at a concentration of either 5 mg/kg or 20 mg/kg administered for a total of 8 doses. Administration of 20 mg/kg resulted in the reduction of tumor volume by 94%.

HPAFII Transplants: C.B-17 SCID mice were injected in the right flank with 3 million AsPC1 cells, followed by a 7 day rest period to allow the formation of an average tumor volume of 191.5 mm$^3$. For these experiments, anti-FZD7 mAb, mAb111, was administered via IP in dosages of either 5 mg/kg or 20 mg/kg, or as a control, vehicle only (DPBS). The dosage regimen was administered twice per week for a total of 4.5 weeks. The mice were distributed randomly into 3 groups, with each group containing 10 mice. Administration of mAb111 resulted in reduction of the tumor volume by 94.1% following 5 weeks of treatment. (See FIG. 17).

What is claimed is:

1. An isolated antibody or antigen-binding fragment thereof that binds to one or more Frizzled receptors and prevents the one or more Frizzled receptors from binding to a Wnt protein ligand, wherein the antibody or antigen-binding fragment thereof comprises:
   a) a variable light chain complementarity determining region 1 (CDRL1) comprising an amino acid sequence of SEQ ID NO: 392;
   b) a variable light chain complementarity determining region 2 (CDRL2) comprising an amino acid sequence of SEQ ID NO: 393;
   c) a variable light chain complementarity determining region 3 (CDRL3) comprising an amino acid sequence of SEQ ID NO: 132;
   d) a variable heavy chain complementarity determining region (CDRH1) comprising an amino acid sequence of SEQ ID NO: 133;
   e) a variable heavy chain complementarity determining region (CDRH2) comprising an amino acid sequence of SEQ ID NO: 134; and
   f) a variable heavy chain complementarity determining region (CDRH3) comprising an amino acid sequence of SEQ ID NO: 135.

2. The antibody or antigen-binding fragment thereof of claim 1, wherein the antibody is an IgG isotype.

3. The antibody or antigen-binding fragment thereof of claim 1, wherein the antibody is an IgG1 isotype.

4. A pharmaceutical composition comprising the antibody or antigen-binding fragment thereof of claim 1 and a carrier.

5. A method of alleviating a symptom of a disease or disorder associated with aberrant Frizzled receptor expression or activity in a subject, the method comprising administering the antibody or antigen-binding fragment thereof of claim 1 to a subject in need thereof in an amount sufficient to alleviate the symptom of the disease or disorder associated with aberrant Frizzled receptor expression or activity.

6. The method of claim 5, wherein the subject is a human.

7. The method of claim 5, wherein the disease or disorder associated with aberrant Frizzled receptor expression or activity is cancer.

8. The method of claim 7, wherein the cancer is selected from breast cancer, lung cancer, colon cancer, ovarian cancer, pancreatic cancer, gastrointestinal (GI) cancer, neuroblastoma, renal cancer, prostate cancer, melanoma, leukemia or Wilm's tumor.

* * * * *

SEQUENCE LISTING

<160> NUMBER OF SEQ ID NOS: 398

<210> SEQ ID NO 1
<211> LENGTH: 660
<212> TYPE: DNA
<213> ORGANISM: Homo sapiens

<400> SEQUENCE: 1

| | | |
|---|---|---|
| gatatccaga tgacccagtc cccgagctcc ctgtccgcct ctgtgggcga tagggtcacc | 60 |
| atcacctgcc gtgccagtca gtccgtgtcc agcgctgtag cctggtatca acagaaacca | 120 |
| ggaaaagctc cgaagcttct gatttactcg gcatccagcc tctactctgg agtcccttct | 180 |
| cgcttctctg gtagccgttc cgggacggat ttcactctga ccatcagcag tctgcagccg | 240 |
| gaagacttcg caacttatta ctgtcagcaa gctgcttacc attggccgcc gctgttcacg | 300 |
| ttcggacagg gtaccaaggt ggagatcaaa cgaactgtgg ctgcaccatc tgtcttcatc | 360 |
| ttcccgccat ctgattcaca gttgaaatct ggaactgcct ctgttgtgtg cctgctgaat | 420 |
| aacttctatc ccagagaggc caaagtacag tggaaggtgg ataacgccct ccaatcgggt | 480 |
| aactcccagg agagtgtcac agagcaggac agcaaggaca gcacctacag cctcagcagc | 540 |
| accctgacgc tgagcaaagc agactacgaa aacataaag tctacgcctg cgaagtcacc | 600 |
| catcagggcc tgagctcgcc cgtcacaaag agcttcaaca ggggagagtg tggtggttct | 660 |

<210> SEQ ID NO 2
<211> LENGTH: 220
<212> TYPE: PRT
<213> ORGANISM: Homo sapiens

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ala Tyr His Trp Pro
                85                  90                  95

Pro Leu Phe Thr Phe Gly Gln Gly Thr Lys Val Glu Ile Lys Arg Thr
            100                 105                 110

Val Ala Ala Pro Ser Val Phe Ile Phe Pro Pro Ser Asp Ser Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

```
Thr Lys Ser Phe Asn Arg Gly Glu Cys Gly Gly Ser
    210                 215                 220
```

<210> SEQ ID NO 3
<211> LENGTH: 654
<212> TYPE: DNA
<213> ORGANISM: Homo sapiens

<400> SEQUENCE: 3

```
gaggttcagc tggtggagtc tggcggtggc ctggtgcagc caggggggctc actccgtttg      60 tcctgtgcag cttctggctt caacctctat tattcttcta tgcactgggt gcgtcaggcc     120
ccgggtaagg gcctggaatg ggttgcatat atttctcctt attctggcta tacttcttat     180
gccgatagcg tcaagggccg tttcactata agcgcagaca catccaaaaa cacagcctac     240
ctacaaatga acagcttaag agctgaggac actgccgtct attattgtgc tcgctactgg     300
gctatggact actggggtca aggaaccctg gtcaccgtct cctcggcctc caccaagggt     360
ccatcggtct tccccctggc accctcctcc aagagcacct ctggggggcac agcggccctg     420 ggctgcctgg tcaaggacta cttccccgaa ccggtgacgg tgtcgtggaa ctcaggcgcc     480
ctgaccagcg gcgtgcacac cttcccggct gtcctacagt cctcaggact ctactccctc     540
agcagcgtgg tgaccgtgcc ctccagcagc ttgggcaccc agacctacat ctgcaacgtg     600
aatcacaagc ccagcaacac caaggtcgac aagaaagttg agcccaaatc ttgt           654
```

<210> SEQ ID NO 4
<211> LENGTH: 215
<212> TYPE: PRT
<213> ORGANISM: Homo sapiens

<400> SEQUENCE: 4

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Tyr Tyr Ser
            20                  25                  30

Ser Asn Arg Arg Asn Trp Val Arg Gln Ala Pro Gly Lys Gly Leu Glu
        35                  40                  45

Val Val Ala Tyr Ile Ser Pro Tyr Ser Gly Tyr Thr Ser Tyr Ala
    50                  55                  60

Asp Ser Val Lys Gly Arg Phe Thr Ile Ser Ala Asp Thr Ser Lys Asn
65                  70                  75                  80

Thr Ala Tyr Leu Gln Met Asn Ser Leu Arg Ala Glu Asp Thr Ala Val
                85                  90                  95

Tyr Tyr Cys Ala Arg Tyr Trp Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Val Val
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Cys Ser Asn Thr Lys Val Asp Lys
        195                 200                 205
```

Lys Val Glu Pro Lys Ser Cys
    210                 215

<210> SEQ ID NO 5
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 5

Tyr Gly Trp Phe Ala Tyr Tyr Pro Ile
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 6

Leu Ser Ser Ser Ser Ile
1               5

<210> SEQ ID NO 7
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 7

Tyr Ile Tyr Ser Ser Ser Gly Tyr Thr Ser
1               5                   10

<210> SEQ ID NO 8
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 8

Thr Val Arg Gly Ser Lys Lys Pro Tyr Phe Ser Gly Trp Ala Met
1               5                   10                  15

<210> SEQ ID NO 9
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 9

Ala Ser Trp Tyr Pro Ile
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 10

Ile Tyr Ser Ser Ser Met
1               5

<210> SEQ ID NO 11
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 11

Ser Ile Tyr Ser Ser Tyr Gly Tyr Thr Ser
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 12

Pro Gly Tyr Trp Gly Tyr Tyr Trp Gly Ala Tyr Gly Met
1               5                   10

<210> SEQ ID NO 13
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 13

Ala Tyr Tyr Pro Leu Phe
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 14

Ile Ser Tyr Ser Ser Met
1               5

<210> SEQ ID NO 15
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 15

Ser Ile Tyr Pro Ser Tyr Gly Tyr Thr Ser
1               5                   10

<210> SEQ ID NO 16
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 16

Val Tyr Trp Ser Ser Ser Tyr Trp Ala Gly Gly Tyr Trp Val Gly Ser

```
1               5                   10                  15
Ala Phe

<210> SEQ ID NO 17
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 17

Ala Tyr Ala Pro Phe
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 18

Ile Ser Tyr Ser Tyr Met
1               5

<210> SEQ ID NO 19
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 19

Ser Ile Tyr Ser Ser Tyr Ser Tyr Thr Ser
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 20

Ser Ser Ala Trp Phe Gly His Ala Gly Phe Gly Gly Ala Met
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 21

Tyr Phe Pro Ser Gly Leu Ile
1               5

<210> SEQ ID NO 22
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 22
```

Ser Ile Ser Pro Ser Ser Gly Tyr Thr Ser
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 23

Ser Val Ser Trp Trp Tyr Ser Trp Trp Ser Trp Gly Met
1               5                   10

<210> SEQ ID NO 24
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 24

Tyr Trp Ala Pro Ile
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 25

Ile Tyr Tyr Tyr Tyr Met
1               5

<210> SEQ ID NO 26
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 26

Ser Ile Tyr Ser Tyr Ser Gly Ser Thr Tyr
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 27

Tyr Ala Ser Tyr Val Gly Tyr Tyr Pro Trp Ala Leu
1               5                   10

<210> SEQ ID NO 28
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 28

Gly Gly His Tyr Trp Leu Ile

```
1               5

<210> SEQ ID NO 29
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 29

Ser Ile Ser Ser Ser Tyr Gly Tyr Thr Ser
1               5                   10

<210> SEQ ID NO 30
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 30

Ser Tyr Tyr Gly Tyr Tyr Val Gly Tyr Gly Tyr Ser Ser Trp Ser Gly
1               5                   10                  15

Ser Gly Met

<210> SEQ ID NO 31
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 31

Gly Ser Ala Ser Ser Ala Leu Ile
1               5

<210> SEQ ID NO 32
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 32

Phe Tyr Ser Ser Phe Tyr Phe Phe Trp Tyr Pro Pro Ala Gly Leu
1               5                   10                  15

<210> SEQ ID NO 33
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 33

Ala Val Tyr His Ala Leu Ile
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 34
```

```
Ile Tyr Tyr Ser Ser Met
1               5

<210> SEQ ID NO 35
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 35

Ser Ile Ser Ser Tyr Ser Ser Ser Thr Tyr
1               5                   10

<210> SEQ ID NO 36
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 36

Ser Ala Val Val His Tyr Pro Ala Gly Tyr Trp Val Tyr Trp Gly Trp
1               5                   10                  15

Tyr Ala Phe

<210> SEQ ID NO 37
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 37

Ala Tyr Trp Trp Val Gly Pro Ile
1               5

<210> SEQ ID NO 38
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 38

Leu Ser Tyr Ser Ser Ile
1               5

<210> SEQ ID NO 39
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 39

Tyr Ile Ser Ser Ser Tyr Gly Tyr Thr Ser
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 40
```

```
Phe Ser Ala Tyr Trp Ala Trp His Gly Leu
1               5                   10

<210> SEQ ID NO 41
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 41

Tyr Trp Ala Ser Leu Ile
1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 42

Ile Ser Tyr Tyr Tyr Ile
1               5

<210> SEQ ID NO 43
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 43

Tyr Ile Ser Pro Tyr Tyr Gly Ser Thr Tyr
1               5                   10

<210> SEQ ID NO 44
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 44

Ser Trp Ser Tyr Ser Tyr Tyr Tyr Ser His Pro Gly Trp Ser Pro Val
1               5                   10                  15

Trp Ala Met

<210> SEQ ID NO 45
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 45

Val Ser Gly Gly Gly Gly Leu Ile
1               5

<210> SEQ ID NO 46
<211> LENGTH: 6
<212> TYPE: PRT
<213> ORGANISM: Artificial Sequence
<220> FEATURE:
<223> OTHER INFORMATION: Synthetic Polypeptide
```

```
<400> SEQUENCE: 46

Ile Tyr Ser Ser Tyr Ile
1               5

<210> SEQ ID NO 47
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 47

Tyr Ile Tyr Ser Tyr Ser Gly Tyr Thr Tyr
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 48

Trp Tyr His Pro Tyr Trp Tyr Ala Ser Ala Ile
1               5                   10

<210> SEQ ID NO 49
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 49

Tyr Gly Tyr Trp Trp Val Ser Leu Phe
1               5

<210> SEQ ID NO 50
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 50

Leu Tyr Tyr Tyr Ser Ile
1               5

<210> SEQ ID NO 51
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 51

Ser Ile Tyr Ser Tyr Ser Ser Tyr Thr Tyr
1               5                   10

<210> SEQ ID NO 52
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 52
```

```
Trp Trp Pro Gly His Tyr Ser Gly Tyr Gly Ser Gly Ala Leu
1               5                   10
```

<210> SEQ ID NO 53
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 53

```
Trp Ala Tyr Gly Pro Phe
1               5
```

<210> SEQ ID NO 54
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 54

```
Ile Tyr Tyr Tyr Ser Met
1               5
```

<210> SEQ ID NO 55
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 55

```
Ser Ser Pro Gly Ala Asp Tyr Gly Leu
1               5
```

<210> SEQ ID NO 56
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 56

```
Ser Ser Gly Pro Trp Tyr Tyr Pro Ile
1               5
```

<210> SEQ ID NO 57
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 57

```
Phe Ser Ser Ser Ser Ile
1               5
```

<210> SEQ ID NO 58
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 58

Ser Ile Ser Ser Ser Tyr Gly Tyr Thr Tyr
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 59

Trp Trp Ser Gly Gly Trp Tyr Tyr Ser Tyr Gly Met
1               5                   10

<210> SEQ ID NO 60
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 60

Ser Tyr Val Tyr Tyr Leu Ile
1               5

<210> SEQ ID NO 61
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 61

Ile Ser Tyr Tyr Ser Met
1               5

<210> SEQ ID NO 62
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 62

Tyr Ile Tyr Pro Tyr Ser Ser Tyr Thr Tyr
1               5                   10

<210> SEQ ID NO 63
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 63

Tyr His Gly Phe Tyr Gly Met
1               5

<210> SEQ ID NO 64
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 64

Ser Tyr Trp Pro Gly Trp Pro Ile

```
1               5

<210> SEQ ID NO 65
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 65

Tyr Ile Tyr Pro Tyr Tyr Gly Tyr Thr Tyr
1               5                   10

<210> SEQ ID NO 66
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 66

Trp Val Val Ala Gly His Tyr Gly Met
1               5

<210> SEQ ID NO 67
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 67

Ser Ala Trp Trp Ala Ser Leu Phe
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 68

Ile Ser Ser Tyr Ser Ile
1               5

<210> SEQ ID NO 69
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 69

Ser Ile Tyr Pro Tyr Ser Ser Tyr Thr Tyr
1               5                   10

<210> SEQ ID NO 70
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 70

Tyr Ser Gly Phe Ala Met
1               5
```

<210> SEQ ID NO 71
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 71

Ser Ser Tyr Ser Leu Ile
1               5

<210> SEQ ID NO 72
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 72

Leu Ser Tyr Ser Tyr Met
1               5

<210> SEQ ID NO 73
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 73

Tyr Tyr Gly Trp Ala Tyr Tyr Ser Tyr Phe Pro Ala Trp Ala Gly
1               5                   10                  15

Gly Gly Ile

<210> SEQ ID NO 74
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 74

Tyr Ser Tyr Gly Tyr Ala Leu Phe
1               5

<210> SEQ ID NO 75
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 75

Leu Ser Ser Tyr Tyr Met
1               5

<210> SEQ ID NO 76
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 76

Ser Ile Tyr Pro Tyr Tyr Ser Tyr Thr Tyr

<210> SEQ ID NO 77
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 77

Tyr Trp Ser Gly Phe
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 78

Trp Trp Ala Ser Gly Val Gly Pro Phe
1               5

<210> SEQ ID NO 79
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 79

Leu Tyr Ser Ser Ser Ile
1               5

<210> SEQ ID NO 80
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 80

Tyr Ile Ser Ser Tyr Tyr Ser Ser Thr Tyr
1               5                   10

<210> SEQ ID NO 81
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 81

Pro Ala Met
1

<210> SEQ ID NO 82
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 82

Trp Tyr Tyr Gly Trp His Leu Ile
1               5

```
<210> SEQ ID NO 83
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 83

Ile Ser Tyr Ser Ser Ile
1               5

<210> SEQ ID NO 84
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 84

Ser Ile Tyr Pro Ser Tyr Gly Tyr Thr Tyr
1               5                   10

<210> SEQ ID NO 85
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 85

Tyr Gly Tyr Phe Gly Met
1               5

<210> SEQ ID NO 86
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 86

Tyr Val Tyr Ser Ser Leu Ile
1               5

<210> SEQ ID NO 87
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 87

Ser Ile Tyr Pro Ser Tyr Gly Ser Thr Tyr
1               5                   10

<210> SEQ ID NO 88
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 88

Pro Gly Val Gly Gly Tyr Tyr Ala Met
1               5
```

<210> SEQ ID NO 89
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 89

Ser Tyr Ser Ala Ser Leu Phe
1               5

<210> SEQ ID NO 90
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 90

Leu Tyr Tyr Ser Tyr Ile
1               5

<210> SEQ ID NO 91
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 91

Ser Ile Ser Pro Ser Tyr Ser Ser Thr Tyr
1               5                   10

<210> SEQ ID NO 92
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 92

Val Ser Tyr Trp Gly Ala Gly Met
1               5

<210> SEQ ID NO 93
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 93

Leu Ser Tyr Tyr Ser Met
1               5

<210> SEQ ID NO 94
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 94

Pro Ser Pro Gly Ser Tyr His Gly Met
1               5

<210> SEQ ID NO 95
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 95

Trp Gly Ser Tyr Val Ala Leu Phe
1               5

<210> SEQ ID NO 96
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 96

Ile Tyr Ser Tyr Ser Ile
1               5

<210> SEQ ID NO 97
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 97

Ser Ile Tyr Ser Tyr Tyr Gly Ser Thr Tyr
1               5                   10

<210> SEQ ID NO 98
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 98

Val Gly Pro Gly Ser Tyr Gly Gly Leu
1               5

<210> SEQ ID NO 99
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 99

Phe Trp Gly Leu Phe
1               5

<210> SEQ ID NO 100
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 100

Ser Ile Tyr Pro Ser Tyr Ser Ser Thr Tyr
1               5                   10

<210> SEQ ID NO 101

```
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 101

Pro Ser Pro Gly Gly Tyr Ser Ala Leu
1               5

<210> SEQ ID NO 102
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 102

Tyr Tyr Ser Tyr Ser Val Trp Leu Ile
1               5

<210> SEQ ID NO 103
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 103

Ile Ser Tyr Tyr Tyr Met
1               5

<210> SEQ ID NO 104
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 104

Tyr Ile Ser Pro Ser Ser Ser Tyr Thr Ser
1               5                   10

<210> SEQ ID NO 105
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 105

Trp Tyr Gly Trp Ala Leu
1               5

<210> SEQ ID NO 106
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 106

Pro Ala Tyr Ser Ala Pro Ile
1               5

<210> SEQ ID NO 107
<211> LENGTH: 10
```

```
<212> TYPE: PRT
<213> ORGANISM: Artificial Sequence
<220> FEATURE:
<223> OTHER INFORMATION: Synthetic Polypeptide

<400> SEQUENCE: 107

Ser Ile Tyr Ser Ser Tyr Gly Ser Thr Tyr
1               5                   10

<210> SEQ ID NO 108
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 108

Val Gly Pro Gly Gly Phe Gly Ala Leu
1               5

<210> SEQ ID NO 109
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 109

Ser Tyr Tyr Pro Ile
1               5

<210> SEQ ID NO 110
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 110

Leu Ser Tyr Tyr Tyr Ile
1               5

<210> SEQ ID NO 111
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 111

Phe Ser Gly Trp Ala Leu
1               5

<210> SEQ ID NO 112
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 112

Gly Val Tyr Leu Phe
1               5

<210> SEQ ID NO 113
<211> LENGTH: 6
<212> TYPE: PRT
```

```
<213> ORGANISM: Artificial Sequence
<220> FEATURE:
<223> OTHER INFORMATION: Synthetic Polypeptide

<400> SEQUENCE: 113

Ile Tyr Ser Ser Ser Ile
1               5

<210> SEQ ID NO 114
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 114

Ser Ile Tyr Ser Ser Tyr Gly Ser Thr Ser
1               5                   10

<210> SEQ ID NO 115
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 115

Tyr His Tyr Pro Phe Gly His Ala Leu
1               5

<210> SEQ ID NO 116
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 116

Trp Gly Tyr Gly Ala Leu Ile
1               5

<210> SEQ ID NO 117
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 117

Ser Ile Tyr Pro Ser Pro Gly Tyr Thr Ser
1               5                   10

<210> SEQ ID NO 118
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 118

His Gly Trp Tyr Gly Leu
1               5

<210> SEQ ID NO 119
<211> LENGTH: 6
<212> TYPE: PRT
<213> ORGANISM: Artificial Sequence
```

<220> FEATURE:
<223> OTHER INFORMATION: Synthetic Polypeptide

<400> SEQUENCE: 119

Leu Ser Tyr Ser Ser Met
1               5

<210> SEQ ID NO 120
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 120

Ser Ile Tyr Ser Ser Tyr Ser Ser Thr Ser
1               5                   10

<210> SEQ ID NO 121
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 121

Gly Ala Gly Tyr Tyr Trp Trp His Tyr Tyr Val His Gly Ala Met
1               5                   10                  15

<210> SEQ ID NO 122
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 122

Tyr Tyr Ser Leu Phe
1               5

<210> SEQ ID NO 123
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 123

Tyr Ile Ser Pro Ser Tyr Gly Tyr Thr Tyr
1               5                   10

<210> SEQ ID NO 124
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 124

Gly Tyr Phe Tyr Ser Trp Gly Gly Met
1               5

<210> SEQ ID NO 125
<211> LENGTH: 7
<212> TYPE: PRT
<213> ORGANISM: Artificial Sequence
<220> FEATURE:

<223> OTHER INFORMATION: Synthetic Polypeptide

<400> SEQUENCE: 125

Tyr Tyr Tyr Ser Ser Pro Ile
1               5

<210> SEQ ID NO 126
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 126

Tyr Ile Ser Pro Ser Ser Gly Tyr Thr Ser
1               5                   10

<210> SEQ ID NO 127
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 127

Gly Tyr Pro Val Tyr Ser Trp Val Trp Ser Phe Gly Ala Phe
1               5                   10

<210> SEQ ID NO 128
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 128

Ala Ala Tyr His Trp Pro Pro Leu Phe
1               5

<210> SEQ ID NO 129
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 129

Leu Tyr Tyr Ser Ser Met
1               5

<210> SEQ ID NO 130
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 130

Tyr Ile Ser Pro Tyr Ser Gly Tyr Thr Ser
1               5                   10

<210> SEQ ID NO 131
<211> LENGTH: 4
<212> TYPE: PRT
<213> ORGANISM: Artificial Sequence
<220> FEATURE:
<223> OTHER INFORMATION: Synthetic Polypeptide

```
<400> SEQUENCE: 131

Tyr Trp Ala Met
1

<210> SEQ ID NO 132
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 132

Tyr Trp Tyr Gly Val Ala Pro Ile
1               5

<210> SEQ ID NO 133
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 133

Ile Ser Ser Ser Tyr Ile
1               5

<210> SEQ ID NO 134
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 134

Tyr Ile Tyr Ser Ser Tyr Gly Ser Thr Tyr
1               5                   10

<210> SEQ ID NO 135
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 135

Ala Ser Trp Tyr Ala Leu
1               5

<210> SEQ ID NO 136
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 136

Ala Tyr Tyr Leu Ile
1               5

<210> SEQ ID NO 137
<211> LENGTH: 6
<212> TYPE: PRT
<213> ORGANISM: Artificial Sequence
<220> FEATURE:
<223> OTHER INFORMATION: Synthetic Polypeptide
```

```
<400> SEQUENCE: 137

Ile Tyr Tyr Ser Ser Ile
1               5

<210> SEQ ID NO 138
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 138

Ser Ile Tyr Pro Ser Ser Gly Tyr Thr Tyr
1               5                   10

<210> SEQ ID NO 139
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 139

Trp Ala Pro His Ser Ser Ser Trp Trp Ser Val Tyr Gly Trp Ser Ala
1               5                   10                  15

Trp Ala Phe

<210> SEQ ID NO 140
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 140

Tyr Phe Tyr Ser Ser Tyr Ser Pro Ile
1               5

<210> SEQ ID NO 141
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 141

Tyr Ile Tyr Pro Ser Tyr Ser Ser Thr Ser
1               5                   10

<210> SEQ ID NO 142
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 142

Ala Ser Tyr Trp Ala Leu
1               5

<210> SEQ ID NO 143
<211> LENGTH: 7
<212> TYPE: PRT
<213> ORGANISM: Artificial Sequence
<220> FEATURE:
<223> OTHER INFORMATION: Synthetic Polypeptide
```

```
<400> SEQUENCE: 143

Ser Val His Trp Tyr Pro Phe
1               5

<210> SEQ ID NO 144
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 144

Ile Ser Tyr Tyr Ser Ile
1               5

<210> SEQ ID NO 145
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 145

Tyr Ile Tyr Pro Tyr Ser Gly Ser Thr Tyr
1               5                   10

<210> SEQ ID NO 146
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 146

Trp Ala His Tyr Gly Tyr Tyr Gly Phe Ser Tyr Ser Val Tyr Ser Gly
1               5                   10                  15

Gly Met

<210> SEQ ID NO 147
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 147

Tyr His Tyr Gly Tyr Tyr Pro Phe
1               5

<210> SEQ ID NO 148
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 148

Leu Ser Ser Ser Tyr Ile
1               5

<210> SEQ ID NO 149
<211> LENGTH: 6
<212> TYPE: PRT
<213> ORGANISM: Artificial Sequence
<220> FEATURE:
```

```
<223> OTHER INFORMATION: Synthetic Polypeptide

<400> SEQUENCE: 149

Ala Ser Trp Trp Ala Ile
1               5

<210> SEQ ID NO 150
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 150

Ile Ser Ser Tyr Tyr Ile
1               5

<210> SEQ ID NO 151
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 151

Pro Trp Ser His Tyr Ser Ser Gly Ala Tyr Trp His Pro Trp Ser Gly
1               5                   10                  15

His Ala Leu

<210> SEQ ID NO 152
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 152

Ser Phe Tyr Trp Gly Tyr Pro Pro Phe
1               5

<210> SEQ ID NO 153
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 153

Ser Ile Tyr Ser Tyr Tyr Gly Tyr Thr Tyr
1               5                   10

<210> SEQ ID NO 154
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 154

Trp Tyr Ala Phe
1

<210> SEQ ID NO 155
<211> LENGTH: 8
<212> TYPE: PRT
<213> ORGANISM: Artificial Sequence
```

```
<220> FEATURE:
<223> OTHER INFORMATION: Synthetic Polypeptide

<400> SEQUENCE: 155

Tyr Ser Pro Ser Ser Phe Leu Ile
1               5

<210> SEQ ID NO 156
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 156

Ile Tyr Tyr Ser Tyr Ile
1               5

<210> SEQ ID NO 157
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 157

Ser Ile Ser Ser Ser Ser Gly Tyr Thr Ser
1               5                   10

<210> SEQ ID NO 158
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 158

Ser Tyr Gly Tyr Tyr Tyr Phe Tyr Tyr Tyr Gly Gly Met
1               5                   10

<210> SEQ ID NO 159
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 159

Tyr Tyr His Pro Ile
1               5

<210> SEQ ID NO 160
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 160

Ser Ile Tyr Pro Tyr Tyr Ser Ser Thr Tyr
1               5                   10

<210> SEQ ID NO 161
<211> LENGTH: 6
<212> TYPE: PRT
<213> ORGANISM: Artificial Sequence
<220> FEATURE:
```

<223> OTHER INFORMATION: Synthetic Polypeptide

<400> SEQUENCE: 161

Val Trp Tyr Gly Ala Met
1               5

<210> SEQ ID NO 162
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 162

Gly His Tyr Tyr Pro Tyr Tyr Leu Phe
1               5

<210> SEQ ID NO 163
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 163

Ile Tyr Tyr Ser Tyr Met
1               5

<210> SEQ ID NO 164
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 164

Ser Ile Tyr Ser Tyr Ser Gly Tyr Thr Tyr
1               5                   10

<210> SEQ ID NO 165
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 165

Ser Val Trp Gly Tyr Pro Tyr Gly Met
1               5

<210> SEQ ID NO 166
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 166

Ser Ile Tyr Pro Tyr Ser Gly Tyr Thr Tyr
1               5                   10

<210> SEQ ID NO 167
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 167

Trp His Gly Tyr Gly Ile
1               5

<210> SEQ ID NO 168
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 168

Ser Tyr Ser Gly Trp Gly Pro Phe
1               5

<210> SEQ ID NO 169
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 169

Ser Ile Ser Ser Ser Ser Ser Tyr Thr Tyr
1               5                   10

<210> SEQ ID NO 170
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 170

Ser Ala Tyr Pro Phe Ser Trp Ser Tyr Pro Ser Tyr Val Gly Tyr Tyr
1               5                   10                  15

Ser Gly Leu

<210> SEQ ID NO 171
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 171

Gly Pro Ala Tyr Ser Tyr Leu Phe
1               5

<210> SEQ ID NO 172
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 172

Gly Tyr Tyr Gly Leu
1               5

<210> SEQ ID NO 173
<211> LENGTH: 6
<212> TYPE: PRT
<213> ORGANISM: Artificial Sequence
<220> FEATURE:

```
<223> OTHER INFORMATION: Synthetic Polypeptide

<400> SEQUENCE: 173

Phe Tyr Tyr Ser Leu Ile
1               5

<210> SEQ ID NO 174
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 174

Ser Tyr Gly Pro Trp Ala Pro Gly Trp Ala Ala Tyr Trp Gly Gly Tyr
1               5                   10                  15

Gly Met

<210> SEQ ID NO 175
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 175

Ala Tyr Ala Tyr Leu Ile
1               5

<210> SEQ ID NO 176
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 176

Ser Gly Gly His Phe Tyr Tyr Trp Tyr Val Ala Ala Ala Met
1               5                   10

<210> SEQ ID NO 177
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 177

Tyr Ser Gly Pro Ile
1               5

<210> SEQ ID NO 178
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 178

Tyr Ile Tyr Pro Tyr Tyr Ser Tyr Thr Tyr
1               5                   10

<210> SEQ ID NO 179
<211> LENGTH: 19
<212> TYPE: PRT
<213> ORGANISM: Artificial Sequence
```

<220> FEATURE:
<223> OTHER INFORMATION: Synthetic Polypeptide

<400> SEQUENCE: 179

Ser Val Thr Tyr His Ser Ser Gly Trp Val Pro Pro Tyr Trp Gly
1               5                   10                  15
Tyr Ala Phe

<210> SEQ ID NO 180
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 180

Tyr Ser Ser Pro Ile
1               5

<210> SEQ ID NO 181
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 181

Tyr Ile Ser Pro Tyr Tyr Ser Tyr Thr Tyr
1               5                   10

<210> SEQ ID NO 182
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 182

Ser Val Trp Val Tyr Trp Gly Ser Trp Tyr Ser Tyr Ser His Ala Ser
1               5                   10                  15
Gly Leu

<210> SEQ ID NO 183
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 183

Ala Phe Gly Trp Pro Leu Ile
1               5

<210> SEQ ID NO 184
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 184

Tyr Ile Tyr Pro Tyr Ser Gly Ser Thr Ser
1               5                   10

<210> SEQ ID NO 185

```
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 185

Ala Gly Trp Tyr Val Tyr Gly Pro Tyr Gly Phe
1               5                   10

<210> SEQ ID NO 186
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 186

Gly Ser Val Trp Leu Phe
1               5

<210> SEQ ID NO 187
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 187

Ile Ser Ser Ser Ser Met
1               5

<210> SEQ ID NO 188
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 188

Tyr Gly Ser His Trp Ser Pro Ser Tyr Ser Gly Trp Tyr Tyr Tyr Ser
1               5                   10                  15

Tyr Ala Leu

<210> SEQ ID NO 189
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 189

Ala Ala Gly Pro Tyr Trp Tyr Ser Tyr Trp Tyr Ser Ala Met
1               5                   10

<210> SEQ ID NO 190
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 190

Tyr Gly His Tyr Leu Ile
1               5
```

```
<210> SEQ ID NO 191
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 191

Leu Tyr Ser Tyr Ser Met
1               5

<210> SEQ ID NO 192
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 192

Ser Ile Ser Ser Tyr Tyr Gly Ser Thr Tyr
1               5                   10

<210> SEQ ID NO 193
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 193

Ala His Gly Ser Ser Pro Gly Trp Tyr Tyr Ala Pro Tyr Ala Gly Gly
1               5                   10                  15

Gly Leu

<210> SEQ ID NO 194
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 194

Ser Tyr Val Gly Gly Pro Phe
1               5

<210> SEQ ID NO 195
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 195

Ser Ile Ser Ser Ser Tyr Ser Ser Thr Tyr
1               5                   10

<210> SEQ ID NO 196
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 196

Gly Tyr Trp Tyr Val Tyr Val Gly Trp Gly Ala Tyr Tyr Gly Pro Val
1               5                   10                  15
```

Gly Met

<210> SEQ ID NO 197
<211> LENGTH: 27
<212> TYPE: DNA
<213> ORGANISM: Artificial Sequence
<220> FEATURE:
<223> OTHER INFORMATION: Synthetic Polypeptide

<400> SEQUENCE: 197
tacggttggt tcgcttacta cccgatc                                27

<210> SEQ ID NO 198
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 198
ctctcttctt cttctatc                                          18

<210> SEQ ID NO 199
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 199
tatatttatt cttcttctgg ctatacttct                             30

<210> SEQ ID NO 200
<211> LENGTH: 45
<212> TYPE: DNA
<213> ORGANISM: Artificial Sequence
<220> FEATURE:
<223> OTHER INFORMATION: Synthetic Oligonucleotide

<400> SEQUENCE: 200
actgttcgtg gatccaaaaa accgtacttc tctggttggg ctatg            45

<210> SEQ ID NO 201
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 201
gcttactacc cgctgttc                                          18

<210> SEQ ID NO 202
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 202
atctcttatt cttctatg                                          18

<210> SEQ ID NO 203
<211> LENGTH: 30
<212> TYPE: DNA
<213> ORGANISM: Artificial Sequence

```
<220> FEATURE:
<223> OTHER INFORMATION: Synthetic Oligonucleotide

<400> SEQUENCE: 203
tctatttatc cttcttatgg ctatacttct                                        30

<210> SEQ ID NO 204
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 204
gtttactggt cttcttctta ctgggctggt ggttactggg ttggttctgc tttt            54

<210> SEQ ID NO 205
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 205
tacttcccgt ctggtctgat c                                                 21

<210> SEQ ID NO 206
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 206
atctcttatt cttatatg                                                     18

<210> SEQ ID NO 207
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 207
tctatttctc cttcttctgg ctatacttct                                        30

<210> SEQ ID NO 208
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 208
tctgtttctt ggtggtactc ttggtggtct tggggtatg                              39

<210> SEQ ID NO 209
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 209
ggtggtcatt actggctgat c                                                 21
```

<210> SEQ ID NO 210
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 210
tctatttctt cttcttatgg ctatacttct                              30

<210> SEQ ID NO 211
<211> LENGTH: 57
<212> TYPE: DNA
<213> ORGANISM: Artificial Sequence
<220> FEATURE:
<223> OTHER INFORMATION: Synthetic Oligonucleotide

<400> SEQUENCE: 211
tcttactacg gttactacgt tggttacggt tactcttctt ggtctggttc tggtatg    57

<210> SEQ ID NO 212
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 212
gctgtttacc atgctctgat c                                       21

<210> SEQ ID NO 213
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 213
atctattatt cttctatg                                           18

<210> SEQ ID NO 214
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 214
tctatttctt cttattctag ctctacttat                              30

<210> SEQ ID NO 215
<211> LENGTH: 57
<212> TYPE: DNA
<213> ORGANISM: Artificial Sequence
<220> FEATURE:
<223> OTHER INFORMATION: Synthetic Oligonucleotide

<400> SEQUENCE: 215
tctgctgttg ttcattaccc ggctggttac tgggtttact ggggttggta cgctttt    57

<210> SEQ ID NO 216
<211> LENGTH: 18
<212> TYPE: DNA
<213> ORGANISM: Artificial Sequence
<220> FEATURE:
<223> OTHER INFORMATION: Synthetic Oligonucleotide

```
<400> SEQUENCE: 216
tactgggctt ctctgatc                                                18

<210> SEQ ID NO 217
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 217
atctcttatt attatatc                                                18

<210> SEQ ID NO 218
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 218
tatatttctc cttattatgg ctctacttat                                   30

<210> SEQ ID NO 219
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 219
tcttggtctt actcttacac tactctcatc cgggttggtc tccggtttgg gctatg      56

<210> SEQ ID NO 220
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 220
tacggttact ggtgggtttc tctgttc                                      27

<210> SEQ ID NO 221
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 221
ctctattatt attctatc                                                18

<210> SEQ ID NO 222
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 222
tctatttatt cttattctag ctatacttat                                   30

<210> SEQ ID NO 223
```

```
<211> LENGTH: 42
<212> TYPE: DNA
<213> ORGANISM: Artificial Sequence
<220> FEATURE:
<223> OTHER INFORMATION: Synthetic Oligonucleotide

<400> SEQUENCE: 223
tggtggcctg gtcattactc tggttacggt tctggtgctt tg                          42

<210> SEQ ID NO 224
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 224
tcttctggtc cgtggtacta cccgatc                                           27

<210> SEQ ID NO 225
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 225
ttttcttctt cttctata                                                     18

<210> SEQ ID NO 226
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 226
tctatttctt cttcttatgg ctatacttat                                        30

<210> SEQ ID NO 227
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 227
tggtggtctg gtggttggta ctactcttac ggtatg                                 36

<210> SEQ ID NO 228
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 228
tcttactggc cgggttggcc gatc                                              24

<210> SEQ ID NO 229
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 229
```
tatatttatc cttattatgg ctatacttat                                    30

<210> SEQ ID NO 230
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 230
tgggttgttg ctggtcatta cggtatg                                       27

<210> SEQ ID NO 231
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 231
tcttcttatt ctctgatc                                                 18

<210> SEQ ID NO 232
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 232
ctctcttatt cttatatg                                                 18

<210> SEQ ID NO 233
<211> LENGTH: 30
<212> TYPE: DNA
<213> ORGANISM: Artificial Sequence
<220> FEATURE:
<223> OTHER INFORMATION: Synthetic Polypeptide

<400> SEQUENCE: 233
tctatttatt cttcttatgg ctatacttct                                    30

<210> SEQ ID NO 234
<211> LENGTH: 57
<212> TYPE: DNA
<213> ORGANISM: Artificial Sequence
<220> FEATURE:
<223> OTHER INFORMATION: Synthetic Oligonucleotide

<400> SEQUENCE: 234
tactacggtt gggcttacta ctactcttac ttcccggctt gggctggtgg tggtatt      57

<210> SEQ ID NO 235
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 235
tggtgggctt ctggtgttgg tccgttc                                       27

<210> SEQ ID NO 236
<211> LENGTH: 18
<212> TYPE: DNA

```
<213> ORGANISM: Artificial Sequence
<220> FEATURE:
<223> OTHER INFORMATION: Synthetic Oligonucleotide

<400> SEQUENCE: 236
ctctattctt cttctatc                                             18

<210> SEQ ID NO 237
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 237
tatatttctt cttattatag ctctacttat                                30

<210> SEQ ID NO 238
<211> LENGTH: 9
<212> TYPE: DNA
<213> ORGANISM: Artificial Sequence
<220> FEATURE:
<223> OTHER INFORMATION: Synthetic Oligonucleotide

<400> SEQUENCE: 238 ccggctatg                                                       9

<210> SEQ ID NO 239
<211> LENGTH: 21
<212> TYPE: DNA
<213> ORGANISM: Artificial Sequence
<220> FEATURE:
<223> OTHER INFORMATION: Synthetic Polypeptide

<400> SEQUENCE: 239
tacgtttact cttctctgat c                                         21

<210> SEQ ID NO 240
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 240
atctcttatt attctatg                                             18

<210> SEQ ID NO 241
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 241
tctatttatc cttcttatgg ctctacttat                                30

<210> SEQ ID NO 242
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 242
ccgggtgttg gtggttacta cgctatg                                   27
```

<210> SEQ ID NO 243
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 243
ctctcttatt attctatg                                                    18

<210> SEQ ID NO 244
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 244
tctatttatc cttcttatgg ctatacttat                                       30

<210> SEQ ID NO 245
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 245
ccgtctccgg gttcttacca tggtatg                                          27

<210> SEQ ID NO 246
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 246
ttctggggtc tgttc                                                       15

<210> SEQ ID NO 247
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 247
atctcttatt actctatg                                                    18

<210> SEQ ID NO 248
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 248
tctatttatc cttcttatag ctctacttat                                       30

<210> SEQ ID NO 249
<211> LENGTH: 27
<212> TYPE: DNA
<213> ORGANISM: Artificial Sequence
<220> FEATURE:

<223> OTHER INFORMATION: Synthetic Oligonucleotide

<400> SEQUENCE: 249
ccgtctccgg gtggttactc tgctttg                                27

<210> SEQ ID NO 250
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 250
ccggcttact ctgctccgat c                                      21

<210> SEQ ID NO 251
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 251
tctatttatt cttcttatgg ctctacttat                             30

<210> SEQ ID NO 252
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 252
gttggtccgg gtggtttcgg tgctttg                                27

<210> SEQ ID NO 253
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 253
ggtgtttacc tgttc                                             15

<210> SEQ ID NO 254
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 254
atctattctt cttctatc                                          18

<210> SEQ ID NO 255
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 255
tctatttatt cttcttatgg ctctacttct                             30

-continued

```
<210> SEQ ID NO 256
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 256
taccattacc cgttcggtca tgctttg                                    27

<210> SEQ ID NO 257
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 257
gctcatggtt cttctccggg ttggtactac gctccgtacg ctggtggtgg tttg      54

<210> SEQ ID NO 258
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 258
ctctcttatt cttctatg                                              18

<210> SEQ ID NO 259
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 259
tctatttatt cttcttatag ctctacttct                                 30

<210> SEQ ID NO 260
<211> LENGTH: 48
<212> TYPE: DNA
<213> ORGANISM: Artificial Sequence
<220> FEATURE:
<223> OTHER INFORMATION: Synthetic Oligonucleotide

<400> SEQUENCE: 260
ggtgctggtt actactggtg gcattactac tacgttcatg gtgctatg             48

<210> SEQ ID NO 261
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 261
tactactact cttctccgat c                                          21

<210> SEQ ID NO 262
<211> LENGTH: 30
<212> TYPE: DNA
<213> ORGANISM: Artificial Sequence
<220> FEATURE:
<223> OTHER INFORMATION: Synthetic Oligonucleotide
```

<400> SEQUENCE: 262
tatatttctc cttcttctgg ctatacttct						30

<210> SEQ ID NO 263
<211> LENGTH: 42
<212> TYPE: DNA
<213> ORGANISM: Artificial Sequence
<220> FEATURE:
<223> OTHER INFORMATION: Synthetic Oligonucleotide

<400> SEQUENCE: 263
ggttacccgg tttactcttg ggtttggtct ttcggtgctt tt						42

<210> SEQ ID NO 264
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 264
gctgcttacc attggccgcc gctgttc						27

<210> SEQ ID NO 265
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 265
ctctattatt cttctatg						18

<210> SEQ ID NO 266
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 266
tatatttctc cttattctgg ctatacttct						30

<210> SEQ ID NO 267
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 267
tactgggcta tg						12

<210> SEQ ID NO 268
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 268
gcttactacc tgatca						16

<210> SEQ ID NO 269
<211> LENGTH: 18

```
<212> TYPE: DNA
<213> ORGANISM: Artificial Sequence
<220> FEATURE:
<223> OTHER INFORMATION: Synthetic Oligonucleotide

<400> SEQUENCE: 269
atctattatt cttctatc                                              18

<210> SEQ ID NO 270
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 270
tctatttatc cttcttctgg ctatacttat                                 30

<210> SEQ ID NO 271
<211> LENGTH: 57
<212> TYPE: DNA
<213> ORGANISM: Artificial Sequence
<220> FEATURE:
<223> OTHER INFORMATION: Synthetic Oligonucleotide

<400> SEQUENCE: 271
tgggctccgc attcttcttc ttggtggtct gtttacggtt ggtctgcttg ggctttt    57

<210> SEQ ID NO 272
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 272
tctgttcatt ggtacccgtt ca                                         22

<210> SEQ ID NO 273
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 273
atctcttatt attctatc                                              18

<210> SEQ ID NO 274
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 274
tatatttatc cttattctgg ctctacttat                                 30

<210> SEQ ID NO 275
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 275
```

```
tgggctcatt acggttacta cggtttctct tactctgttt actctggtgg tatg    54

<210> SEQ ID NO 276
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 276
tcttcttatt ctctgatc                                            18

<210> SEQ ID NO 277
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 277
atctcttctt attatatc                                            18

<210> SEQ ID NO 278
<211> LENGTH: 57
<212> TYPE: DNA
<213> ORGANISM: Artificial Sequence
<220> FEATURE:
<223> OTHER INFORMATION: Synthetic Oligonucleotide

<400> SEQUENCE: 278
ccgtggtctc attactcttc tggtgcttac tggcatccgt ggtctggtca tgctttg    57

<210> SEQ ID NO 279
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 279
tactctccgt cttctttcct gatca                                    25

<210> SEQ ID NO 280
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 280
atctattatt cttatatc                                            18

<210> SEQ ID NO 281
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 281
tctatttctt cttcttctgg ctatacttct                               30

<210> SEQ ID NO 282
<211> LENGTH: 42
<212> TYPE: DNA
<213> ORGANISM: Artificial Sequence
```

```
<220> FEATURE:
<223> OTHER INFORMATION: Synthetic Oligonucleotide

<400> SEQUENCE: 282
tcttacggtt actactacta cttctactac tacggtggta tg                    42

<210> SEQ ID NO 283
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 283
ggtcattact acccgtacta cctgttca                                    28

<210> SEQ ID NO 284
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 284
atctattatt cttatatg                                               18

<210> SEQ ID NO 285
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 285
tctatttatt cttattctgg ctatacttat                                  30

<210> SEQ ID NO 286
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 286
tctgtttggg gttacccgta cggtatg                                     27

<210> SEQ ID NO 287
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 287
tcttactctg gttggggtcc gttca                                       25

<210> SEQ ID NO 288
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 288
atctcttctt cttatatc                                               18
```

<210> SEQ ID NO 289
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 289
tctatttctt cttcttctag ctatacttat                              30

<210> SEQ ID NO 290
<211> LENGTH: 57
<212> TYPE: DNA
<213> ORGANISM: Artificial Sequence
<220> FEATURE:
<223> OTHER INFORMATION: Synthetic Oligonucleotide

<400> SEQUENCE: 290
tctgcttacc cgttctcttg gtcttacccg tcttacgttg gttactactc tggtttg    57

<210> SEQ ID NO 291
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 291
ttctactact ctctgatca                                          19

<210> SEQ ID NO 292
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 292
tctatttatt cttcttatag ctatacttct                              30

<210> SEQ ID NO 293
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 293
tcttacggtc cgtgggctcc gggttgggct gcttactggg gtggttacgg tatg       54

<210> SEQ ID NO 294
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 294
tactctggtc cgatca                                             16

<210> SEQ ID NO 295
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 295
tatatttatc cttattatag ctatacttat                              30

<210> SEQ ID NO 296
<211> LENGTH: 57
<212> TYPE: DNA
<213> ORGANISM: Artificial Sequence
<220> FEATURE:
<223> OTHER INFORMATION: Synthetic Oligonucleotide

<400> SEQUENCE: 296
tctgttactt accattcttc tggttgggtt ccgccgtggt actggggtta cgctttt    57

<210> SEQ ID NO 297
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 297
tactcttctc cgatca                                              16

<210> SEQ ID NO 298
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 298
tatatttctc cttattatag ctatacttat                              30

<210> SEQ ID NO 299
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 299
tctgtttggg tttactgggg ttcttggtac tcttactctc atgcttctgg tttg       54

<210> SEQ ID NO 300
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 300
ggttctgttt ggctgttca                                           19

<210> SEQ ID NO 301
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 301
atctcttctt cttctatg                                            18

<210> SEQ ID NO 302

-continued

```
<211> LENGTH: 57
<212> TYPE: DNA
<213> ORGANISM: Artificial Sequence
<220> FEATURE:
<223> OTHER INFORMATION: Synthetic Oligonucleotide

<400> SEQUENCE: 302
tacggttctc attggtctcc gtcttactct ggttggtact actactctta cgctttg      57

<210> SEQ ID NO 303
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 303
gcttacgctt acctgatc                                                  18

<210> SEQ ID NO 304
<211> LENGTH: 42
<212> TYPE: DNA
<213> ORGANISM: Artificial Sequence
<220> FEATURE:
<223> OTHER INFORMATION: Synthetic Oligonucleotide

<400> SEQUENCE: 304
tctggtggtc atttctacta ctggtacgtt gctgctgcta tg                       42

<210> SEQ ID NO 305
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 305
tcttacgttg gtggtccgtt ca                                             22

<210> SEQ ID NO 306
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 306
tctatttctt cttcttatag ctctacttat                                     30

<210> SEQ ID NO 307
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 307
ggttactggt acgtttacgt tggttggggt gcttactacg gtccggttgg tatg          54

<210> SEQ ID NO 308
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 308
```
gcttcttggt acccaatca	19

<210> SEQ ID NO 309
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 309
atctattctt cttctatg	18

<210> SEQ ID NO 310
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 310
ccgggttact ggggttacta ctggggtgct tacggtatg	39

<210> SEQ ID NO 311
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 311
gcttacgctc cgttca	16

<210> SEQ ID NO 312
<211> LENGTH: 42
<212> TYPE: DNA
<213> ORGANISM: Artificial Sequence
<220> FEATURE:
<223> OTHER INFORMATION: Synthetic Oligonucleotide

<400> SEQUENCE: 312
tcttctgctt ggttcggtca tgctggtttc ggtggtgcta tg	42

<210> SEQ ID NO 313
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 313
tactgggctc cgatca	16

<210> SEQ ID NO 314
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 314
atctattatt attatatg	18

<210> SEQ ID NO 315
<211> LENGTH: 30
<212> TYPE: DNA

<213> ORGANISM: Artificial Sequence
<220> FEATURE:
<223> OTHER INFORMATION: Synthetic Oligonucleotide

<400> SEQUENCE: 315
tctatttatt cttattctgg ctctacttat                                    30

<210> SEQ ID NO 316
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 316
tacgcttctt acgttggtta ctacccgtgg gctttg                             36

<210> SEQ ID NO 317
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 317
ggttctgctt cttctgctct gatca                                         25

<210> SEQ ID NO 318
<211> LENGTH: 45
<212> TYPE: DNA
<213> ORGANISM: Artificial Sequence
<220> FEATURE:
<223> OTHER INFORMATION: Synthetic Oligonucleotide

<400> SEQUENCE: 318
ttctactctt ctttctactt cttctggtac ccgccggctg gtttg                   45

<210> SEQ ID NO 319
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 319
gcttactggt gggttggtcc gatca                                         25

<210> SEQ ID NO 320
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 320
ctctcttatt cttctatc                                                 18

<210> SEQ ID NO 321
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 321
tatatttctt cttcttatgg ctatacttct                                    30

<210> SEQ ID NO 322
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 322
ttctctgctt actgggcttg gcatggtttg                              30

<210> SEQ ID NO 323
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 323
gtttctggtg gtggtggtct gatca                                   25

<210> SEQ ID NO 324
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 324
atctattctt cttatatc                                           18

<210> SEQ ID NO 325
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 325
tatatttatt cttattctgg ctatacttat                              30

<210> SEQ ID NO 326
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 326
tggtaccatc cgtactggta cgcttctgct att                          33

<210> SEQ ID NO 327
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 327
tgggcttacg gtccgttca                                          19

<210> SEQ ID NO 328
<211> LENGTH: 18
<212> TYPE: DNA
<213> ORGANISM: Artificial Sequence
<220> FEATURE:

<223> OTHER INFORMATION: Synthetic Oligonucleotide

<400> SEQUENCE: 328
atctattatt attctatg                                                          18

<210> SEQ ID NO 329
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 329
tcttctccgg gtgctgatta cggtttg                                                27

<210> SEQ ID NO 330
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 330
tcttacgttt actacctgat ca                                                     22

<210> SEQ ID NO 331
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 331
tatatttatc cttattctag ctatacttat                                             30

<210> SEQ ID NO 332
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 332
taccatggtt tctacggtat g                                                      21

<210> SEQ ID NO 333
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 333
tctgcttggt gggcttctct gttca                                                  25

<210> SEQ ID NO 334
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 334
atctcttctt attctatc                                                          18

```
<210> SEQ ID NO 335
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 335
tctatttatc cttattctag ctatacttat                              30

<210> SEQ ID NO 336
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 336
tactctggtt tcgctatg                                           18

<210> SEQ ID NO 337
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 337
tactcttacg gttacgctct gttca                                   25

<210> SEQ ID NO 338
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 338
ctctcttctt attatatg                                           18

<210> SEQ ID NO 339
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 339
tctatttatc cttattatag ctatacttat                              30

<210> SEQ ID NO 340
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 340
tactggtctg gtttt                                              15

<210> SEQ ID NO 341
<211> LENGTH: 25
<212> TYPE: DNA
<213> ORGANISM: Artificial Sequence
<220> FEATURE:
<223> OTHER INFORMATION: Synthetic Oligonucleotide
```

```
<400> SEQUENCE: 341
tggtactacg gttggcatct gatca                                          25

<210> SEQ ID NO 342
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 342
atctcttatt cttctatc                                                  18

<210> SEQ ID NO 343
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 343
tacggttact tcggtatg                                                  18

<210> SEQ ID NO 344
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 344
tcttactctg cttctctgtt ca                                             22

<210> SEQ ID NO 345
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 345
ctctattatt cttatatc                                                  18

<210> SEQ ID NO 346
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 346
tctatttctc cttcttatag ctctacttat                                     30

<210> SEQ ID NO 347
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 347
gtttcttact ggggtgctgg tatg                                           24

<210> SEQ ID NO 348
<211> LENGTH: 25
```

```
<212> TYPE: DNA
<213> ORGANISM: Artificial Sequence
<220> FEATURE:
<223> OTHER INFORMATION: Synthetic Oligonucleotide

<400> SEQUENCE: 348
tggggttctt acgttgctct gttca                                    25

<210> SEQ ID NO 349
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 349
atctattctt attctatc                                            18

<210> SEQ ID NO 350
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 350
tctatttatt cttattatgg ctctacttat                               30

<210> SEQ ID NO 351
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 351
gttggtccgg gttcttacgg tggtttg                                  27

<210> SEQ ID NO 352
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 352
tactactctt actctgtttg gctgatca                                 28

<210> SEQ ID NO 353
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 353
atctcttatt attatatg                                            18

<210> SEQ ID NO 354
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 354
```

```
tatatttctc cttcttctag ctatacttct                                      30

<210> SEQ ID NO 355
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 355
tggtacggtt gggctttg                                                   18

<210> SEQ ID NO 356
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 356
tcttactacc cgatca                                                     16

<210> SEQ ID NO 357
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 357
ctctcttatt attatatc                                                   18

<210> SEQ ID NO 358
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 358
ttctctggtt gggctttg                                                   18

<210> SEQ ID NO 359
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 359
tggggttacg gtgctctgat ca                                              22

<210> SEQ ID NO 360
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 360
tctatttatc cttctcctgg ctatacttct                                      30

<210> SEQ ID NO 361
<211> LENGTH: 18
<212> TYPE: DNA
<213> ORGANISM: Artificial Sequence
```

```
<220> FEATURE:
<223> OTHER INFORMATION: Synthetic Oligonucleotide

<400> SEQUENCE: 361
catggttggt acgtttg                                                    18

<210> SEQ ID NO 362
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 362
tactactctc tgttca                                                     16

<210> SEQ ID NO 363
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 363
tatatttctc cttcttatgg ctatacttat                                      30

<210> SEQ ID NO 364
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 364
ggttacttct actcttgggg tggtatg                                         27

<210> SEQ ID NO 365
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 365
tactggtacg gtgttgctcc gatca                                           25

<210> SEQ ID NO 366
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 366
tatatttatt cttcttatgg ctctacttat                                      30

<210> SEQ ID NO 367
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 367
gcttcttggt acgctttg                                                   18
```

```
<210> SEQ ID NO 368
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 368
tacttctact cttcttactc tccgatca                                    28

<210> SEQ ID NO 369
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 369
tatatttatc cttcttatag ctctacttct                                  30

<210> SEQ ID NO 370
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 370
gcttcttact gggctttg                                               18

<210> SEQ ID NO 371
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 371
taccattacg gttactaccc gttca                                       25

<210> SEQ ID NO 372
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 372
ctctcttctt cttatatc                                               18

<210> SEQ ID NO 373
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 373
gcttcttggt gggctatt                                               18

<210> SEQ ID NO 374
<211> LENGTH: 28
<212> TYPE: DNA
<213> ORGANISM: Artificial Sequence
<220> FEATURE:
<223> OTHER INFORMATION: Synthetic Oligonucleotide
```

```
<400> SEQUENCE: 374
tctttctact ggggttaccc gccgttca                                28

<210> SEQ ID NO 375
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 375
tctatttatt cttattatgg ctatacttat                              30

<210> SEQ ID NO 376
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 376
tggtacgctt tt                                                 12

<210> SEQ ID NO 377
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 377
tactaccatc cgatca                                             16

<210> SEQ ID NO 378
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 378
tctatttatc cttattatag ctctacttat                              30

<210> SEQ ID NO 379
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 379
gtttggtacg gtgctatg                                           18

<210> SEQ ID NO 380
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 380
ggttcttact cttacccgtt ca                                      22

<210> SEQ ID NO 381
```

<210> SEQ ID NO 381
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 381
tctatttatc cttattctgg ctatacttat                               30

<210> SEQ ID NO 382
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 382
tggcatggtt acggtatt                                            18

<210> SEQ ID NO 383
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 383
ggtccggctt actcttacct gttca                                    25

<210> SEQ ID NO 384
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 384
ggttactacg gtttg                                               15

<210> SEQ ID NO 385
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 385
gctttcggtt ggccgctgat ca                                       22

<210> SEQ ID NO 386
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 386
tatatttatc cttattctgg ctctacttct                               30

<210> SEQ ID NO 387
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 387

```
gctggttggt acgtttacgg tccgtacggt ttt                              33
```

<210> SEQ ID NO 388
<211> LENGTH: 42
<212> TYPE: DNA
<213> ORGANISM: Artificial Sequence
<220> FEATURE:
<223> OTHER INFORMATION: Synthetic Oligonucleotide

<400> SEQUENCE: 388

```
gctgctggtc cgtactggta ctcttactgg tactctgcta tg                    42
```

<210> SEQ ID NO 389
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 389

```
tacggtcatt acctgatca                                              19
```

<210> SEQ ID NO 390
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 390

```
ctctattctt attctatg                                               18
```

<210> SEQ ID NO 391
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 391

```
tctatttctt cttattatgg ctctacttat                                  30
```

<210> SEQ ID NO 392
<211> LENGTH: 5
<212> TYPE: PRT
<213> ORGANISM: Artificial Sequence
<220> FEATURE:
<223> OTHER INFORMATION: Artificial Polypeptide

<400> SEQUENCE: 392

Ser Val Ser Ser Ala
1               5

<210> SEQ ID NO 393
<211> LENGTH: 7
<212> TYPE: PRT
<213> ORGANISM: Artificial Sequence
<220> FEATURE:
<223> OTHER INFORMATION: Artificial Polypeptide

<400> SEQUENCE: 393

Ser Ala Ser Ser Leu Tyr Ser
1               5

<210> SEQ ID NO 394

```
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(4)
<223> OTHER INFORMATION: X is 25% Y, 20%S, 20%G, 10%A and 5% each of F,
      W, H, P and V.
<220> FEATURE:
<221> NAME/KEY: MISC_FEATURE
<222> LOCATION: (5)..(5)
<223> OTHER INFORMATION: X is P or L.
<220> FEATURE:
<221> NAME/KEY: MISC_FEATURE
<222> LOCATION: (6)..(6)
<223> OTHER INFORMATION: X is I or L.

<400> SEQUENCE: 394

Xaa Xaa Xaa Xaa Xaa Xaa
1               5

<210> SEQ ID NO 395
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: X is I or L.
<220> FEATURE:
<221> NAME/KEY: MISC_FEATURE
<222> LOCATION: (2)..(5)
<223> OTHER INFORMATION: X is Y or S.
<220> FEATURE:
<221> NAME/KEY: MISC_FEATURE
<222> LOCATION: (6)..(6)
<223> OTHER INFORMATION: X is I or M.

<400> SEQUENCE: 395

Xaa Xaa Xaa Xaa Xaa Xaa
1               5

<210> SEQ ID NO 396
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: X is Y or S.
<220> FEATURE:
<221> NAME/KEY: MISC_FEATURE
<222> LOCATION: (3)..(3)
<223> OTHER INFORMATION: X is Y or S.
<220> FEATURE:
<221> NAME/KEY: MISC_FEATURE
<222> LOCATION: (4)..(4)
<223> OTHER INFORMATION: X is P or S.
<220> FEATURE:
<221> NAME/KEY: MISC_FEATURE
<222> LOCATION: (5)..(6)
<223> OTHER INFORMATION: X is Y or S.
<220> FEATURE:
<221> NAME/KEY: MISC_FEATURE
<222> LOCATION: (7)..(7)
<223> OTHER INFORMATION: X is G or S.
<220> FEATURE:
<221> NAME/KEY: MISC_FEATURE
<222> LOCATION: (8)..(8)
```

```
<223> OTHER INFORMATION: X is Y or S.
<220> FEATURE:
<221> NAME/KEY: MISC_FEATURE
<222> LOCATION: (10)..(10)
<223> OTHER INFORMATION: X is Y or S.

<400> SEQUENCE: 396

Xaa Ile Xaa Xaa Xaa Xaa Xaa Xaa Thr Xaa
1               5                   10

<210> SEQ ID NO 397
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(8)
<223> OTHER INFORMATION: X is 25% Y, 20%S, 20%G, 10%A and 5% each of F,
      W, H, P and V.
<220> FEATURE:
<221> NAME/KEY: MISC_FEATURE
<222> LOCATION: (9)..(9)
<223> OTHER INFORMATION: X is A or G.
<220> FEATURE:
<221> NAME/KEY: MISC_FEATURE
<222> LOCATION: (10)..(10)
<223> OTHER INFORMATION: X is F, I, L, or M.

<400> SEQUENCE: 397

Arg Xaa Xaa Xaa Xaa Xaa Xaa Xaa Xaa Xaa Asp
1               5                   10

<210> SEQ ID NO 398
<211> LENGTH: 7
<212> TYPE: PRT
<213> ORGANISM: Artificial Sequence
<220> FEATURE:
<223> OTHER INFORMATION: Artificial Polypeptide

<400> SEQUENCE: 398

Gly Ser Tyr Ser Tyr Pro Phe
1               5
```